US008597801B2

(12) United States Patent
Kwak et al.

(10) Patent No.: US 8,597,801 B2
(45) Date of Patent: Dec. 3, 2013

(54) HETEROCYCLIC COMPOUND, ORGANIC LIGHT-EMITTING DEVICE INCLUDING THE HETEROCYCLIC COMPOUND, AND FLAT DISPLAY DEVICE INCLUDING THE ORGANIC LIGHT-EMITTING DEVICE

(75) Inventors: Yoon-Hyun Kwak, Yongin (KR); Seok-Hwan Hwang, Yongin (KR); Young-Kook Kim, Yongin (KR); Sun-Young Lee, Yongin (KR); Hye-Jin Jung, Yongin (KR); Jin-O Lim, Yongin (KR); Sang-Hyun Han, Yongin (KR); Hee-Joo Ko, Yongin (KR); Jong-Hyuk Lee, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 21 days.

(21) Appl. No.: 13/137,553

(22) Filed: Aug. 25, 2011

(65) Prior Publication Data

US 2012/0292603 A1  Nov. 22, 2012

(30) Foreign Application Priority Data

May 9, 2011   (KR) .................. 10-2011-0043439

(51) Int. Cl.
H01L 51/54 (2006.01)

(52) U.S. Cl.
USPC .......... 428/690; 428/917; 313/504; 313/505; 313/506; 257/40; 257/E51.05; 257/E51.026; 257/E51.032; 544/179; 544/183; 544/245; 544/342

(58) Field of Classification Search
USPC .......... 428/690, 917; 313/504, 505, 506; 257/E51.026, 40, E51.05, E51.032; 544/179, 183, 245, 342
See application file for complete search history.

(56) References Cited

U.S. PATENT DOCUMENTS

| 5,635,308 | A | 6/1997 | Inoue et al. |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 2006/0124924 | A1* | 6/2006 | Suh et al. ............ 257/40 |
| 2006/0251918 | A1 | 11/2006 | Iwakuma et al. |
| 2010/0123388 | A1 | 5/2010 | Yokoyama et al. |

FOREIGN PATENT DOCUMENTS

| DE | 102009052428 | * | 5/2011 |
| JP | 8-12600 | | 1/1996 |
| JP | 2000-003782 | | 1/2000 |
| JP | 2006-066580 A | | 3/2006 |
| KR | 10-2005-008550 A | | 8/2005 |
| KR | 10-2010-0003624 A | | 1/2010 |
| KR | 10-2010-0014416 A | | 5/2010 |

OTHER PUBLICATIONS

Sakamoto et al., Synthesis, Characterization, and Electron-Transport Property of Perfluorinated Phyenylene Dendrimers, J. Am. Chem. Soc., 2000, pp. 1832-1833.

OTHER PUBLICATIONS

Adachi et al., Confinement of Charge Carriers and Molecular Excitons Within 5-NM-Thick Emitter Layer in Organic Electroluminescent Devices With a Double Heterostructure, Appl. Phys. Lett. 57 (6), Aug. 6, 1990, pp. 531-533.

Tang et al., Organic Electroluminescent Diodes, Appl. Phys. Lett. 51 (12, Sep. 21, 1987, pp. 913-915.

Yamaguchi et al., Diphenylamino-Substituted 2,5-Diarylsiloles for Single-Layer Organic Electroluminescent Devices, Chemistry Letters 2001, Nov. 10, 2000, pp. 98-99.

* cited by examiner

*Primary Examiner* — Gregory Clark

(74) *Attorney, Agent, or Firm* — Lee & Morse, P.C.

(57) ABSTRACT

A heterocyclic compound includes compounds represented by Formula 1 or Formula 2 below:

<Formula 1>

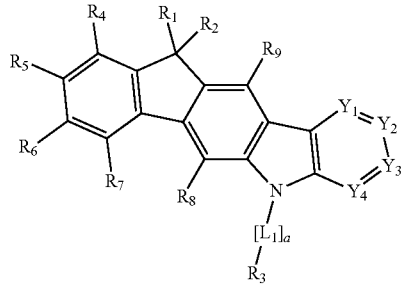

-continued

<Formula 2>

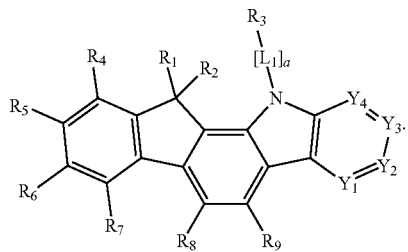

26 Claims, 1 Drawing Sheet

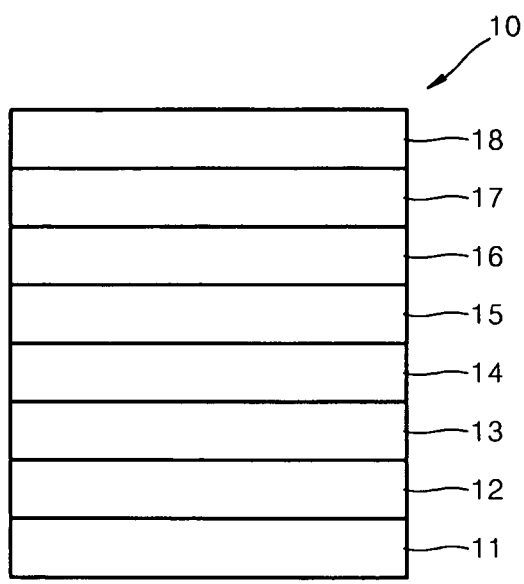

HETEROCYCLIC COMPOUND, ORGANIC LIGHT-EMITTING DEVICE INCLUDING THE HETEROCYCLIC COMPOUND, AND FLAT DISPLAY DEVICE INCLUDING THE ORGANIC LIGHT-EMITTING DEVICE

BACKGROUND

1. Field

The present invention relates to a heterocyclic compound, an organic light-emitting device including the heterocyclic compound, and a flat display device including the organic light-emitting device.

2. Description of the Related Art

Organic light-emitting devices are active emission-type devices, and have a wide viewing angle and a high contrast ratio, short response time, high brightness, a low driving voltage, and a high response rate, and produce a plurality of colors.

Generally, an organic light-emitting device includes a substrate, an anode formed on the substrate, and a hole transport layer, an emission layer, an electron transport layer, and a cathode sequentially formed on the anode in the stated order. The hole transport layer, the emission layer, and the electron transport layer may be organic films formed of an organic compound.

An organic light-emitting device having such a structure is driven as follow: when a voltage is applied between the anode and the cathode, holes injected through the anode pass through the hole transport layer and move toward the emission layer, and electrons injected through the cathode pass through the electron transport layer and move toward the emission layer. The holes and the electrons, which are carriers, are recombined in the emission layer to form excitons. The excitons are changed from an excited state to a ground state, thereby generating light.

SUMMARY

According to an aspect of the present invention, there is provided a heterocyclic compound represented by Formula 1 or Formula 2 below:

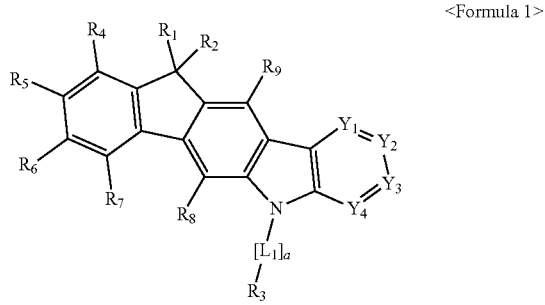

<Formula 1>

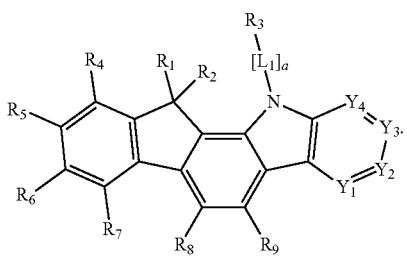

<Formula 2> wherein $Y_1$ to $Y_4$ are each independently N or $C(R_{10})$, and one or more of $Y_1$ to $Y_4$ are N, and when two or more of $Y_1$ to $Y_4$ are $C(R_{10})$, a plurality of $R_{10}$ are identical to or different from each other, $R_1$ to $R_{10}$ are each independently a hydrogen atom, a deuterium atom, a halogen atom, a hydroxyl group, a cyano group, a nitro group, a carboxylic group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ heteroaryl group, or a group represented by $N(Q_1)(Q_2)$ where $Q_1$ and $Q_2$ are each independently a hydrogen atom, a deuterium atom, a halogen atom, a hydroxyl group, a cyano group, an amino group, a nitro group, a carboxylic group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ heteroaryl group, $L_1$ is a substituted or unsubstituted $C_6$-$C_{30}$ arylene group or a substituted or unsubstituted $C_3$-$C_{30}$ heteroarylene group, and a is an integer from 1 to 3.

According to some embodiments, $Y_1$ is N and $Y_2$, $Y_3$ and $Y_4$ each are $C(R_{10})$.

According to some embodiments, $R_1$ to $R_{10}$ are each independently a hydrogen atom, a deuterium atom, a halogen atom, a hydroxyl group, a cyano group, a nitro group, a carboxylic group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted methoxy group, a substituted or unsubstituted ethoxy group, a substituted or unsubstituted phenyl group, a substituted or unsubstituted biphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted phenanthridinyl group, a substituted or unsubstituted phenanthrolinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyridoindolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted carbazolyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted benzooxazolyl group, a substituted or unsubstituted isooxazolyl group, a substituted or unsubstituted oxadiazolyl group, a substituted or unsubstituted triazolyl group, a substituted or unsubstituted triazinyl group, a substituted or unsubstituted tetrazolyl group, or a group represented by $N(Q_1)(Q_2)$ where $Q_1$ and $Q_2$ are each independently a hydrogen atom, a deuterium atom, a halogen atom, a hydroxyl group, a cyano group, an amino group, a nitro group, a carboxylic group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyridinyl group.

According to some embodiments, $R_1$ to $R_{10}$ are each independently a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted imidazolyl group, a substituted or unsubstituted benzoimidazolyl group, a substituted or unsubstituted pyridinyl group, a substituted or unsubstituted quinolinyl group, a substituted or unsubstituted pyrimidinyl group, a substituted or unsubstituted imidazopyrimidinyl group, a substituted or unsubstituted indolyl group, a substituted or unsubstituted pyridoindolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxadiazolyl group, a substituted or unsubstituted triazinyl group, or a group represented by $N(Q_1)(Q_2)$ where $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group.

According to some embodiments, $R_3$ is a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted imidazolyl group, a substituted or unsubstituted benzoimidazolyl group, a substituted or unsubstituted pyridinyl group, a substituted or unsubstituted pyrimidinyl group, a substituted or unsubstituted quinolinyl group, a substituted or unsubstituted imidazopyrimidinyl group, a substituted or unsubstituted indolyl group, a substituted or unsubstituted pyridoindolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxadiazolyl group, a substituted or unsubstituted triazinyl group, or a group represented by $N(Q_1)(Q_2)$ where $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group, and $R_1$, $R_2$, and $R_4$ to $R_{10}$ are each independently a hydrogen atom, a deuterium atom, a halogen atom, a cyano group, a substituted or unsubstituted methyl group, or a substituted or unsubstituted phenyl group.

According to some embodiments, $R_3$ is a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, or any one of groups represented by Formulae 2A to 2S below, and $R_1$, $R_2$, and $R_4$ to $R_{10}$ are each independently a hydrogen atom, a deuterium atom, a halogen atom, a cyano group, a substituted or unsubstituted methyl group, or a substituted or unsubstituted phenyl group:

<Formula 2A>

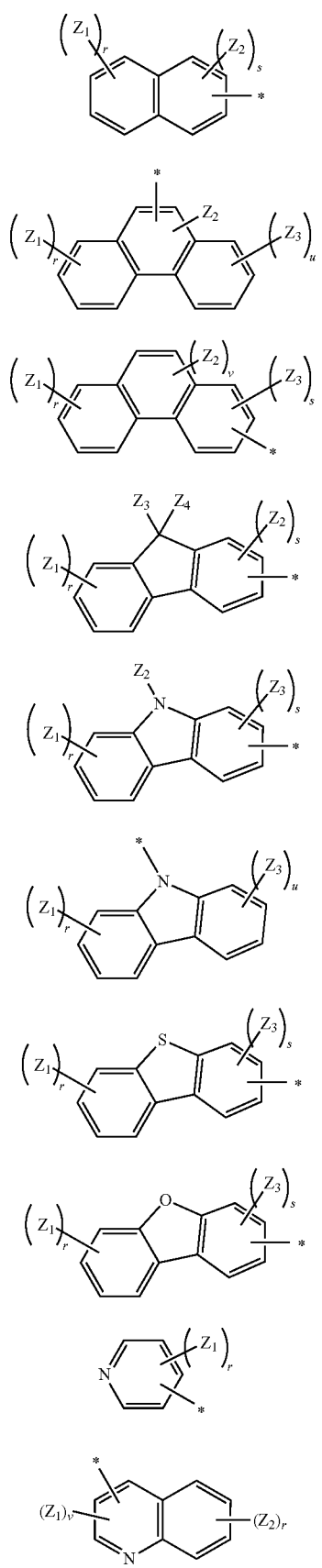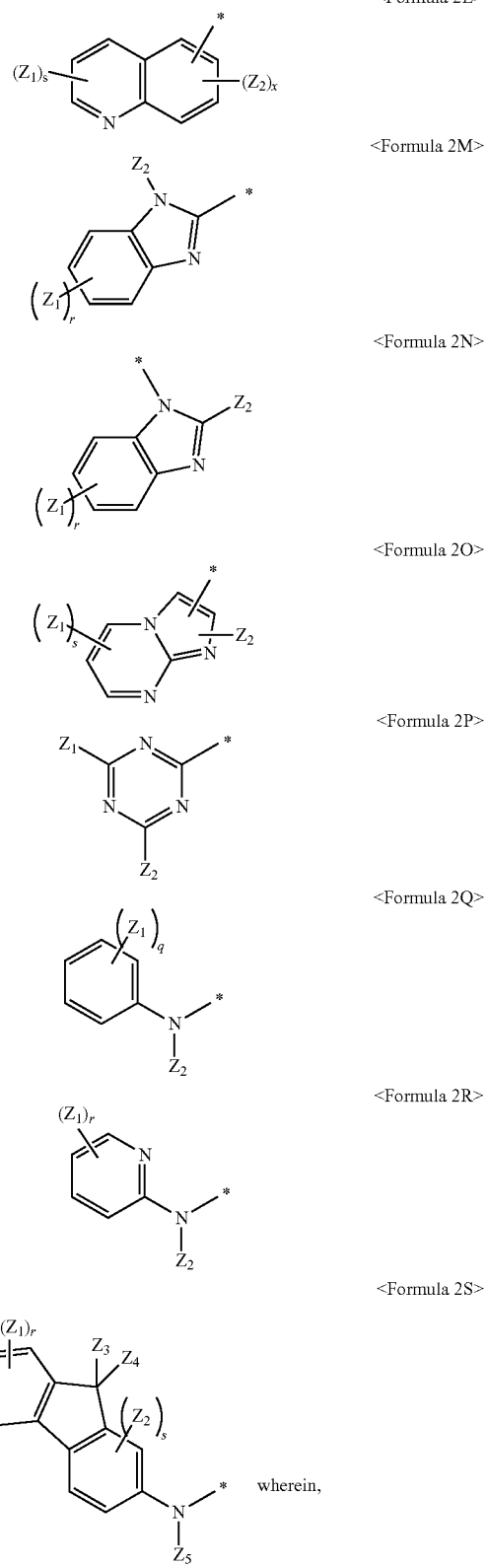
wherein,
$Z_1$, $Z_2$, $Z_3$, $Z_4$ and $Z_5$ are each independently a hydrogen atom, a deuterium atom, a halogen atom, a hydroxyl group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted biphenyl group, a substituted or unsubstituted pyridinyl group, a substituted or unsubstituted naphthyl group, or a substituted or unsubstituted anthryl group, a plurality of $Z_1$, $Z_2$, $Z_3$, $Z_4$ and $Z_5$ are identical to or different from each other, q is an integer from 1 to 5, r and u are each independently an integer from 1 to 4, s and x are each independently an integer from 1 to 3, v is an integer from 1 to 2, and * represents a binding site.

According to some embodiments, $R_3$ is a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, or any one of groups represented by Formulae 3A to 3P below, and $R_1$, $R_2$ and $R_4$ to $R_{10}$ are each independently a hydrogen atom, a deuterium atom, a halogen atom, a cyano group, a substituted or unsubstituted methyl group, or a substituted or unsubstituted phenyl group:

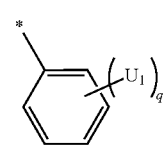
<Formula 3A>

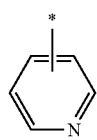
<Formula 3B>

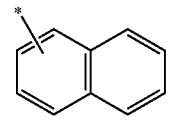
<Formula 3C>

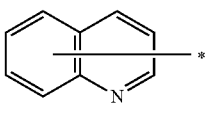
<Formula 3D>

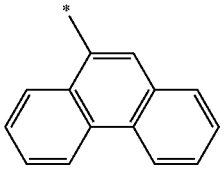
<Formula 3E>

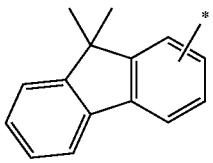
<Formula 3F>

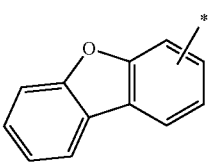
<Formula 3G>

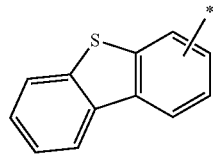
<Formula 3H>

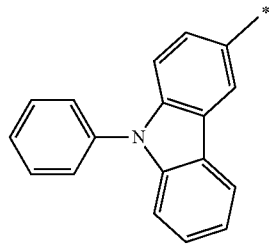
<Formula 3I>

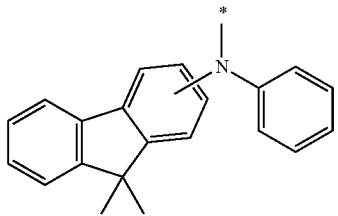
<Formula 3J>

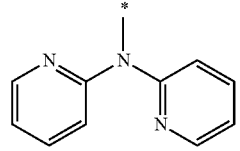
<Formula 3K>

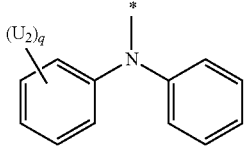
<Formula 3L>

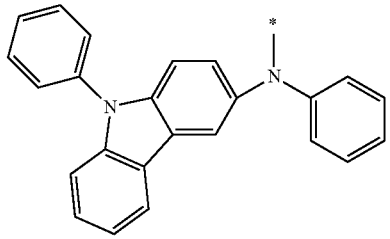
<Formula 3M>

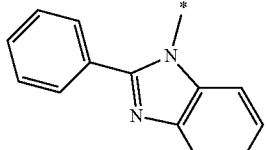
<Formula 3N>

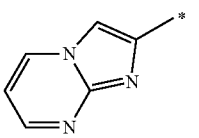
<Formula 3O>

<Formula 3P>

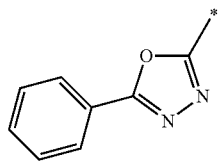

wherein,

U₁ is a hydrogen atom, a deuterium atom, a halogen atom, or a methoxy group and U₂ is a hydrogen atom or a halogen atom, wherein a plurality of $U_1$ and $U_2$ are identical to or different from each other, q is an integer of 1 to 5, and * indicates a binding site.

According to some embodiments, $L_1$ is a substituted or unsubstituted phenylene group, a substituted or unsubstituted naphthylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted pherylenylene group, a substituted or unsubstituted fluorenylene group, a substituted or unsubstituted spiro-fluorenylene group, a substituted or unsubstituted carbazolylene group, a substituted or unsubstituted pyridinylene group, a substituted or unsubstituted benzoimidazolene group, a substituted or unsubstituted imidazopyrimidinylene group, or a substituted or unsubstituted oxadiazolylene group.

According to some embodiments, $L_1$ is any one of groups represented by Formulae 4A to 4F below:

<Formula 4A>

<Formula 4B>

<Formula 4C>

<Formula 4D>

<Formula 4E>

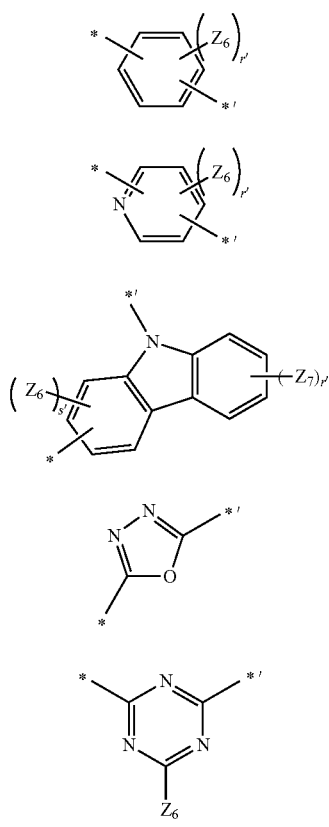

<Formula 4F>

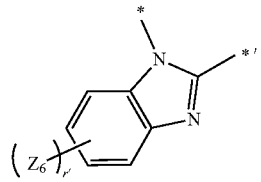

wherein, $Z_6$ is a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted methoxy group, or a substituted or unsubstituted phenyl group, a plurality of $Z_6$ are identical to or different from each other, r' is an integer from 1 to 4, s' is an integer from 1 to 3, and * and *' each indicate a binding site.

According to some embodiments, a is 0 or 1.

According to some embodiments, the heterocyclic compound represented by Formula 1 or Formula 2 above is any one of compounds represented by Compound 1 to 112 below:

1

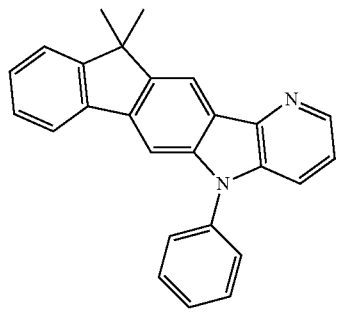

2

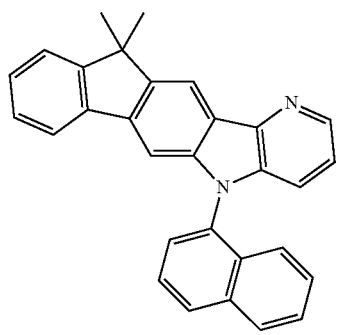

3

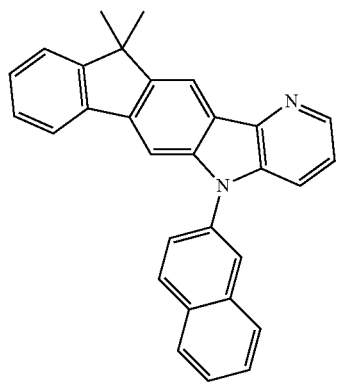

4
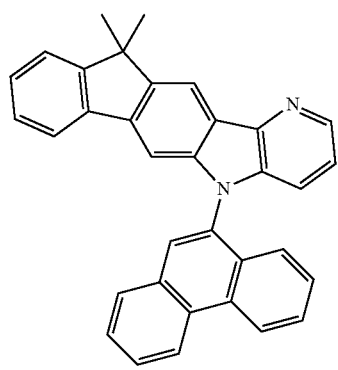
5
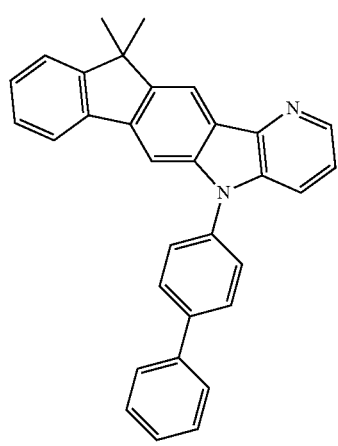
6
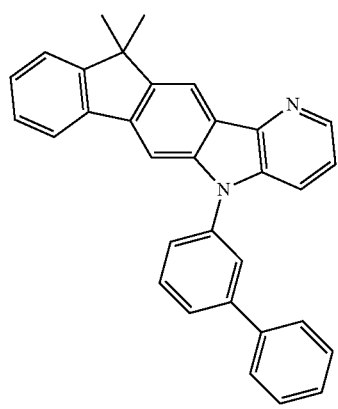
7
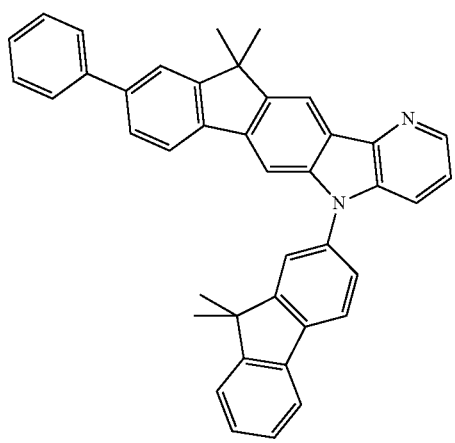
8
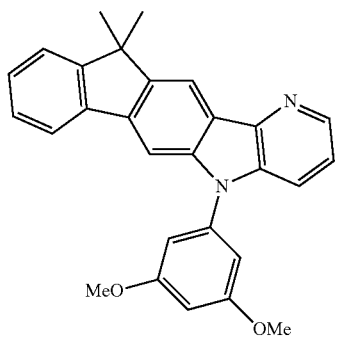
9
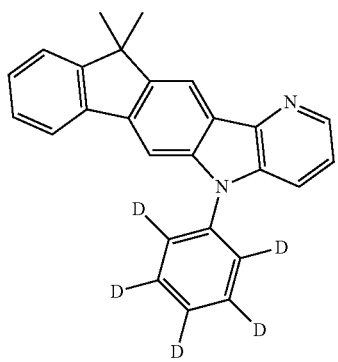
10
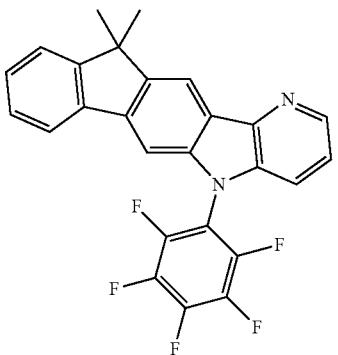
11
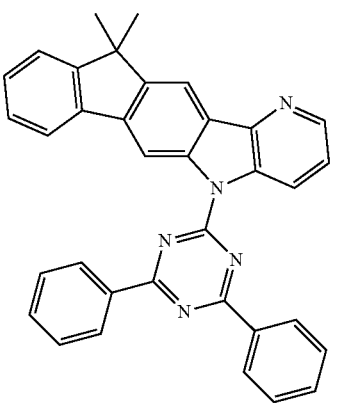

12
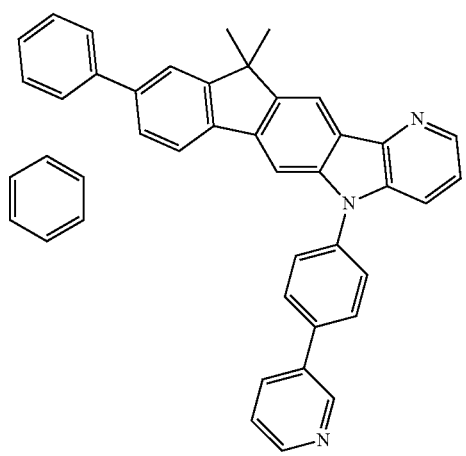
13
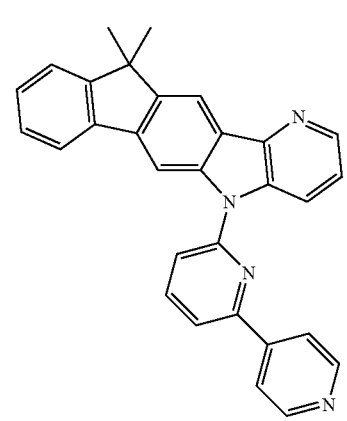
14
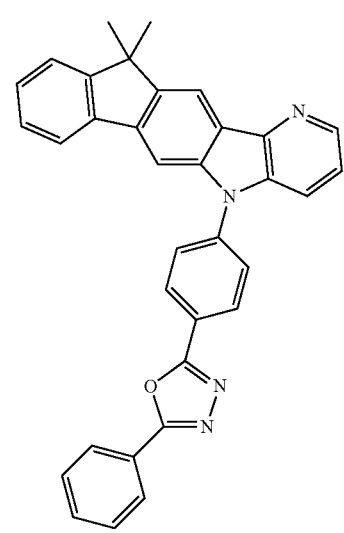
15
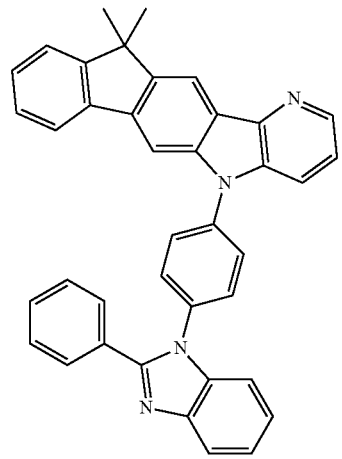
16
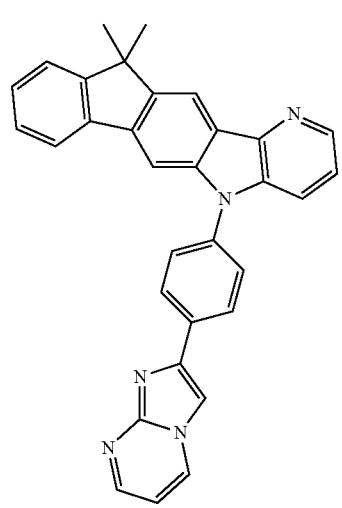
17
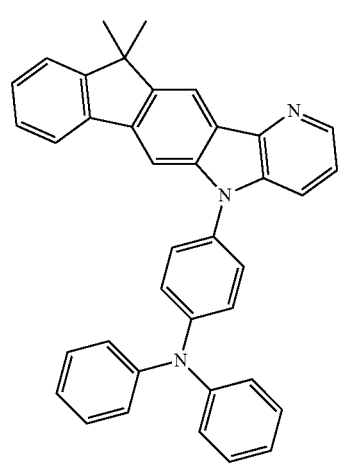

-continued
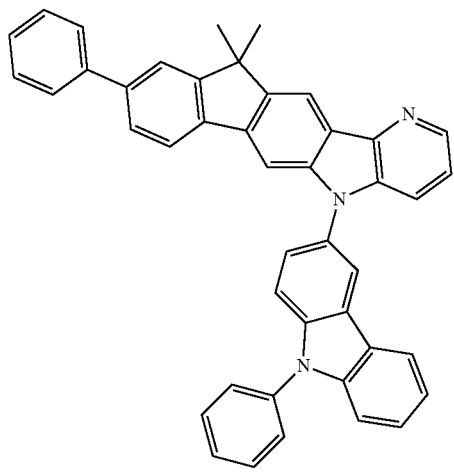
18
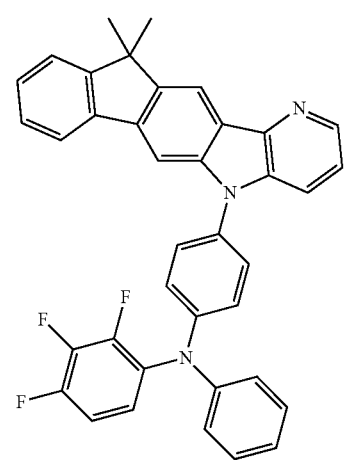
19
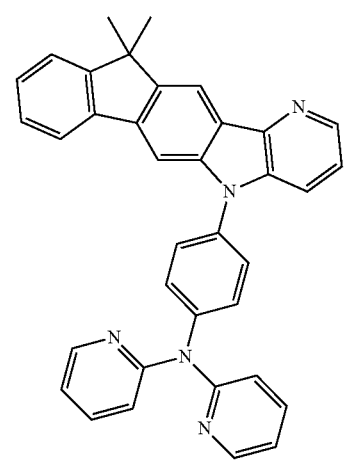
20
-continued
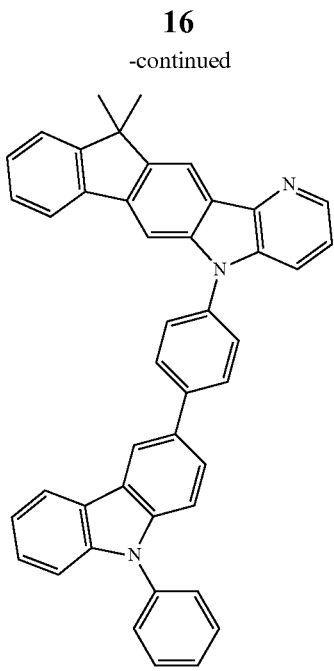
21
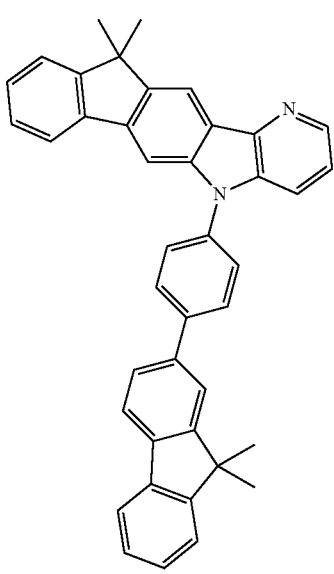
22
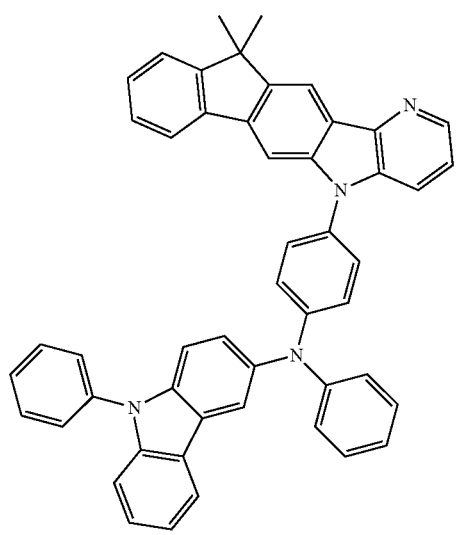
23

24
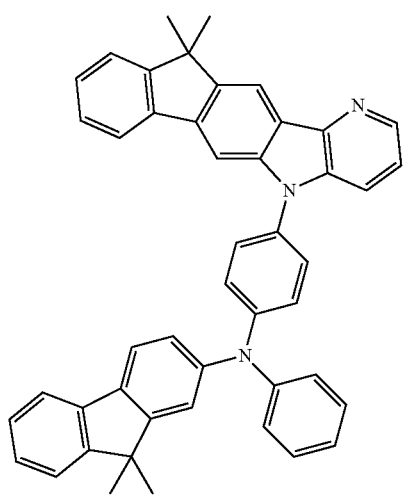
25
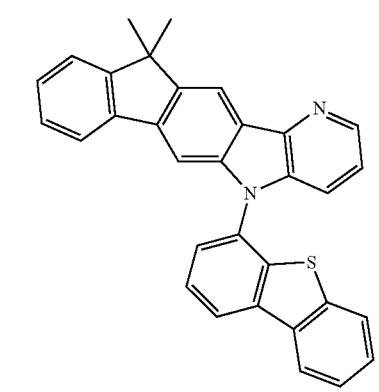
26
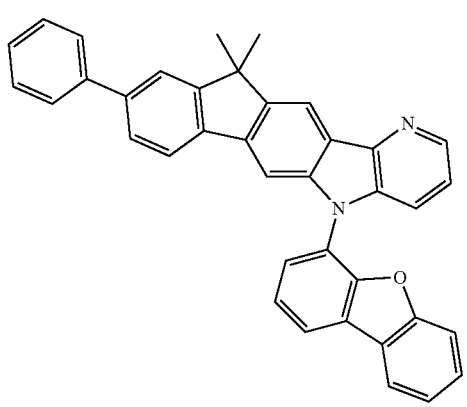
27
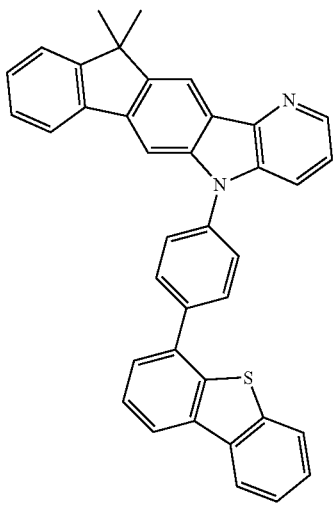
28
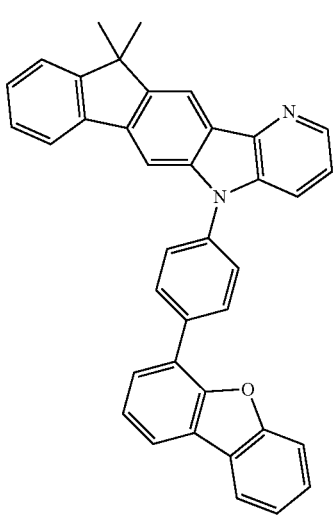
29
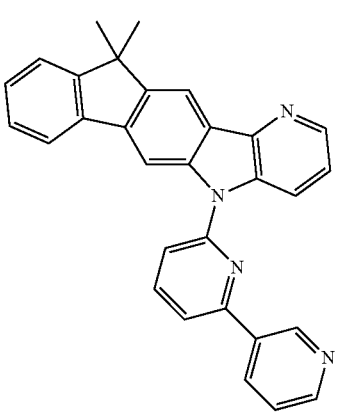

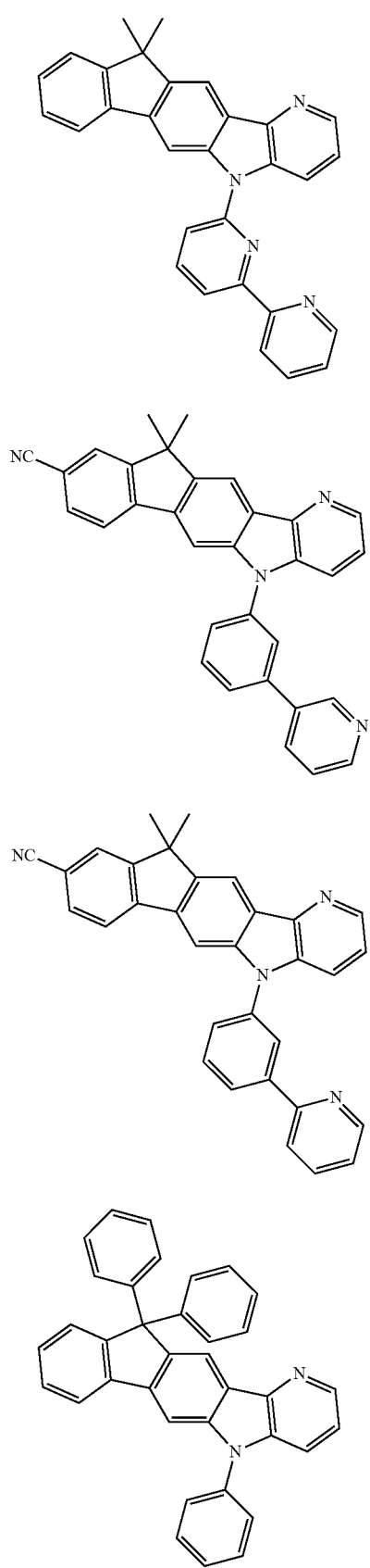
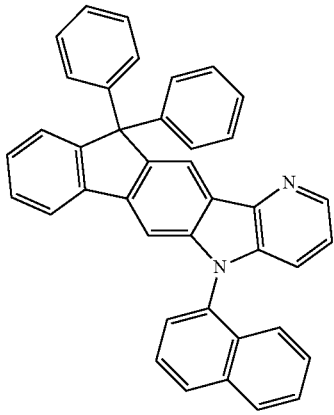
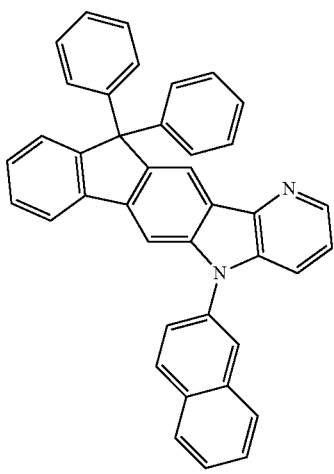
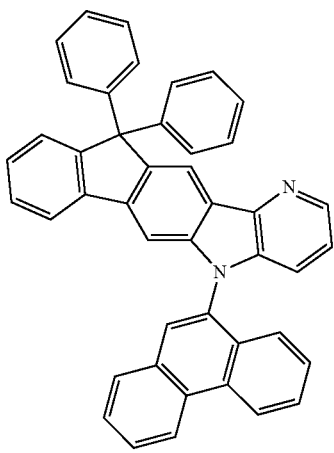

37
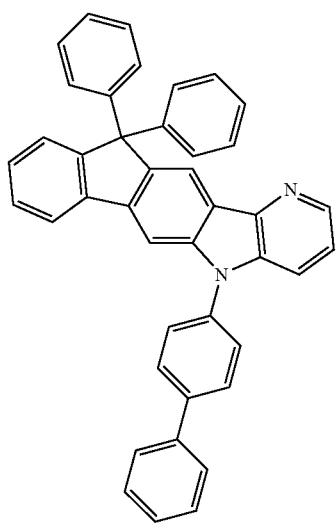
38
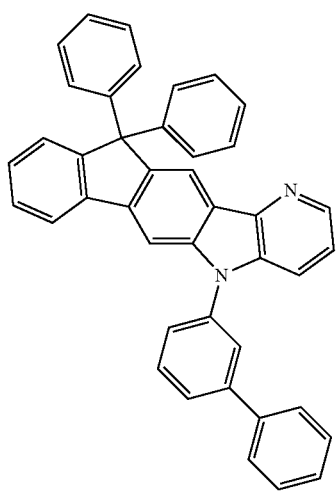
39
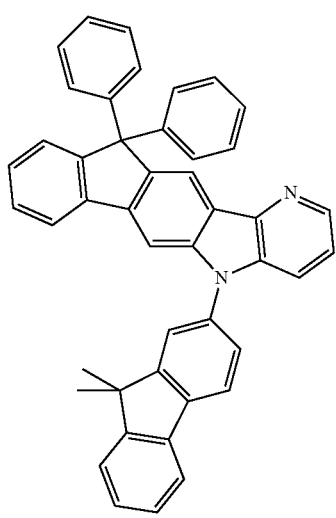
40
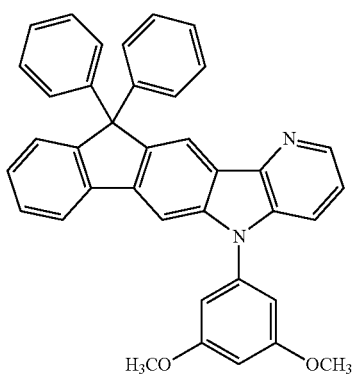
41
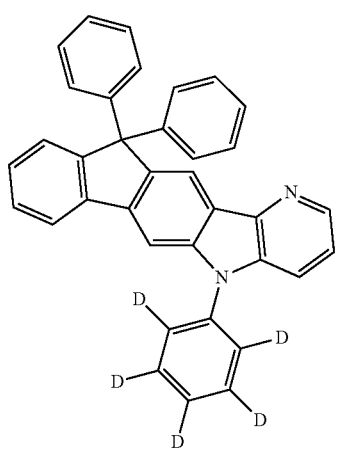
42
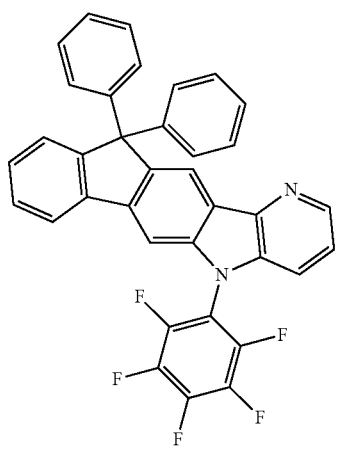

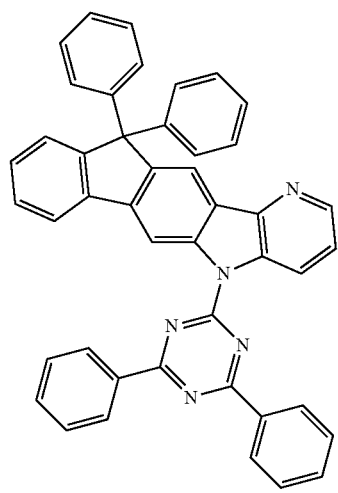
43
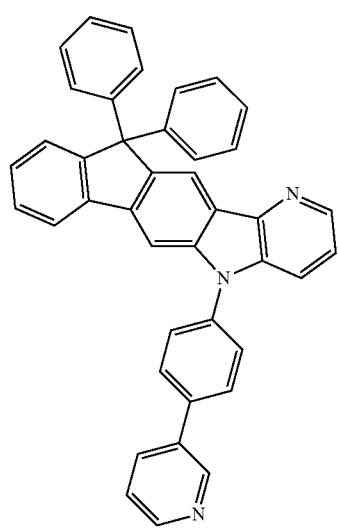
44
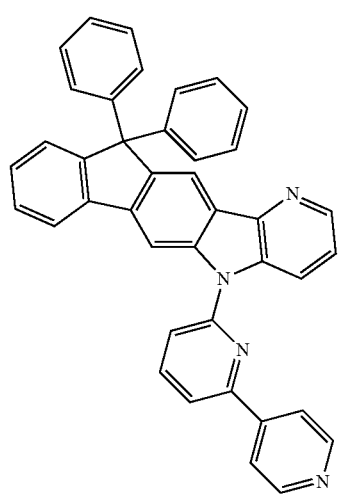
45
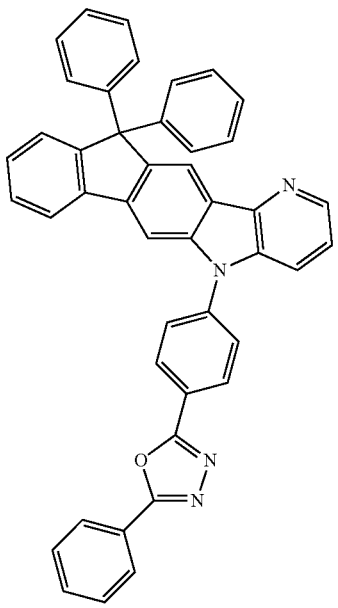
46
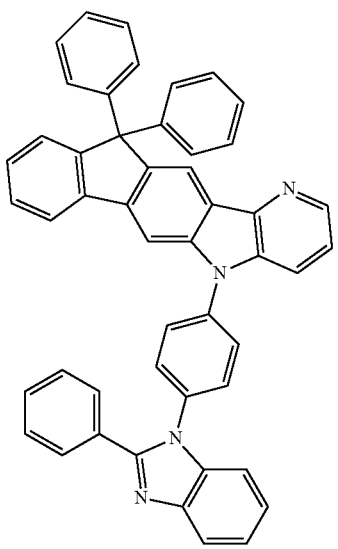
47

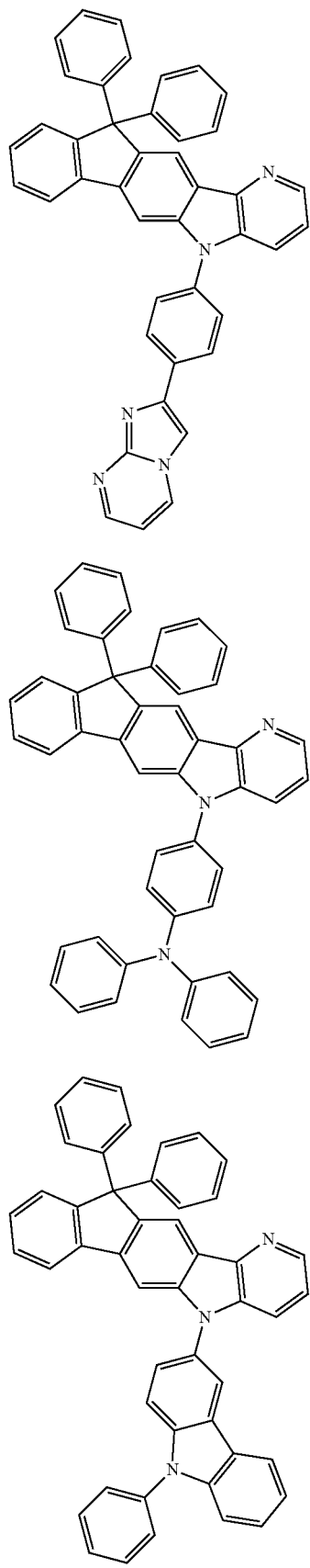
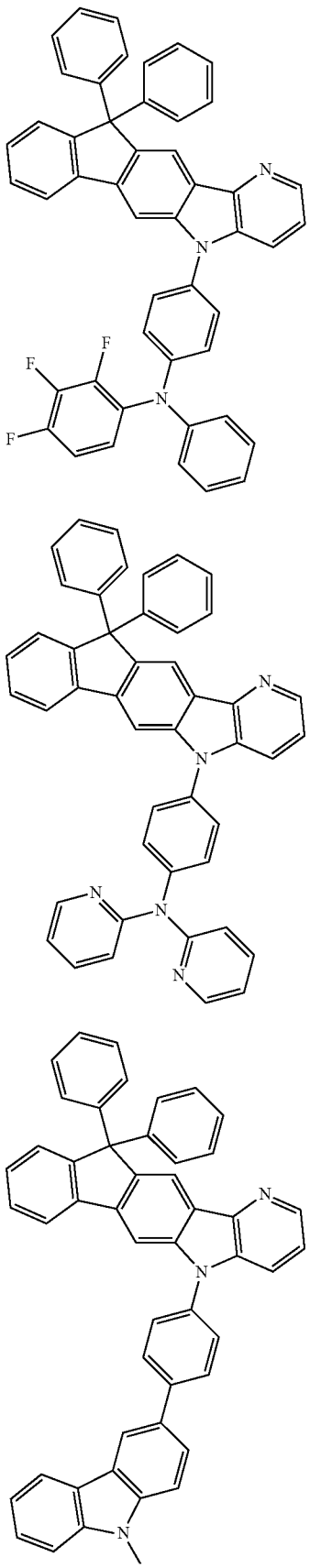

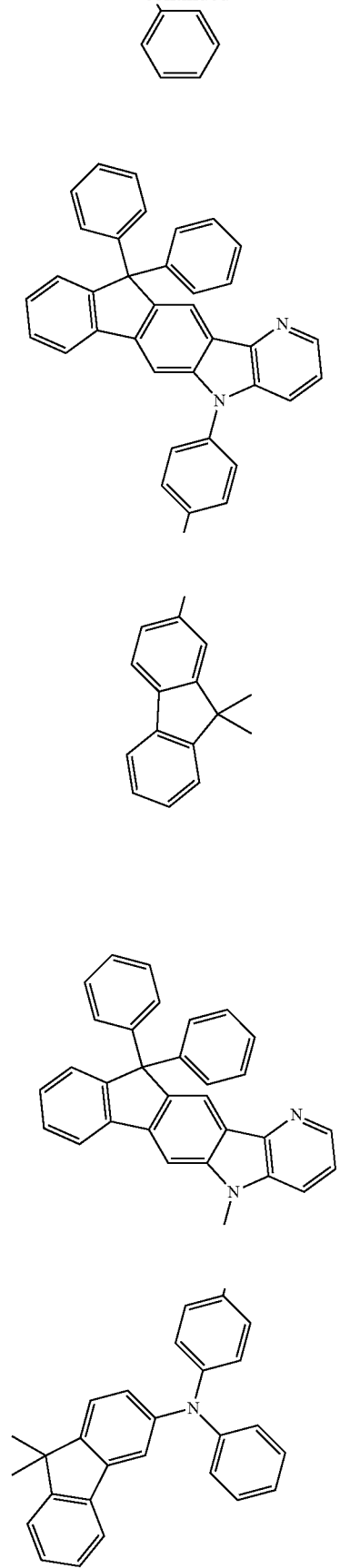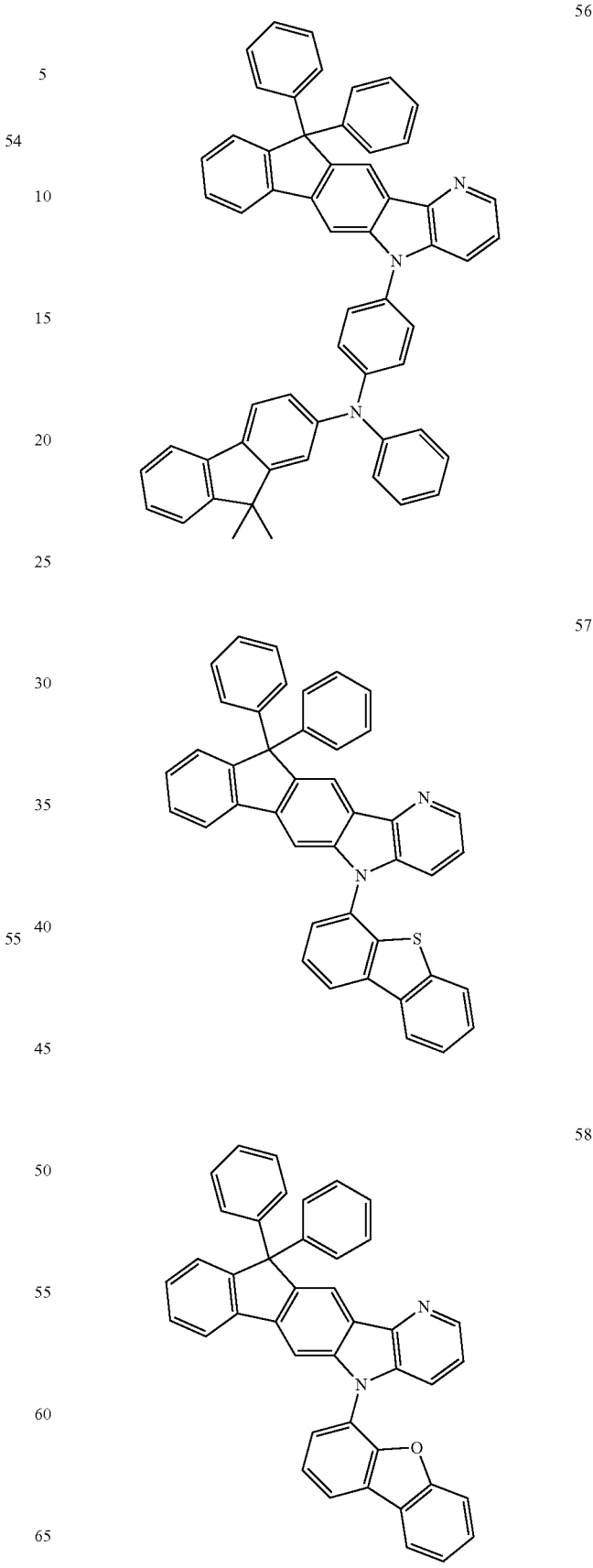

59
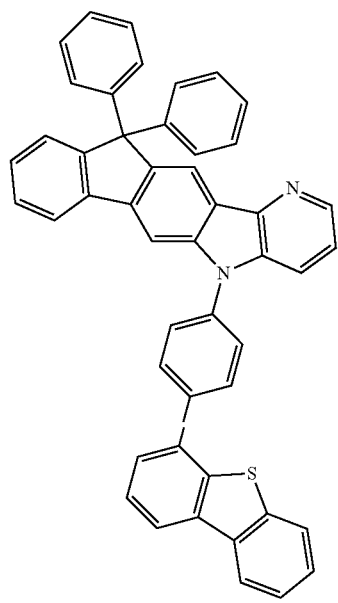
60
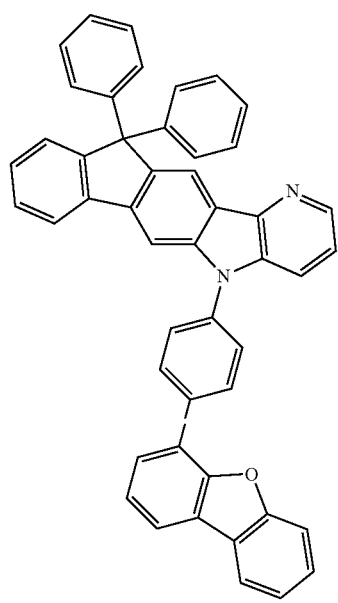
61
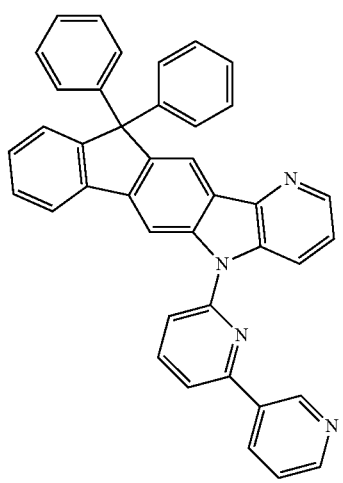
62
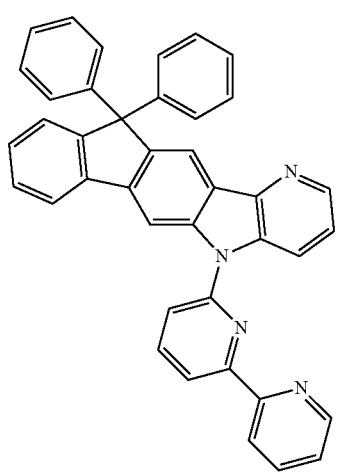
63
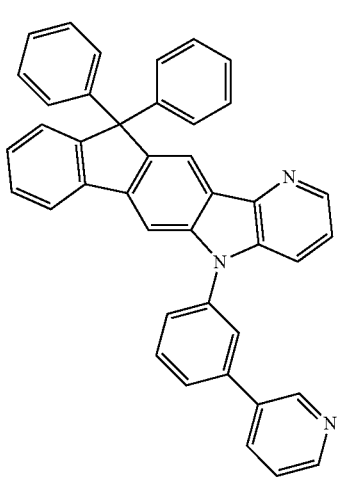
64
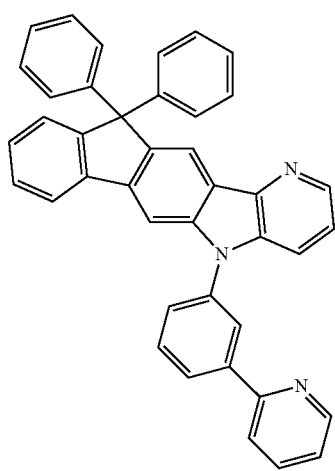

65
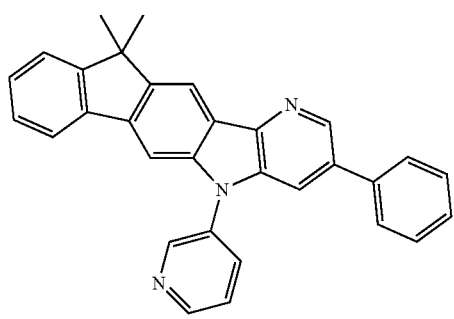
66
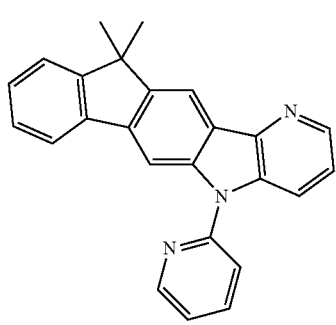
67
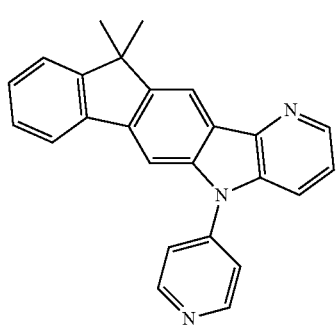
68
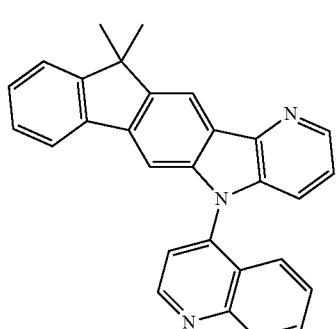
69
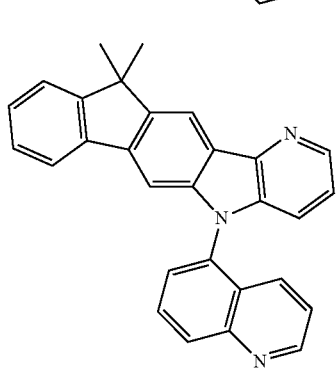
70
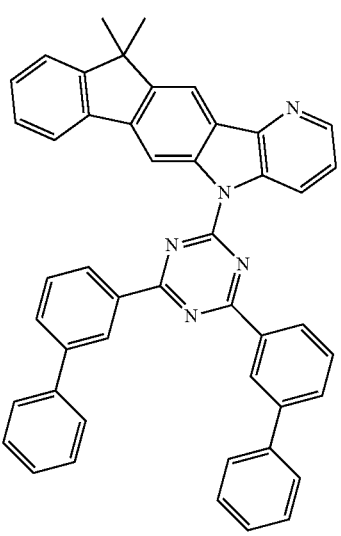
71
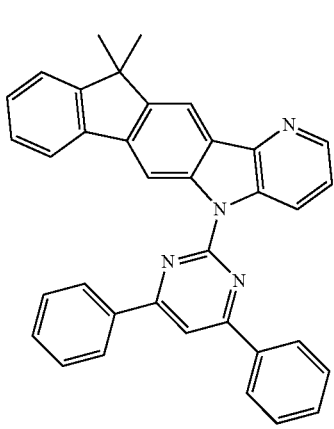
72
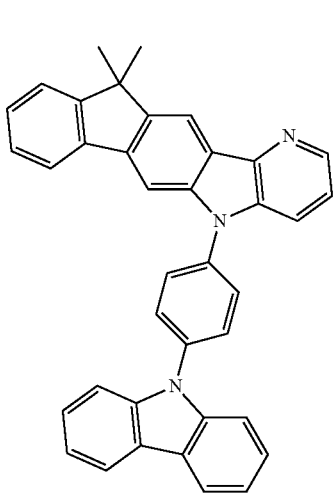

-continued
73
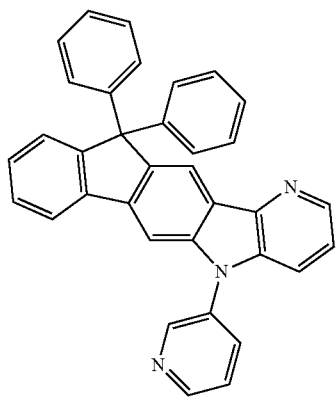
74
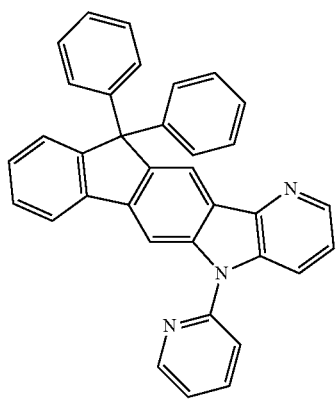
75
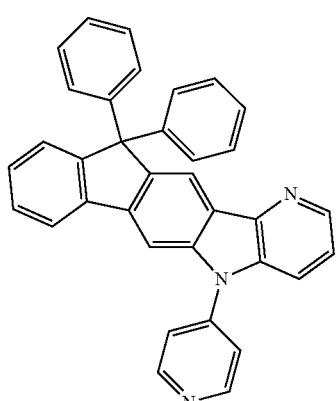
76
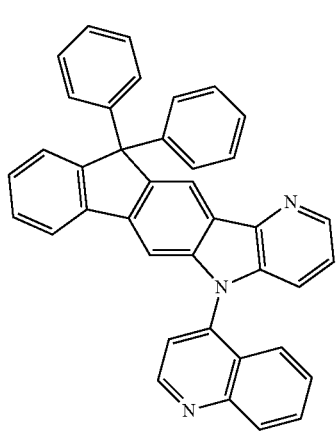
-continued
77
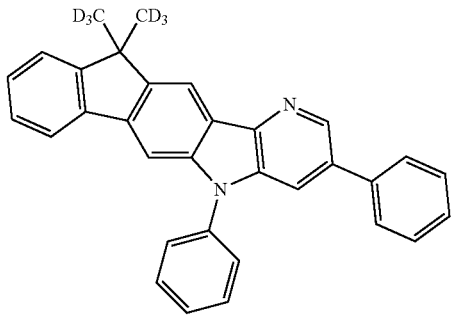
78
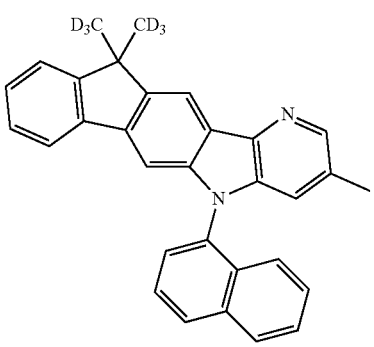
79
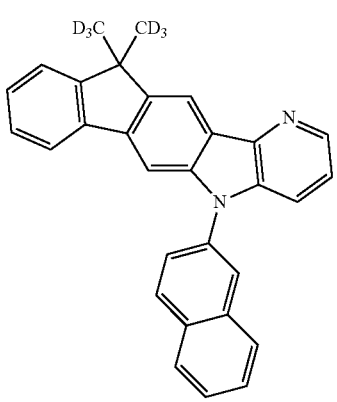
80
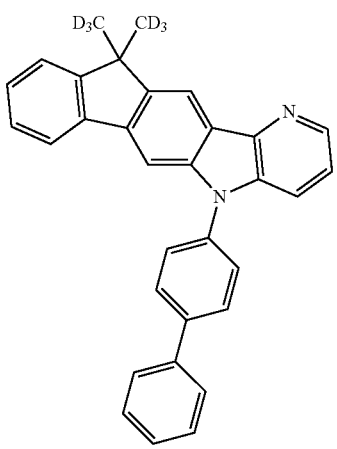

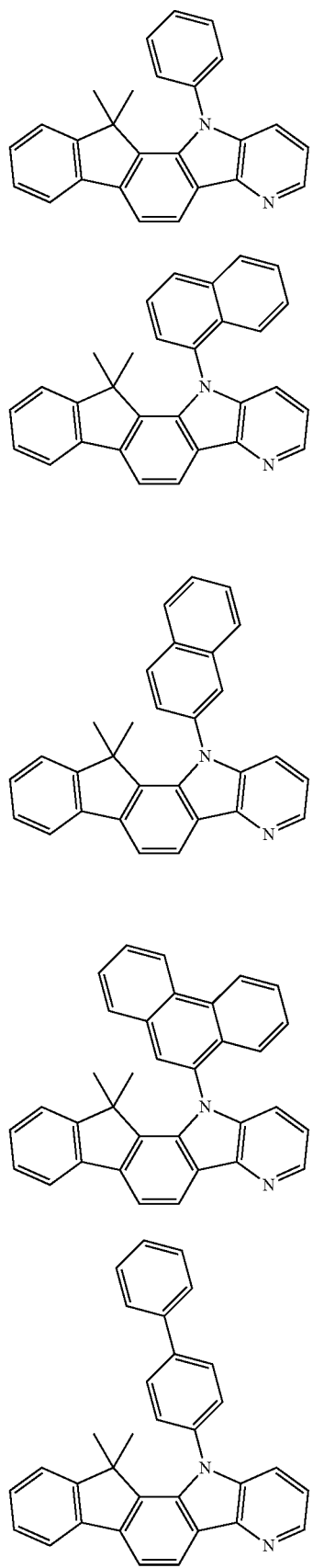
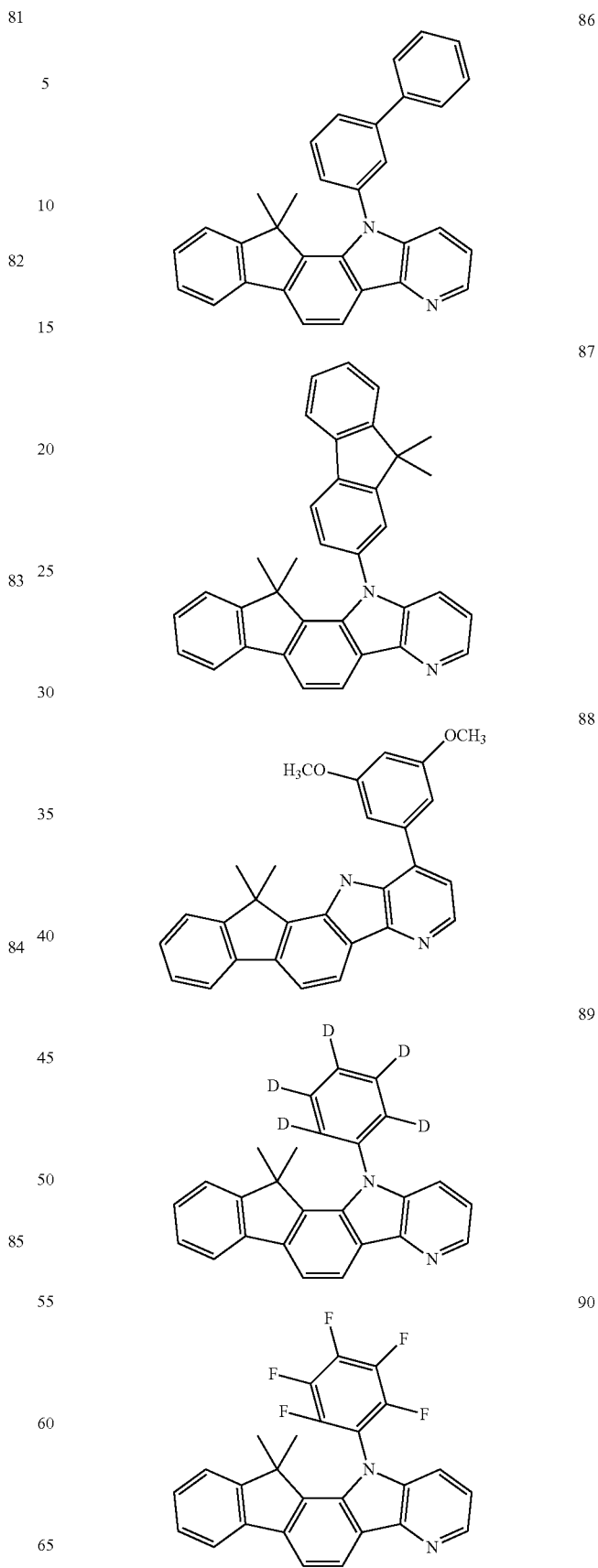

91
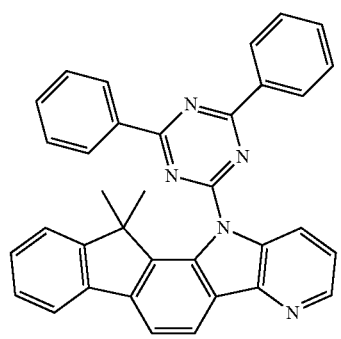
92
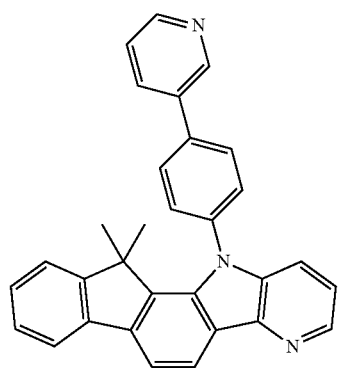
93
95
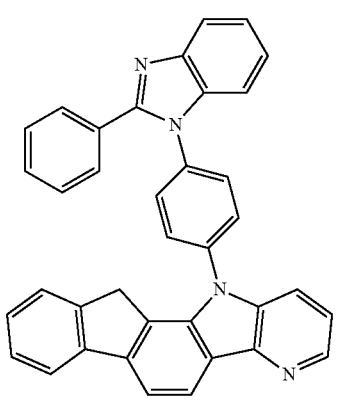
96
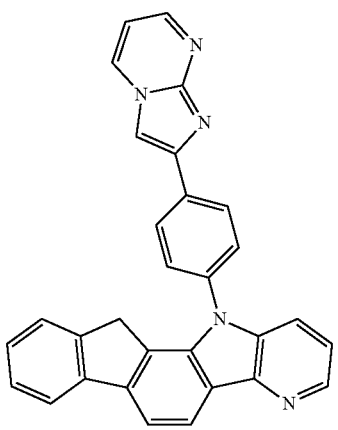
97
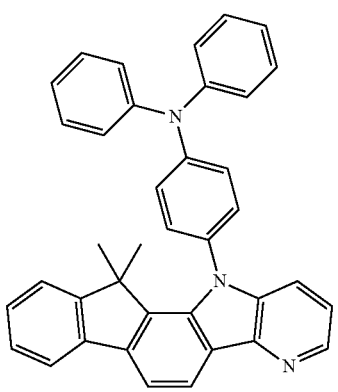
98
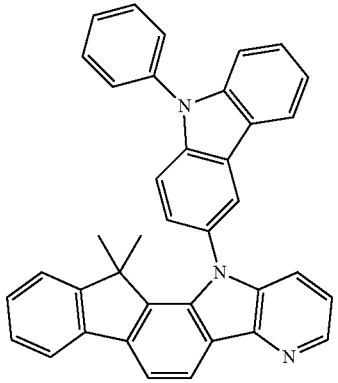

99
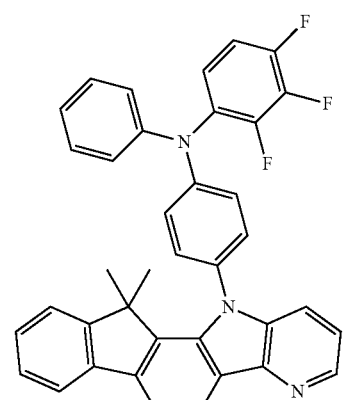
100
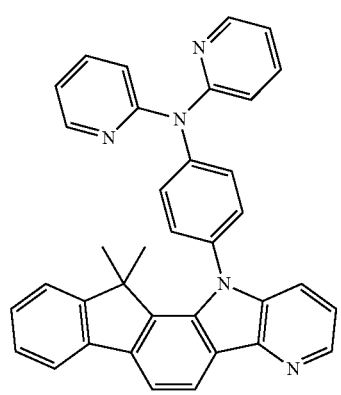
101
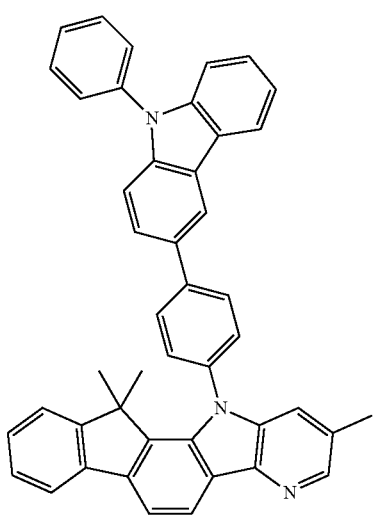
102
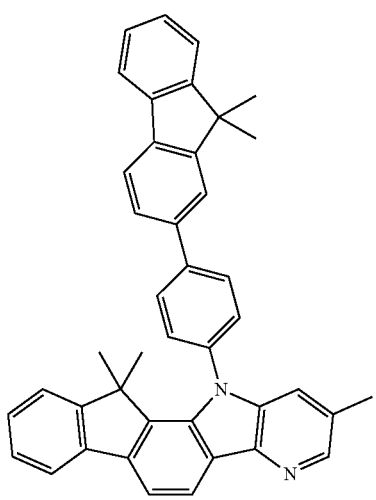
103
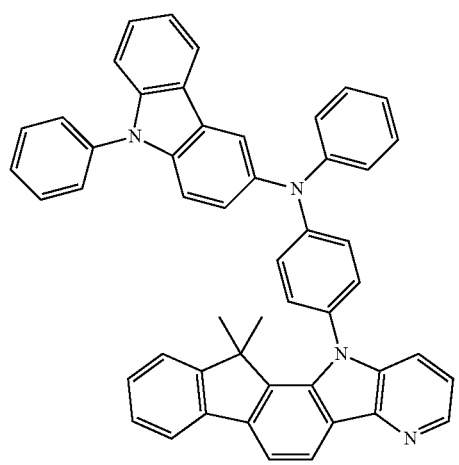
104
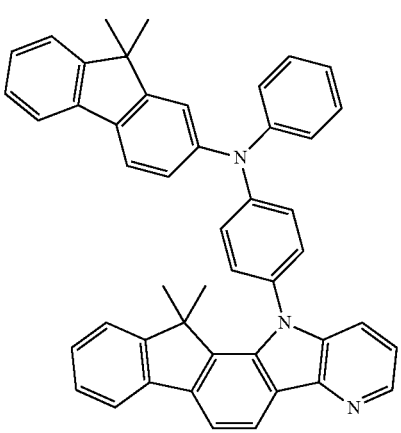

105 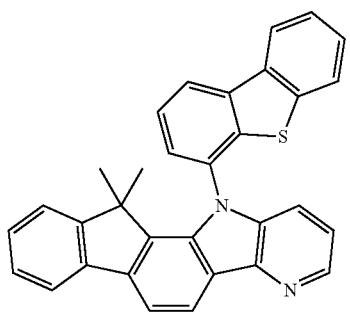

106 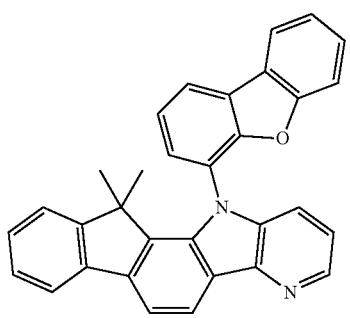

107 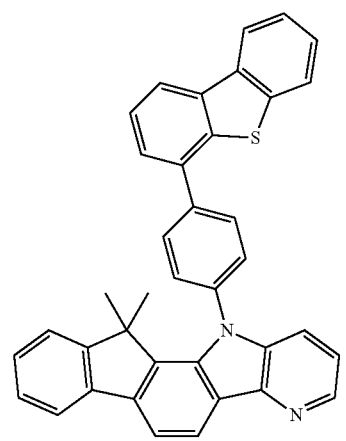

108 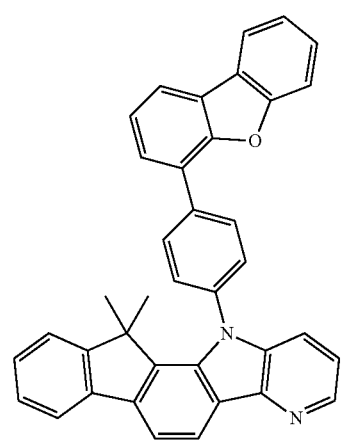

109 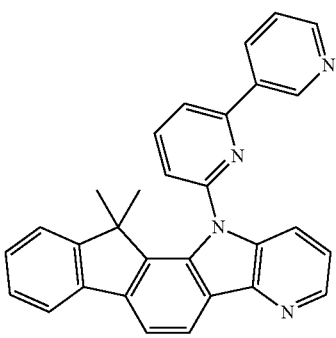

110 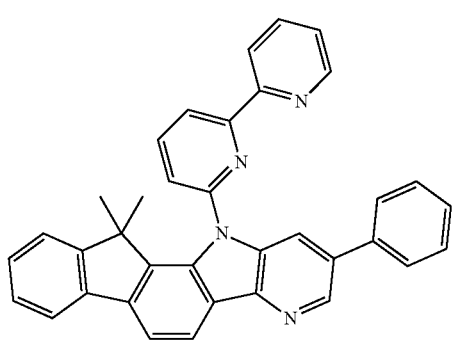

111 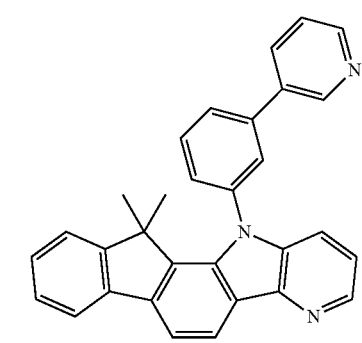

112 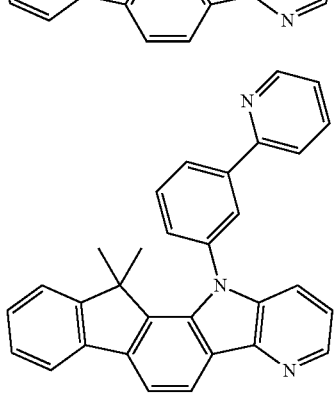

According to some example embodiments, an organic light-emitting device may include a first electrode, a second electrode facing the first electrode, and at least one first layer interposed between the first electrode and the second electrode, wherein the first layer includes one or more heterocyclic compounds described above.

According to some embodiments, the organic light-emitting device may further include one or more additional layers, including, a hole injection layer, a hole transport layer, a functional layer having a hole injection function and a hole transport function, an electron blocking layer, an emission layer, a hole blocking layer, an electron transport layer, an electron injection layer, a functional layer having an electron injection function and an electron transport function, or a combination of two or more thereof between the first electrode and the second electrode. According to some embodiments, at least one layer selected from the first layer and the one or more additional layers may be formed by using a wet process. According to some embodiments, the first layer may be an emission layer, an electron injection layer, an electron transport layer, or a functional layer having a hole injection function and a hole transport function.

According to some embodiments, the first layer may be an emission layer, one of the one or more heterocyclic compounds may be used as a fluorescent host or a phosphorescent host, and the first layer may further include a fluorescent dopant or a phosphorescent dopant.

According to some embodiments, the phosphorescent dopant may include an organometallic complex including Ir, Pt, Os, Re, Ti, Zr, Hf, or a combination of two or more thereof.

According to some embodiments, the first layer may be an emission layer, one of the one or more heterocyclic compounds may be used as a fluorescent dopant, and the first layer may further include a fluorescent host or a phosphorescent host. According to some embodiments, the fluorescent host or the phosphorescent host may include another one of the one or more heterocyclic compounds, wherein the another one of the one or more heterocyclic compounds is different from the fluorescent dopant heterocyclic compound.

According to some embodiments, the first layer may be an emission layer, an electron transport layer, or a functional layer having a hole injection function and a hole transport function, and the first layer may further include at least one selected from an anthracene-based compound, an arylamine-based compound, and a styryl-based compound. At least one selected from the hole injection layer, the hole transport layer, and the functional layer having a hole injection function and a hole transport function may further include a charge generating material.

The first layer may be an electron transport layer or the one or more additional layers may be an electron transport layer. The electron transport layer may include an electron transport organic material and a metal-containing material. The first layer may be an electron transport layer, and an emission layer may be additionally interposed between the first electrode and the second electrode. The emission layer may include at least one region selected from a red emission region, a green emission region, a blue emission region, and a white emission region, and at least one region of the red emission region, the green emission region, the blue emission region, and the white emission region may include a phosphorescent compound.

According to some example embodiments, a flat display device may include a transistor that includes a source, a drain, a gate, and an active layer; and the organic light-emitting device described above, wherein any one of the source and the drain is electrically connected to the organic light-emitting device.

BRIEF DESCRIPTION OF THE DRAWINGS

The embodiments will become more apparent by describing in detail exemplary embodiments thereof with reference to FIG. 1 that is a schematic view of an organic light-emitting device according to an embodiment.

DETAILED DESCRIPTION

Korean Patent Application No. 10-2011-0043439, filed on May 9, 2011, in the Korean Intellectual Property Office, is incorporated herein by reference in its entirety by reference.

A heterocyclic compound according to an embodiment of the present invention is represented by Formula 1 or Formula 2 below:

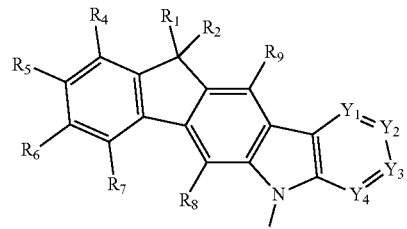

<Formula 1>

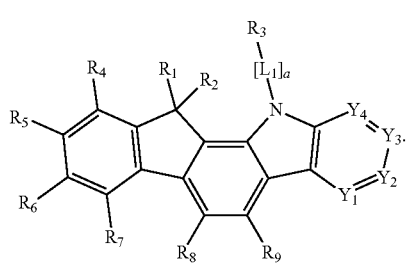

<Formula 2> wherein $Y_1$ to $Y_4$ are each independently N or $C(R_{10})$, and one or more of $Y_1$ to $Y_4$ are N, and when two or more of $Y_1$ to $Y_4$ are $C(R_{10})$, a plurality of $R_{10}$ may be identical to or different from each other, $R_1$ to $R_{10}$ are each independently a hydrogen atom, a deuterium atom, a halogen atom, a hydroxyl group, a cyano group, a nitro group, a carboxylic group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ heteroaryl group, or a group represented by $N(Q_1)(Q_2)$ where $Q_1$ and $Q_2$ are each independently a hydrogen atom, a deuterium atom, a halogen atom, a hydroxyl group, a cyano group, an amino group, a nitro group, a carboxylic group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ heteroaryl group, $L_1$ is a substituted or unsubstituted $C_6$-$C_{30}$ arylene group or a substituted or unsubstituted $C_3$-$C_{30}$ heteroarylene group, and a is an integer from 1 to 3.

According to some embodiments, $Y_1$ is N and $Y_2$, $Y_3$ and $Y_4$ are each $C(R_{10})$.

For example, $R_1$ to $R_{10}$ are each independently a hydrogen atom, a deuterium atom, a halogen atom, a hydroxyl group, a cyano group, a nitro group, a carboxylic group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted methoxy group, a substituted or unsubstituted ethoxy group, a substituted or unsubstituted phenyl group, a substituted or unsubstituted biphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted phenanthridinyl group, a substituted or unsubstituted phenanthrolinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyridoindolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted carbazolyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted benzooxazolyl group, a substituted or unsubstituted isooxazolyl group, a substituted or unsubstituted oxadiazolyl group, a substituted or unsubstituted triazolyl group, a substituted or unsubstituted triazinyl group, a substituted or unsubstituted tetrazolyl group, or a group represented by $N(Q_1)(Q_2)$ where $Q_1$ and $Q_2$ are each independently a hydrogen atom, a deuterium atom, a halogen atom, a hydroxyl group, a cyano group, an amino group, a nitro group, a carboxylic group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyridinyl group, but are not limited thereto.

For example, $R_1$ to $R_{10}$ are each independently a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted imidazolyl group, a substituted or unsubstituted benzoimidazolyl group, a substituted or unsubstituted pyridinyl group, a substituted or unsubstituted quinolinyl group, a substituted or unsubstituted pyrimidinyl group, a substituted or unsubstituted imidazopyrimidinyl group, a substituted or unsubstituted indolyl group, a substituted or unsubstituted pyridoindolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxadiazolyl group, a substituted or unsubstituted triazinyl group, or a group represented by $N(Q_1)(Q_2)$ where $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group.

For example, $R_3$ is a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted imidazolyl group, a substituted or unsubstituted benzoimidazolyl group, a substituted or unsubstituted pyridinyl group, a substituted or unsubstituted pyrimidinyl group, a substituted or unsubstituted quinolinyl group, a substituted or unsubstituted imidazopyrimidinyl group, a substituted or unsubstituted indolyl group, a substituted or unsubstituted pyridoindolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxadiazolyl group, a substituted or unsubstituted triazinyl group, or a group represented by $N(Q_1)(Q_2)$ where $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group. In this case, $R_1$, $R_2$, and $R_4$ to $R_{10}$ are each independently a hydrogen atom, a deuterium atom, a halogen atom, a cyano group, a substituted or unsubstituted methyl group, or a substituted or unsubstituted phenyl group.

Detailed examples of $R_3$ are a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, and groups represented by Formulae 2A to 2S below, and $R_1$, $R_2$, $R_4$ to $R_{10}$ are each independently a hydrogen atom, a deuterium atom, a halogen atom, a cyano group, a substituted or unsubstituted methyl group, or a substituted or unsubstituted phenyl group:

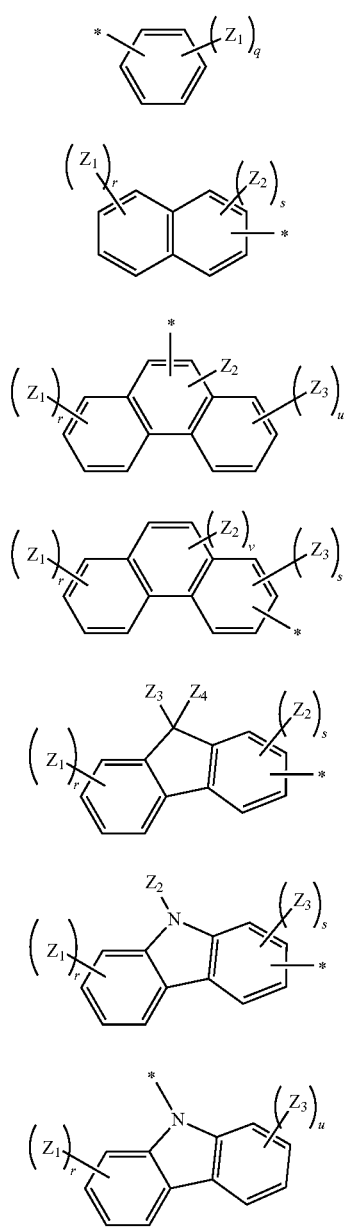

<Formula 2A>

<Formula 2B>

<Formula 2C>

<Formula 2D>

<Formula 2E>

<Formula 2F>

<Formula 2G>

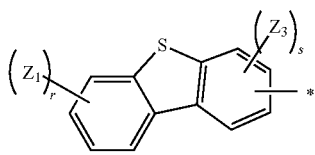

<Formula 2H>

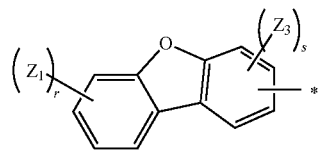

<Formula 2I>

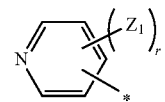

<Formula 2J>

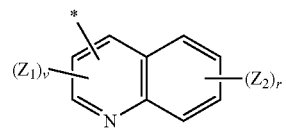

<Formula 2K>

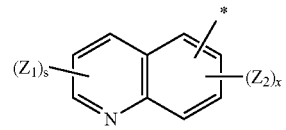

<Formula 2L>

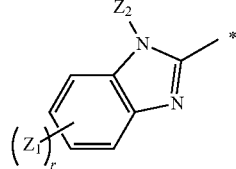

<Formula 2M>

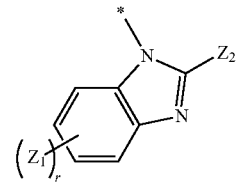

<Formula 2N>

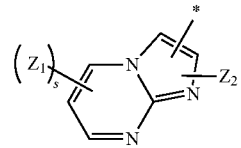

<Formula 2O>

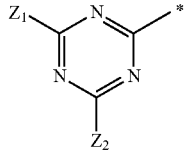

<Formula 2P>

<Formula 2Q>

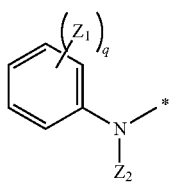

<Formula 2R>

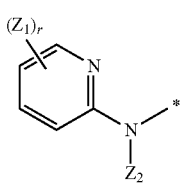

<Formula 2S>

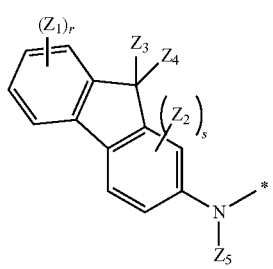

wherein $Z_1$, $Z_2$, $Z_3$, $Z_4$ and $Z_5$ are each independently a hydrogen atom, a deuterium atom, a halogen atom, a hydroxyl group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted biphenyl group, a substituted or unsubstituted pyridinyl group, a substituted or unsubstituted naphthyl group, or a substituted or unsubstituted anthryl group, a plurality of $Z_1$, $Z_2$, $Z_3$, $Z_4$, and $Z_5$ are identical to or different from each other, q is an integer from 1 to 5, r and u are each independently an integer from 1 to 4, s and x are each independently an integer from 1 to 3, v is an integer from 1 to 2, and * represents a binding site.

Further detailed examples of $R_3$ are a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, and groups represented by Formulae 3A to 3P below, and $R_1$, $R_2$, and $R_4$ to $R_{10}$ are each independently a hydrogen atom, a deuterium atom, a halogen atom, a cyano group, a substituted or unsubstituted methyl group, or a substituted or unsubstituted phenyl group:

<Formula 3A>

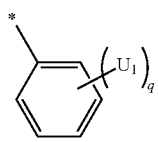

<Formula 3B>

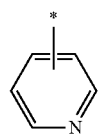

<Formula 3C>

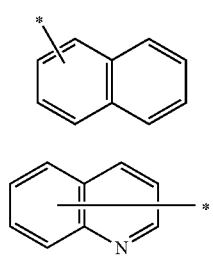

<Formula 3D>

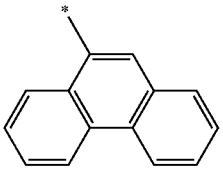

<Formula 3E>

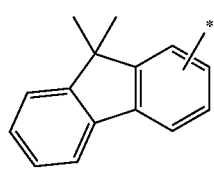

<Formula 3F>

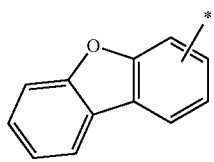

<Formula 3G>

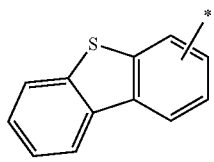

<Formula 3H>

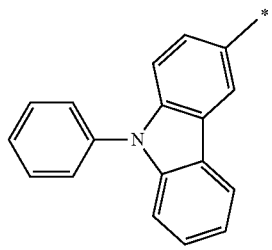

<Formula 3I>

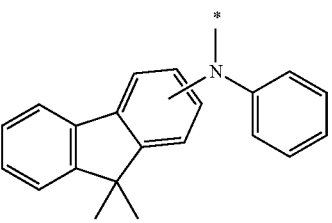

<Formula 3J>

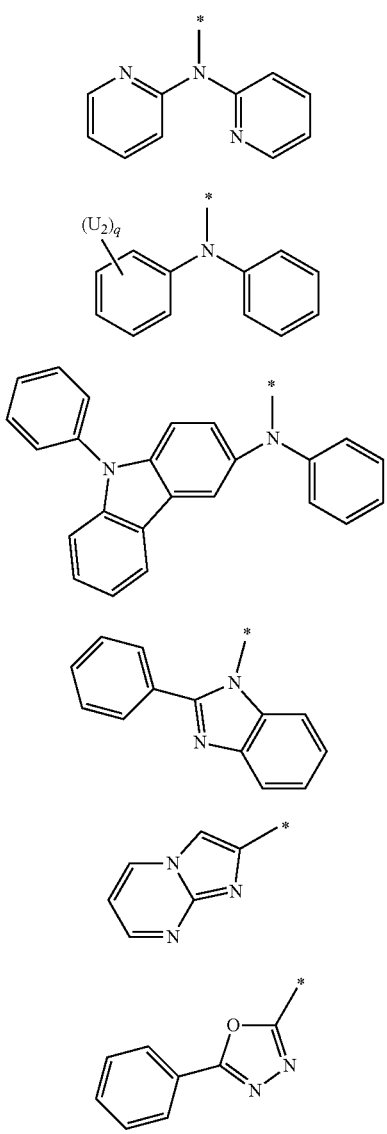

<Formula 3K>

<Formula 3L>

<Formula 3M,>

<Formula 3N>

<Formula 3O>

<Formula 3P> wherein $U_1$ is a hydrogen atom, a deuterium atom, a halogen atom, or a methoxy group, $U_2$ is a hydrogen atom or a halogen atom, a plurality of $U_1$ and $U_2$ may be identical to or different from each other, q is an integer of 1 to 5, and * represents a binding site.

In Formula 1 or Formula 2, $L_1$ is a substituted or unsubstituted phenylene group, a substituted or unsubstituted naphthylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted pherylenylene group, a substituted or unsubstituted fluorenylene group, a substituted or unsubstituted spiro-fluorenylene group, a substituted or unsubstituted carbazolylene group, a substituted or unsubstituted pyridinylene group, a substituted or unsubstituted benzoimidazolene group, a substituted or unsubstituted imidazopyrimidinylene group, or a substituted or unsubstituted oxadiazolylene group.

An example of $L_1$ may be a compound having a formula selected from groups represented by Formulae 4A to 4F below, but is not limited thereto:

<Formula 4A>

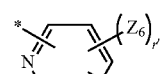
<Formula 4B>

<Formula 4C>

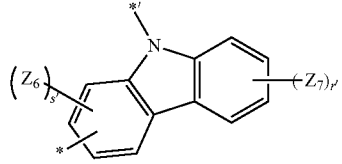

<Formula 4D>

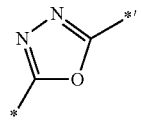

<Formula 4E>

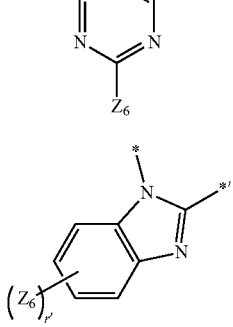

<Formula 4F> wherein $Z_6$ is a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted methoxy group, or a substituted or unsubstituted phenyl group, a plurality of $Z_6$ may be identical to or different from each other, r' is an integer from 1 to 4, s' is an integer from 1 to 3, and * and *' each indicate a binding site. In this case, * indicates a site connected to either N of indole or $L_1$ near the N of indole, and *' indicates a site connected to either $R_3$ or $L_1$ opposite to the N of indole.

In Formula 1 or Formula 2, $L_1$, which is a bivalent linker, may not exist. If $L_1$ does not exist, in Formula 1 or Formula 2, a is 0. If one $L_1$ exists, a is 1, and if two $L_1$ exist in series, a is 2.

Compounds represented by Formula 1 or Formula 2 may be used as a light-emitting material and/or electron transport material for an organic light-emitting device. Also, compounds represented by Formula 1 or Formula 2 having a heterocycle in their molecules may have high glass transition temperature (Tg) or melting point, due to the introduction of a heterocycle. Accordingly, during electroluminescence, heat resistance against joule's heat (generated in an organic layer, between organic layers, and between an organic layer and a metal electrode), and durability (under high-temperature conditions), may be increased. Also, a heterocyclic compound represented by Formula 1 or Formula 2 may exhibit high durability during preservation and driving of an organic light-emitting device, due to inclusion of a pyridoindole structure in its molecule. Also, if a substituent, such as a fluorene group is introduced to a heterocyclic compound represented by Formula 1 or Formula 2, morphology of an organic layer may be improved, and thus, an organic light-emitting device, including, such heterocyclic compounds may have improved characteristics.

The heterocyclic compound may be any one of compounds 1 to 112 below, but is not limited thereto:

1

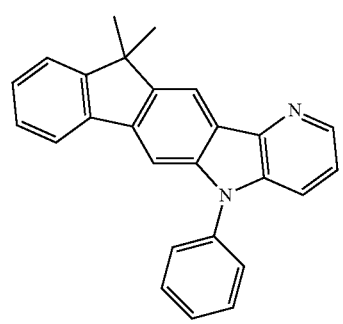

2

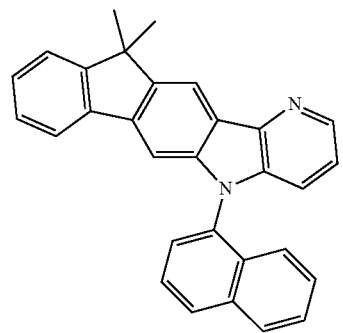

3

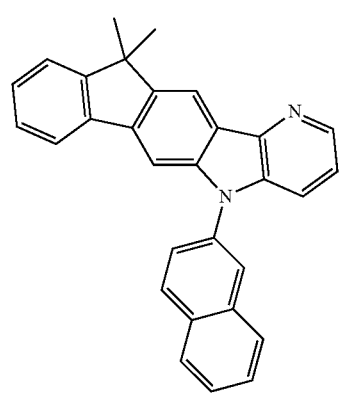

-continued

4

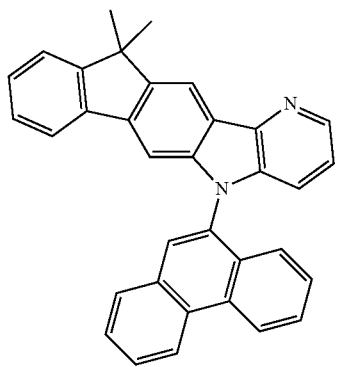

5

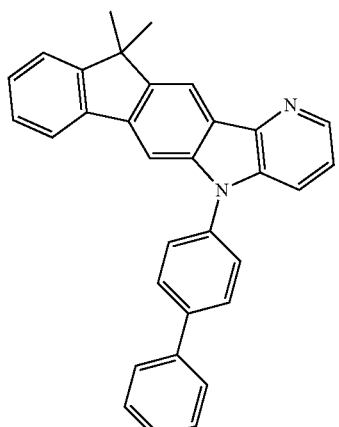

6

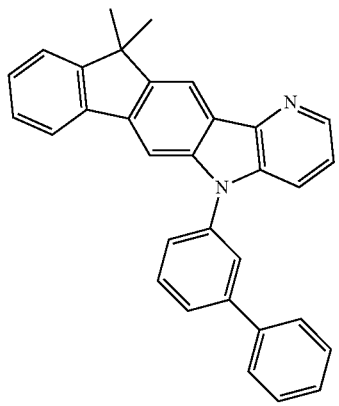

7

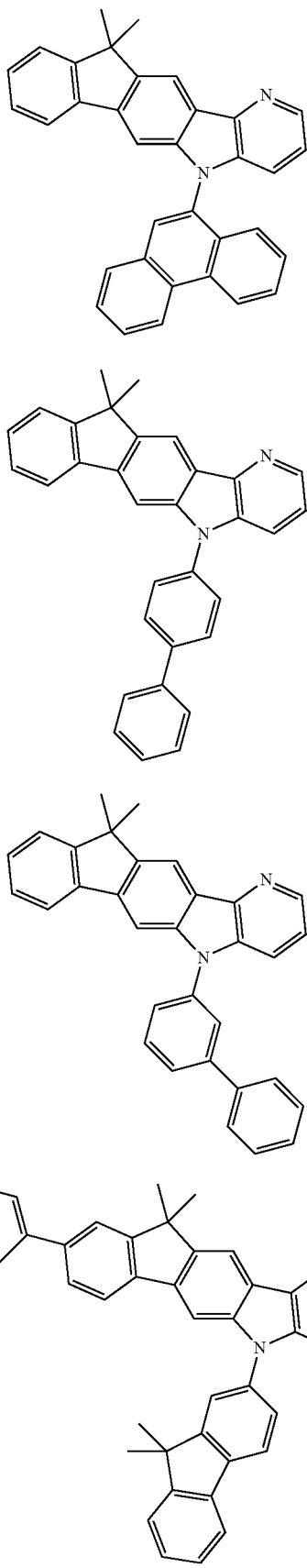

8
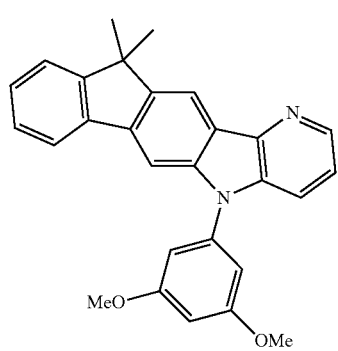
9
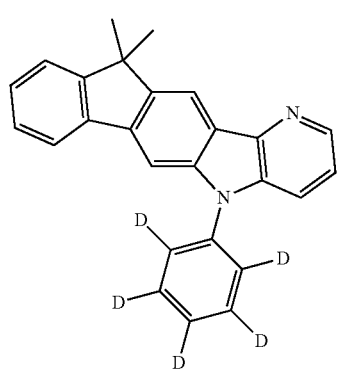
10
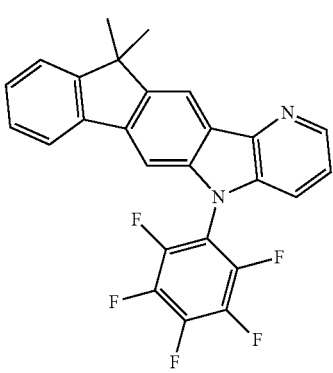
11
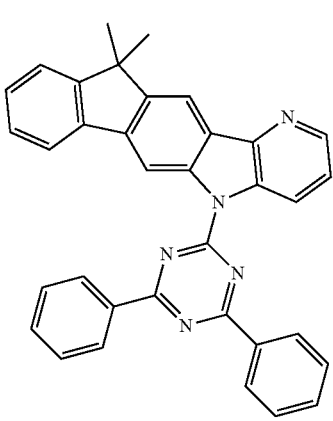
12
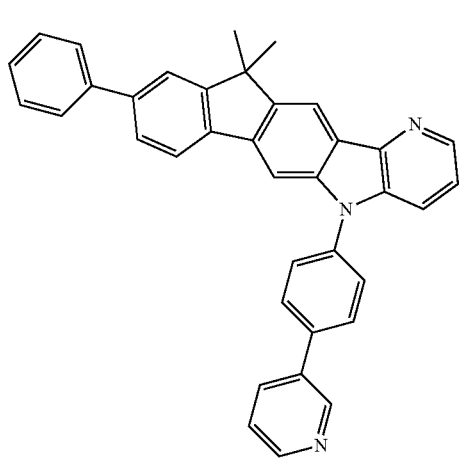
13
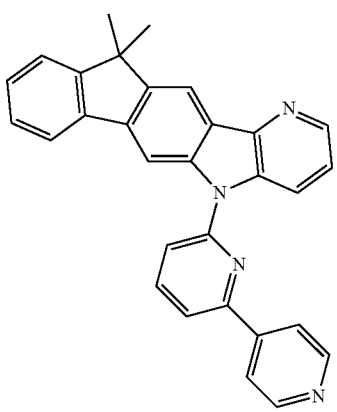
14
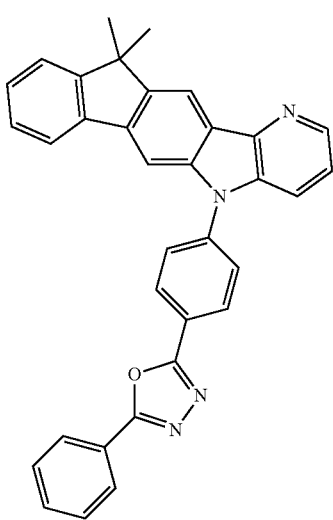

15
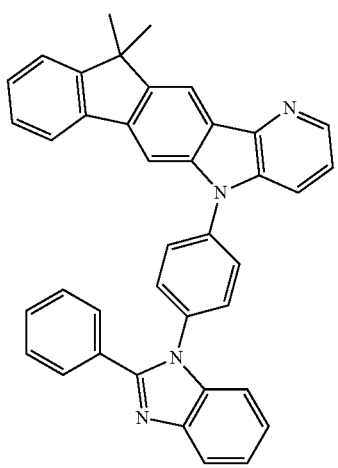
18
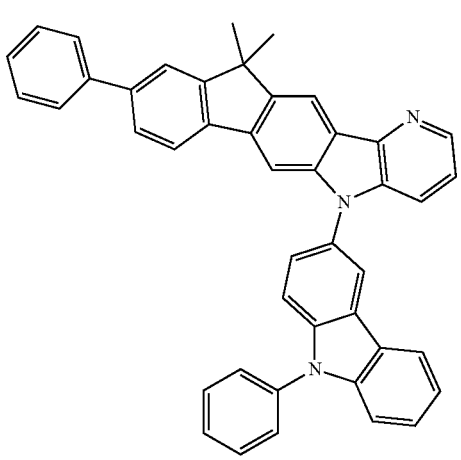
16
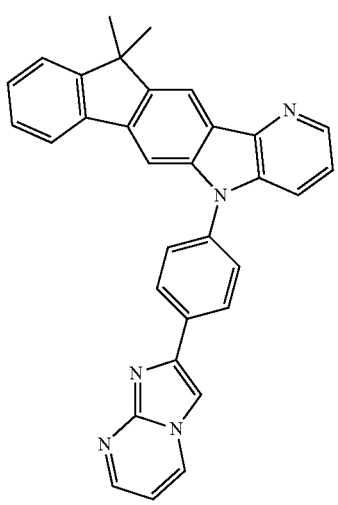
19
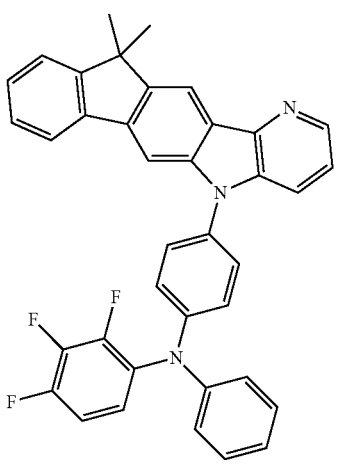
17
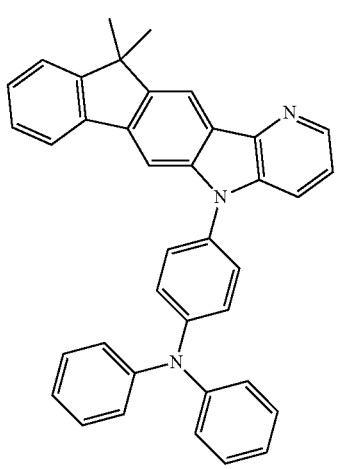
20
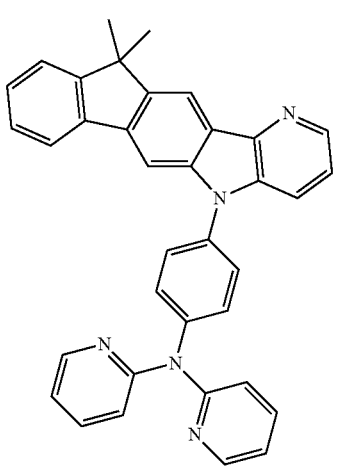

21
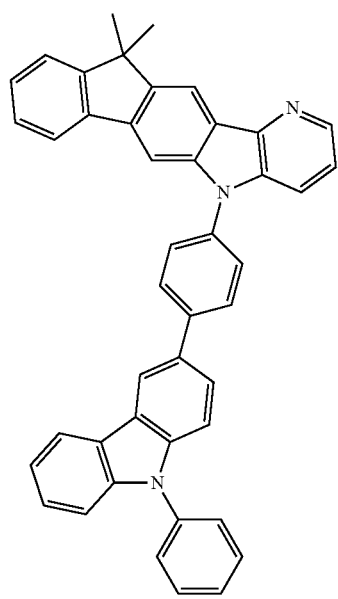
22
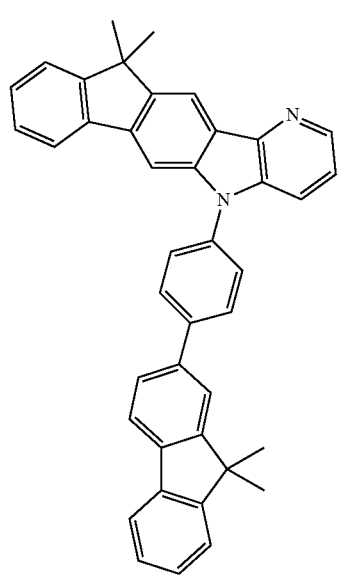
23
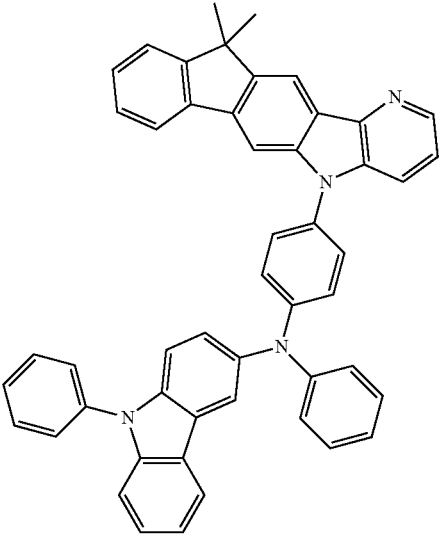
24
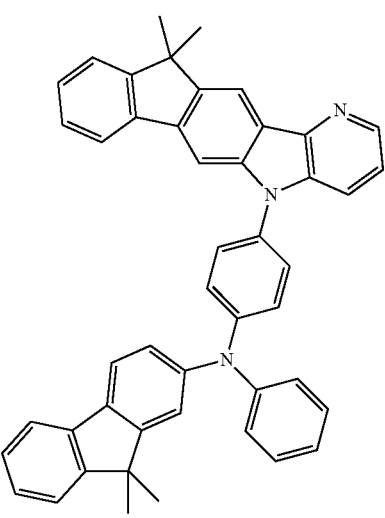
25
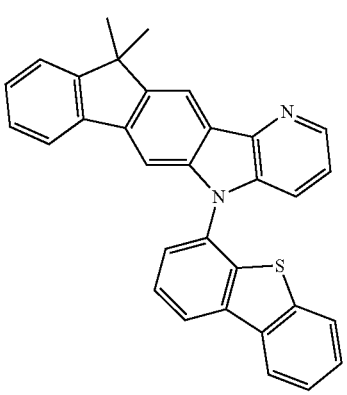

26
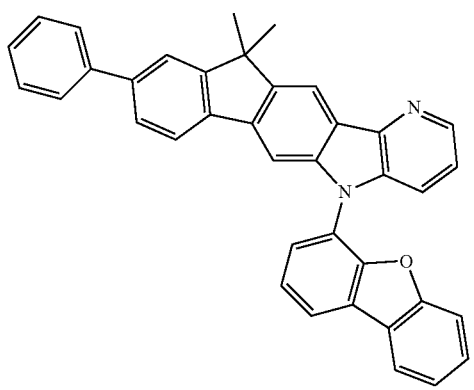
27
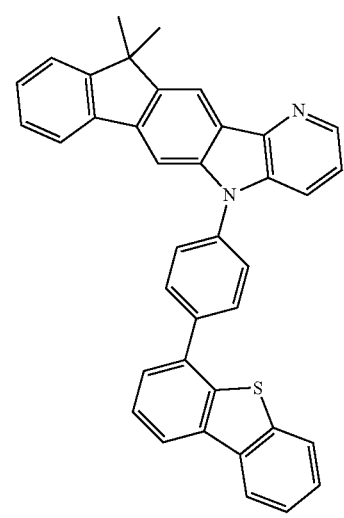
28
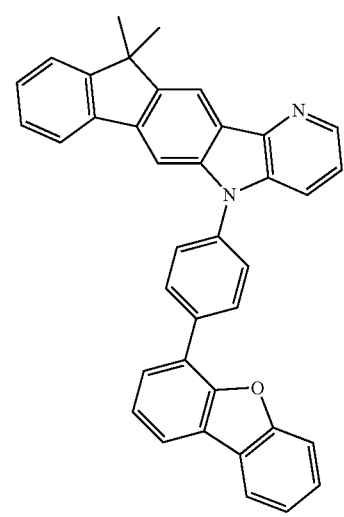
29
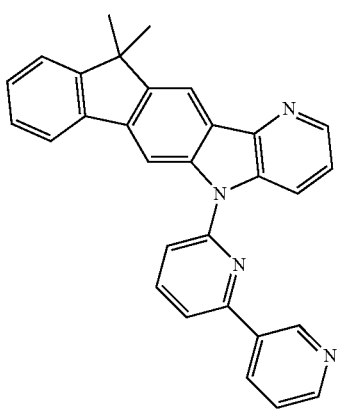
30
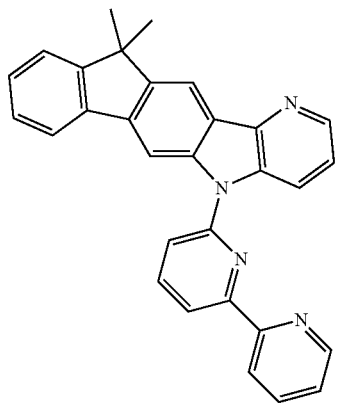
31
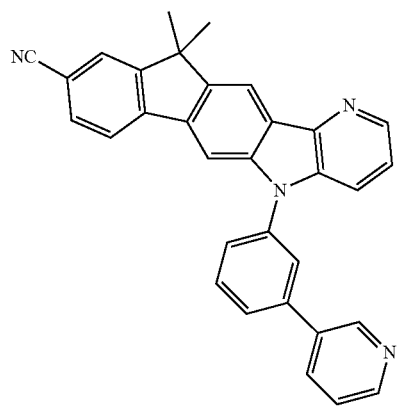
32
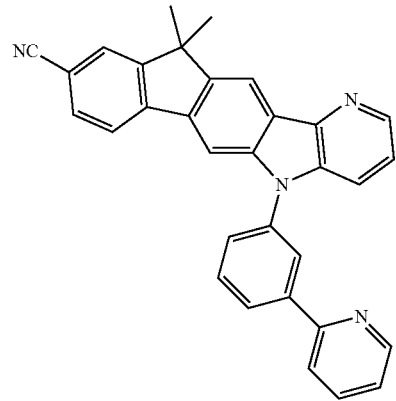

33
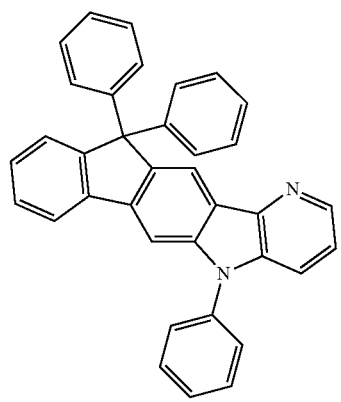
34
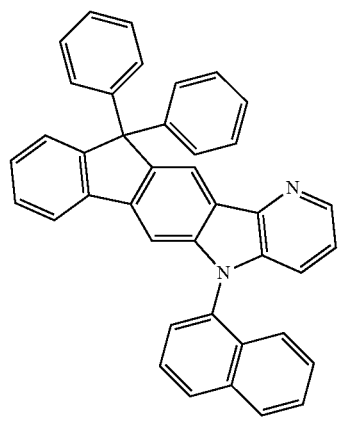
35
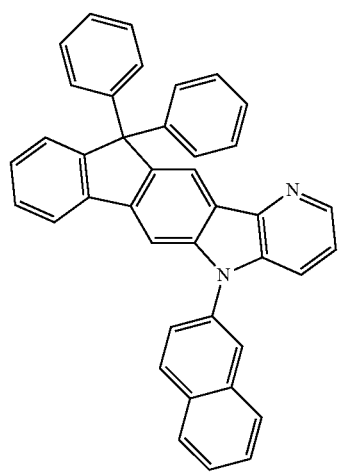
36
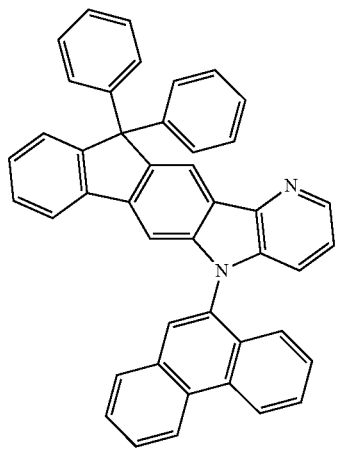
37
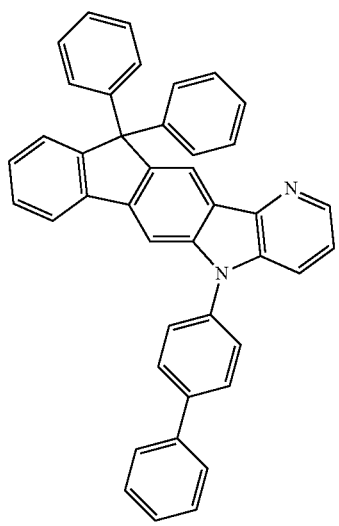
38
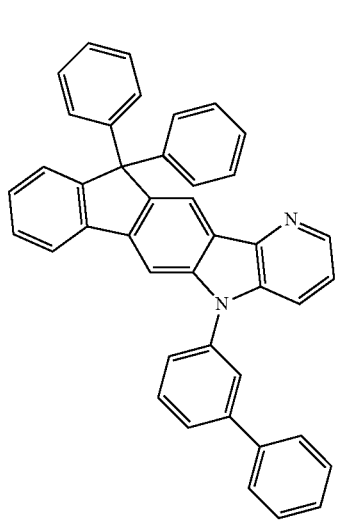

39
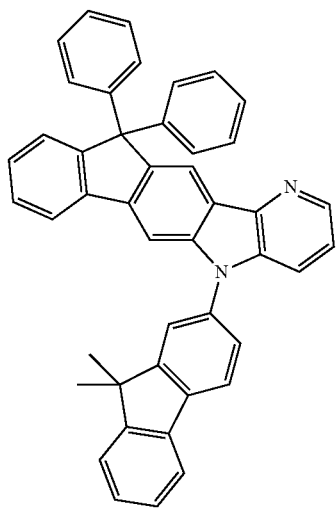
40
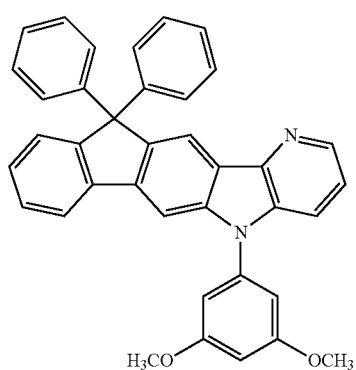
41
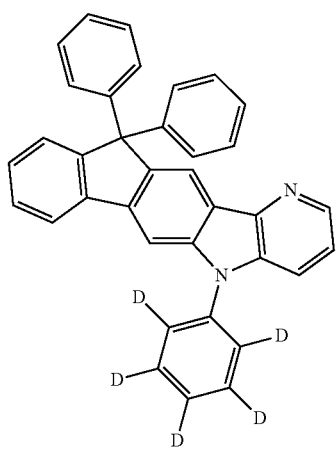
42
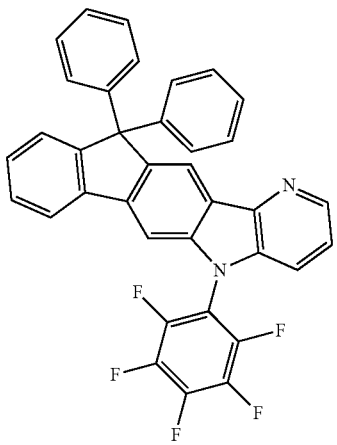
43
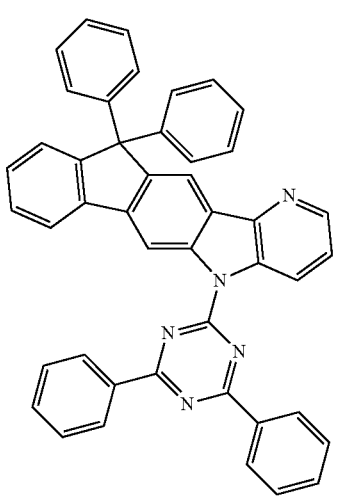
44
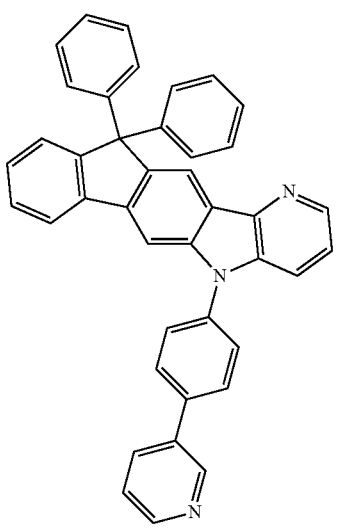

45
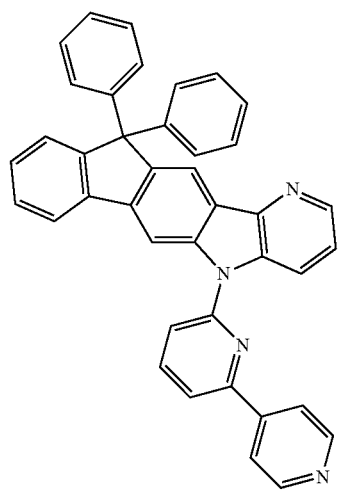
46
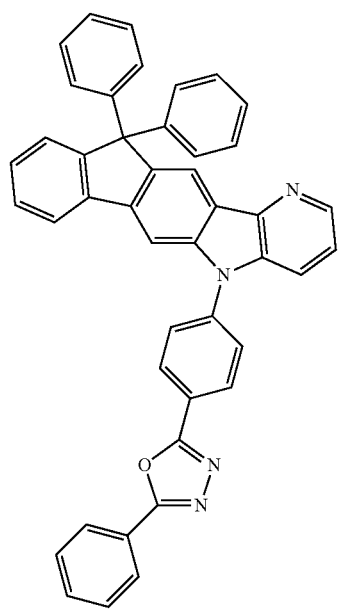
47
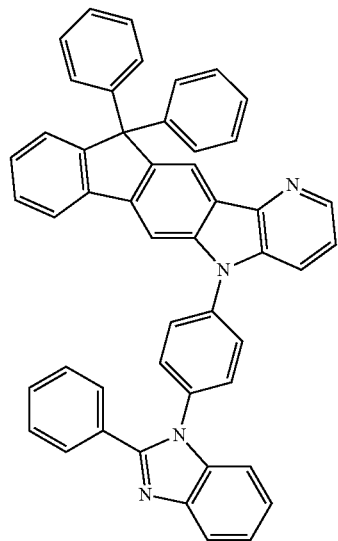
48
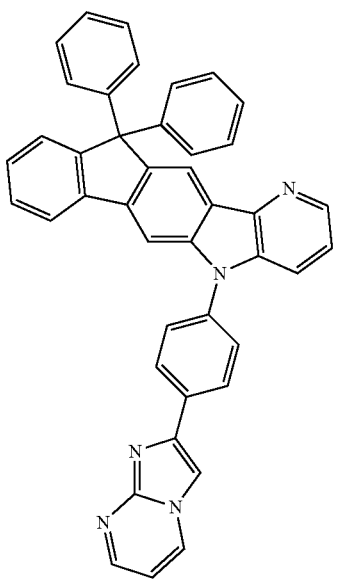
49
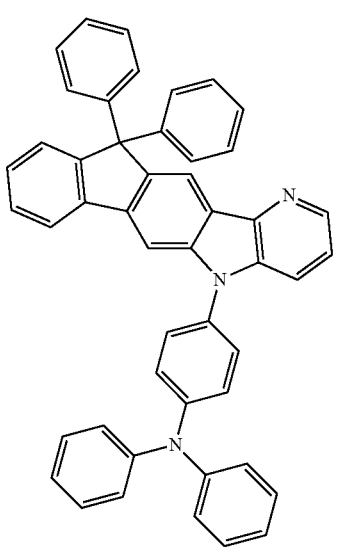
50
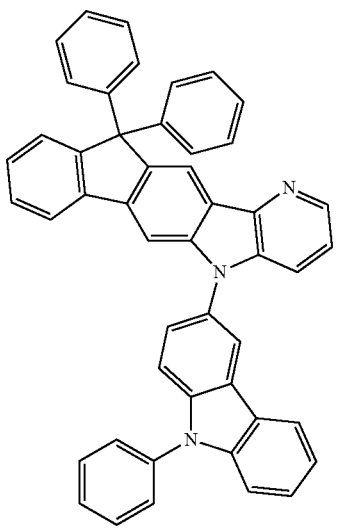

51
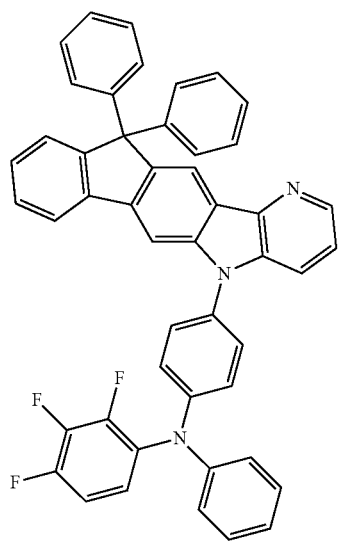
52
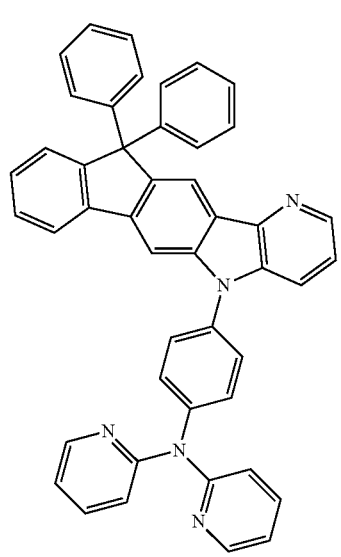
53
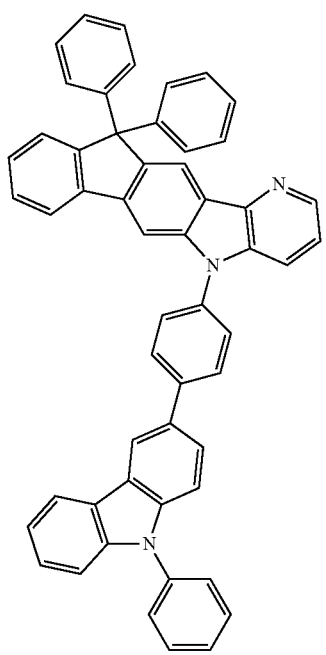
54
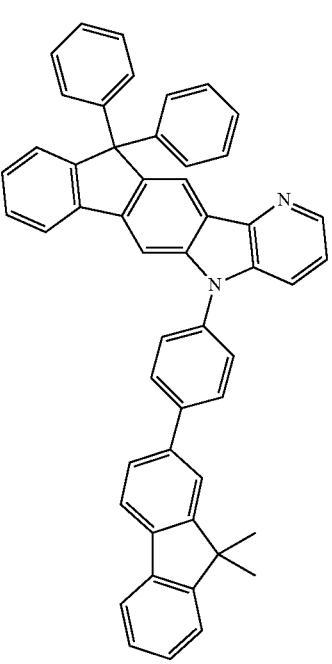

71
-continued
55
56
57
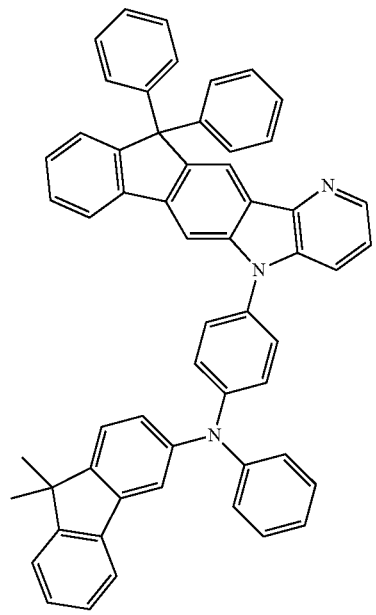
72
-continued
58
59
60
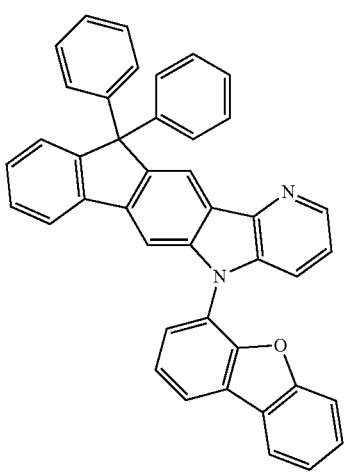
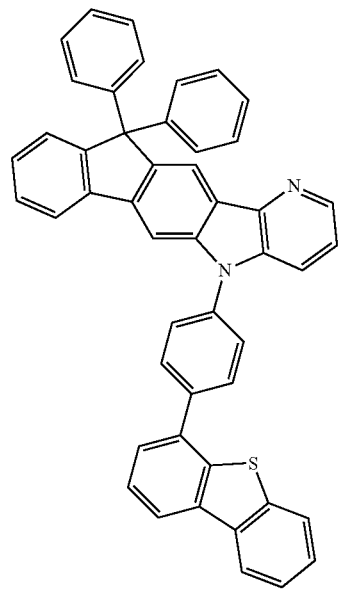
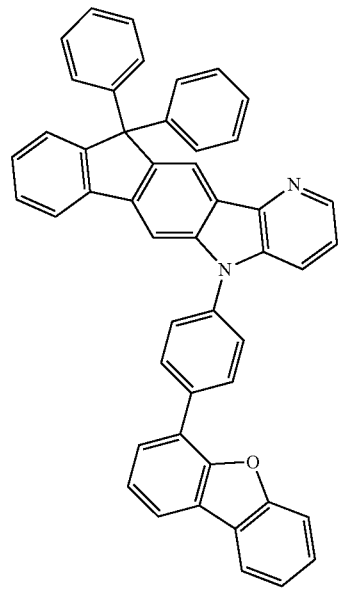

61
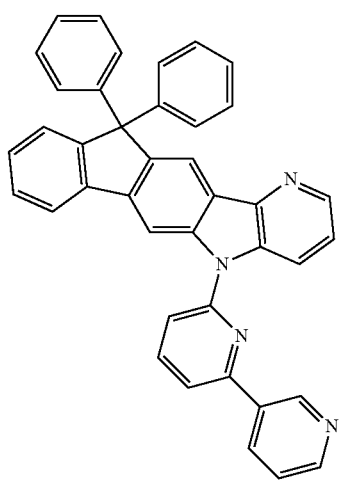
62
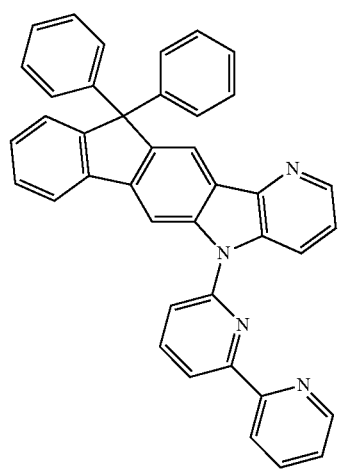
63
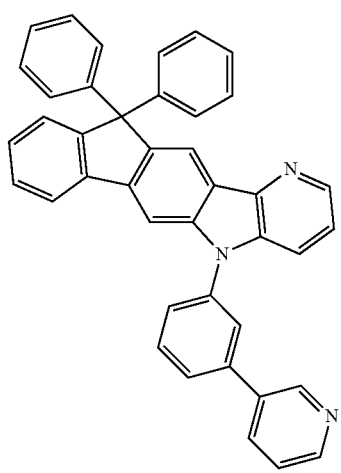
64
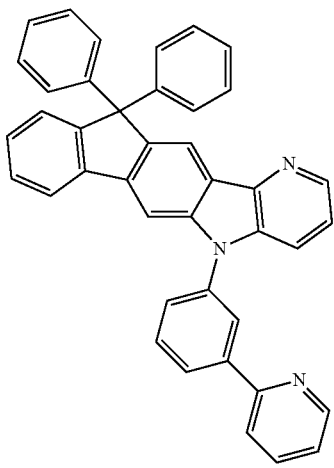
65
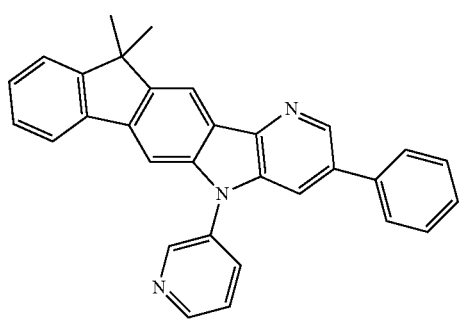
66
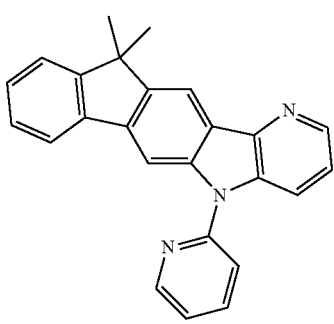
67
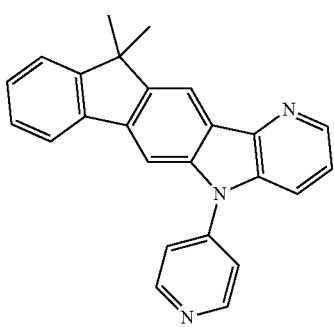

75
-continued
68
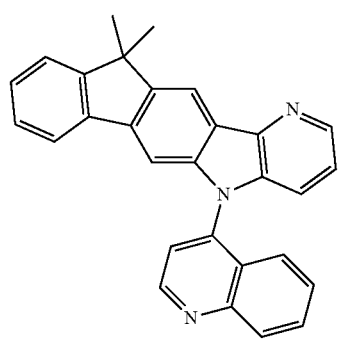
69
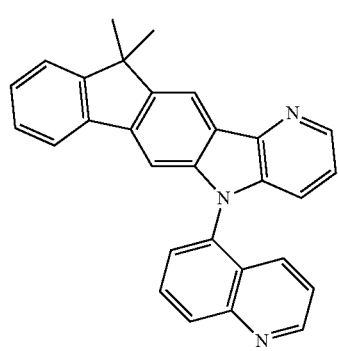
70
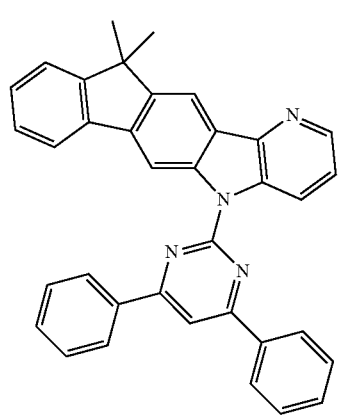
71
76
-continued
72
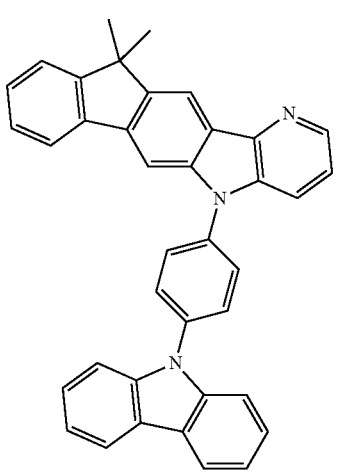
73
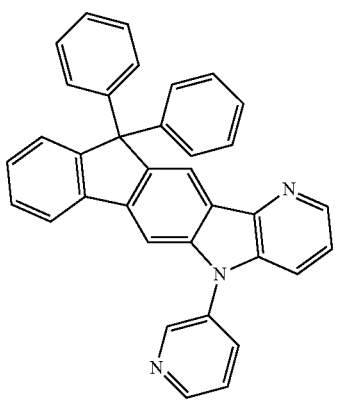
74
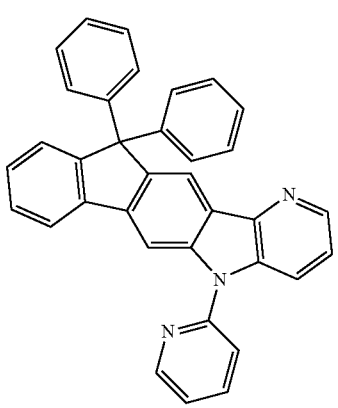

75
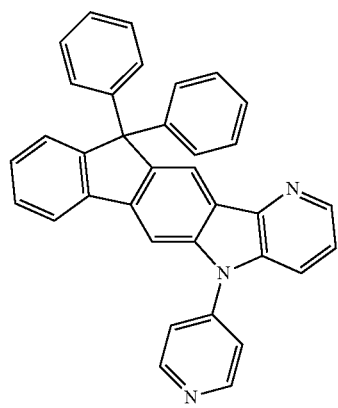
76
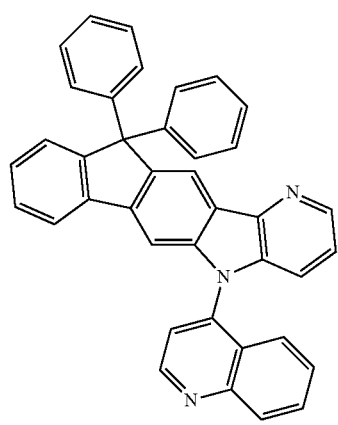
77
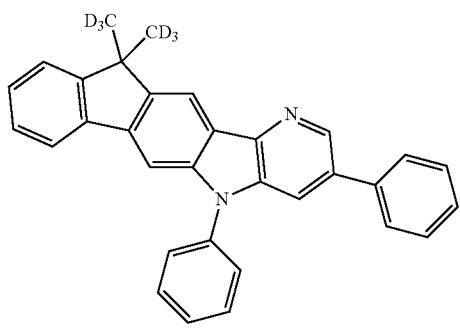
78
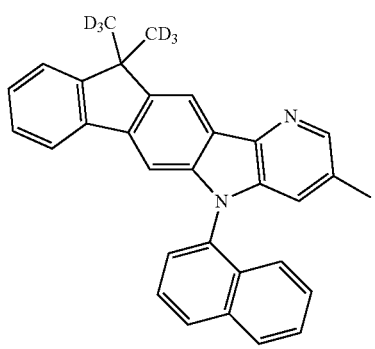
79
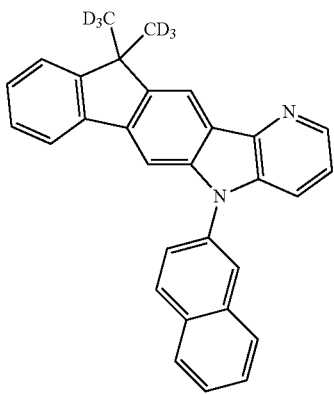
80
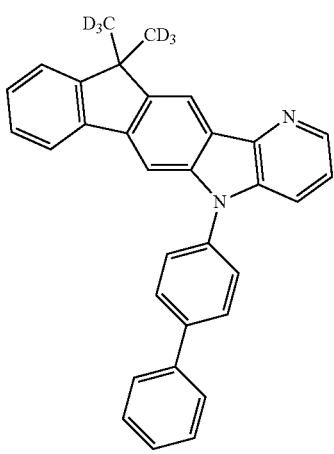
81
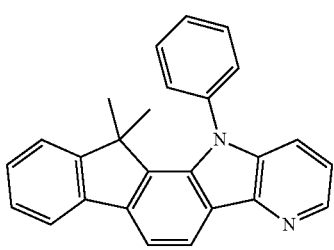
82
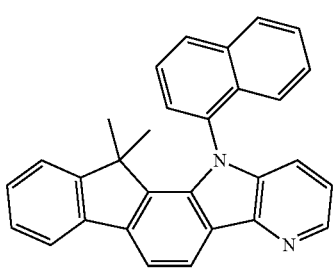

83
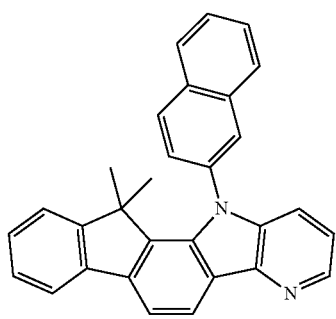
84
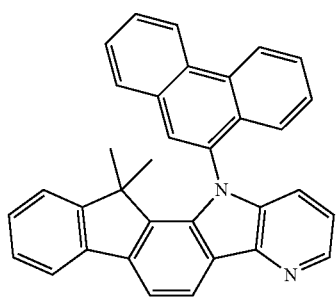
85
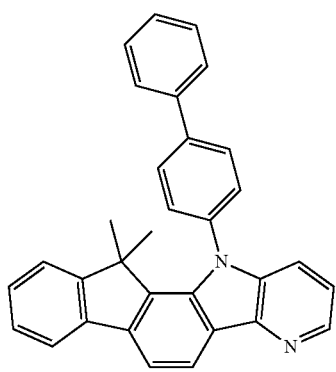
86
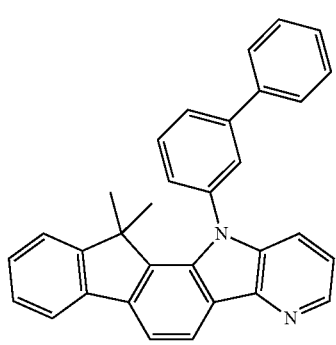
87
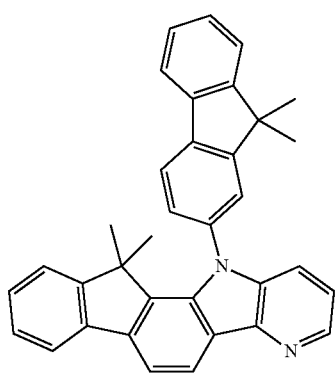
88
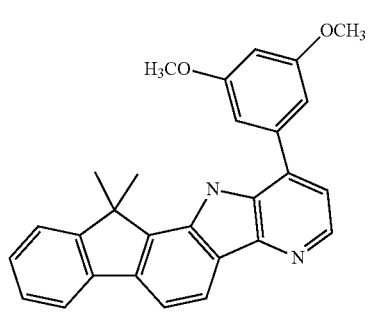
89
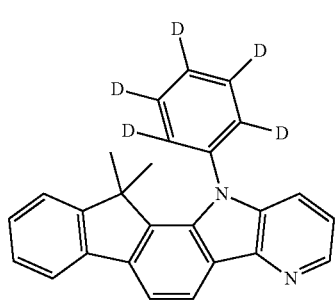
90
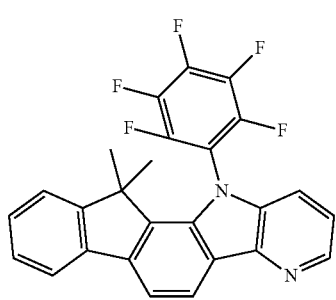
91
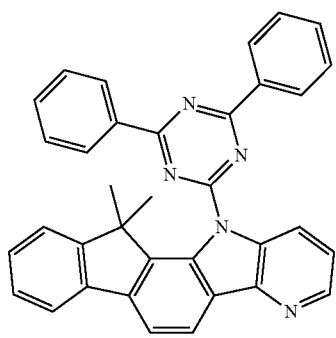

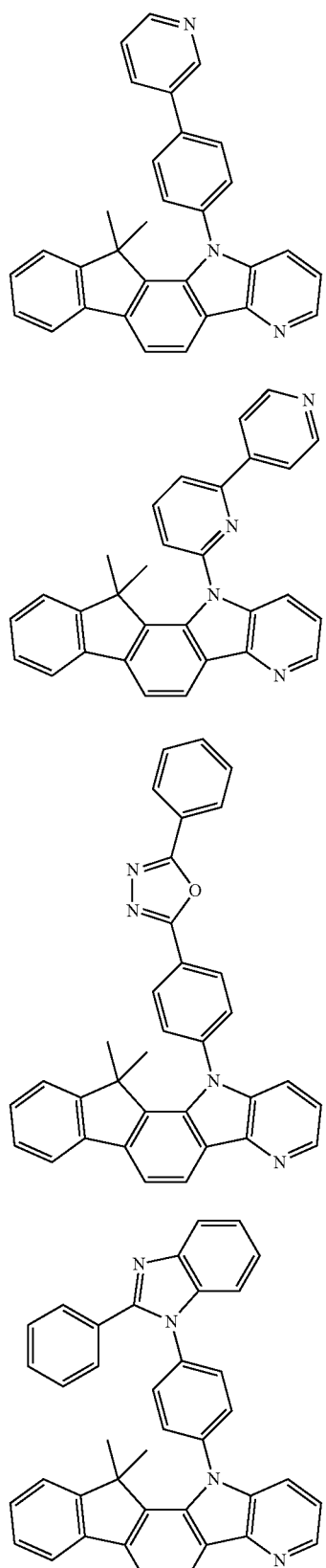
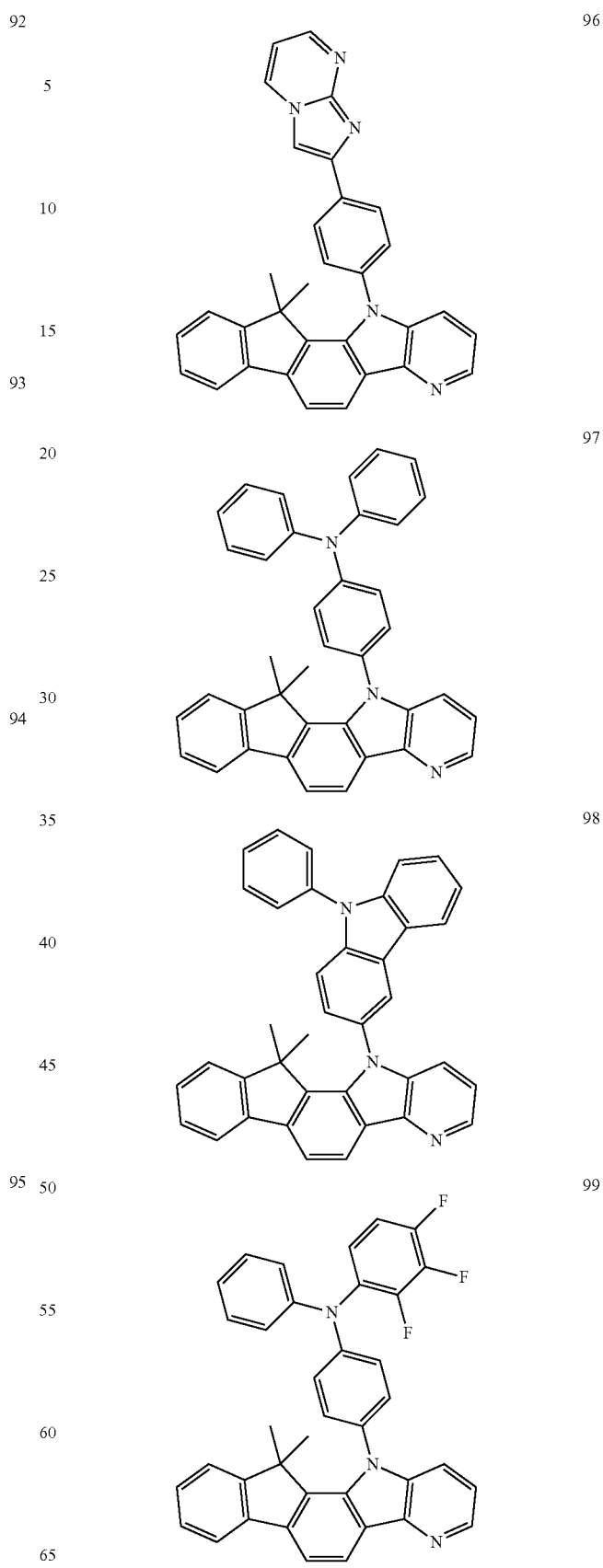

100
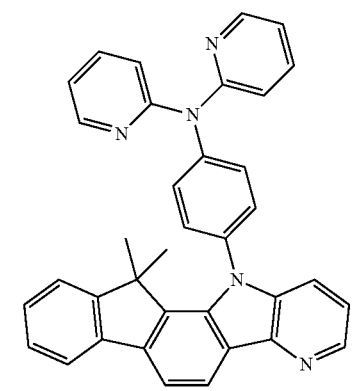
101
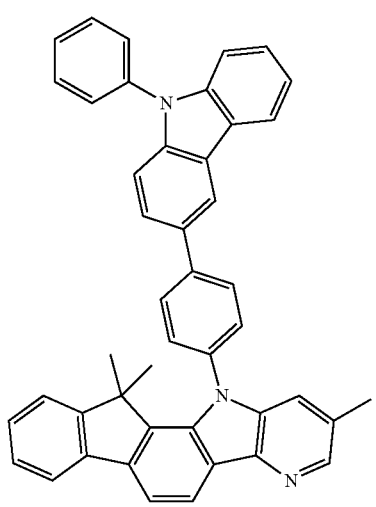
102
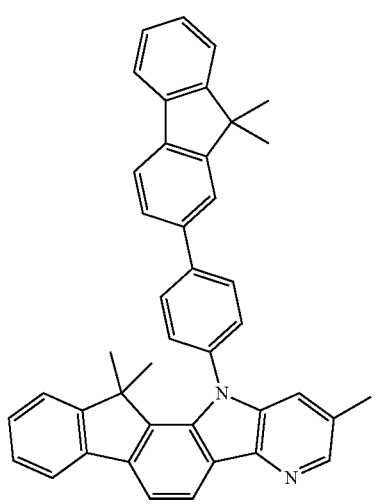
103
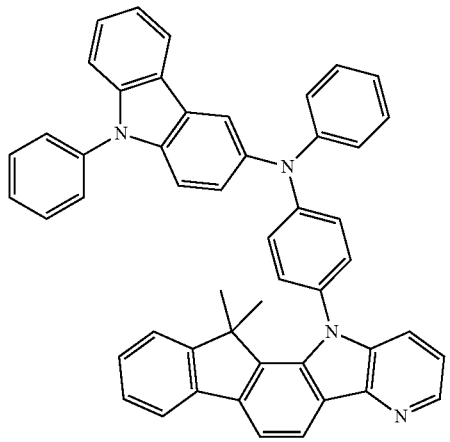
104
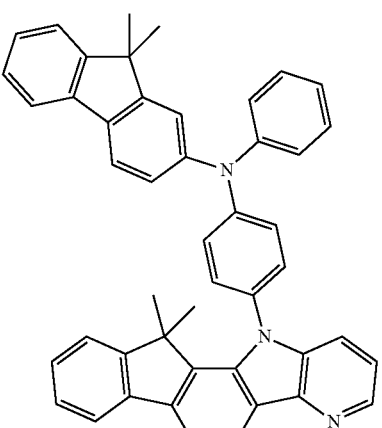
105
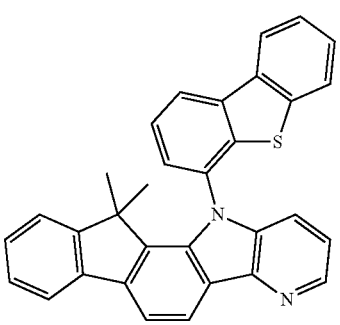
106
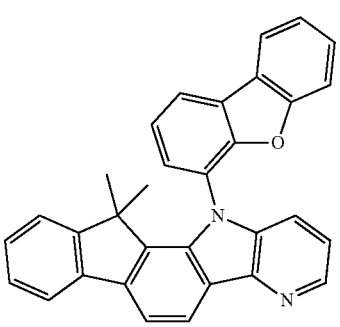

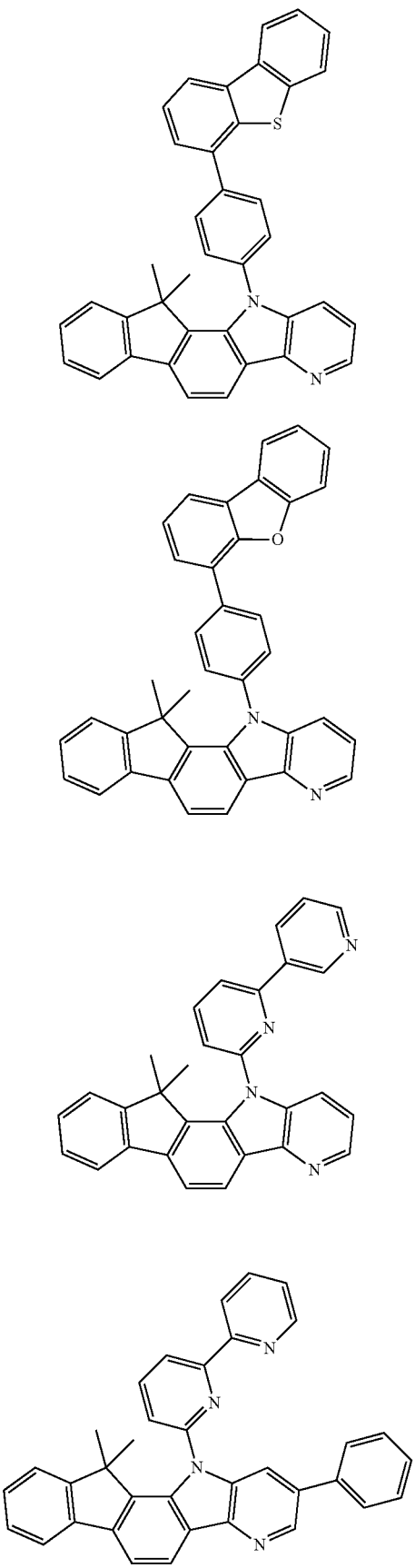

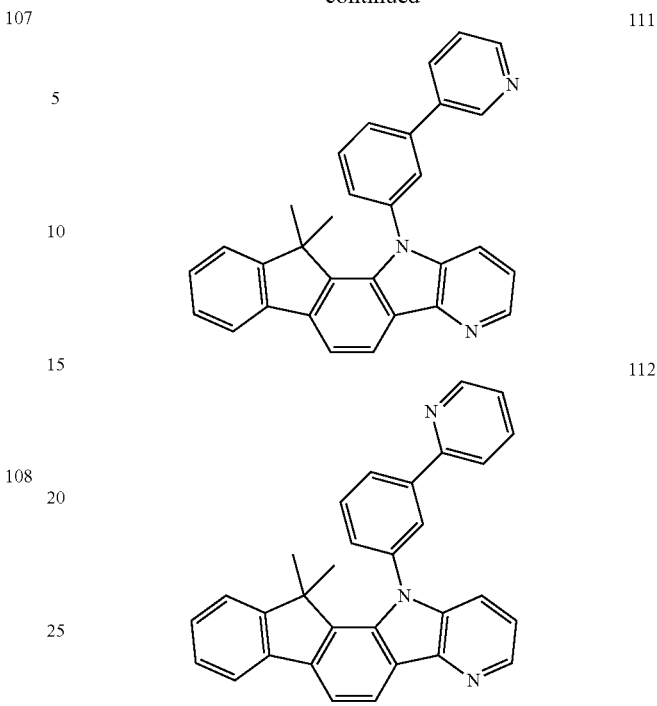

According to an embodiment, the heterocyclic compound may be compound 5, 7, 11, 17, or 30, but is not limited thereto.

The term "substituted A" in the term "substituted or unsubstituted A (where A is an arbitrary substituent)", used herein, refers to "A in which one or more hydrogen atoms of the A are substituted with a deuterium atom, a halogen atom, a hydroxyl group, a cyano group, a nitro group, a carboxylic group or salt derivative thereof, a sulfonic acid group or salt derivative thereof, a phosphoric acid group or salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_6$-$C_{30}$ aryl group, a $C_6$-$C_{30}$ aryloxy group, a $C_6$-$C_{30}$ arylthio group, a $C_3$-$C_{30}$ heteroaryl group, a group represented by N($Q_{101}$)($Q_{102}$), or a group represented by Si($Q_{103}$)($Q_{104}$)($Q_{105}$) where $Q_{101}$ to $Q_{105}$ are each independently a hydrogen atom, a deuterium atom, a halogen atom, a hydroxyl group, a cyano group, an amino group, a nitro group, a carboxylic group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_6$-$C_{30}$ aryl group, a $C_6$-$C_{30}$ aryloxy group, a $C_6$-$C_{30}$ arylthio group, or a $C_3$-$C_{30}$ heteroaryl group.

For example, the term "substituted A" refers to "A in which one or more hydrogen atoms of the A are substituted with a deuterium atom, a halogen atom, a hydroxyl group, a cyano group, a nitro group, a carboxylic group, a methyl group, ethyl group, a propyl group, a butyl group, a pentyl group, a methoxy group, an ethoxy group, a phenyl group, a biphenyl group, a pentalenyl group, a indenyl group, a naphthyl group, a azulenyl group, a heptalenyl group, a indacenyl group, a acenaphthyl group, a fluorenyl group, a spiro-fluorenyl group, a phenalenyl group, a phenanthrenyl group, a phenanthridinyl group, a phenanthrolinyl group, a anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, a imidazolyl group, a benzoimidazolyl group, a pyrazolyl group, a pyridinyl group, a pyrazinyl group, a pyrimidinyl group, a imidazopyrimidinyl group, a pyridazinyl group, a indolyl group, a isoindolyl group, a pyridoindolyl group, a indazolyl group, a purinyl group, a quinolinyl group, a benzoquinolinyl group, a phthalazinyl group, a naphthyridinyl group, a quinoxalinyl group, a quinazolinyl group, a carbazolyl group, a phenazinyl group, a furanyl group, a benzofuranyl group, a dibenzofuranyl group, a thiophenyl group, a benzothiophenyl group, a dibenzothiophenyl group, a thiazolyl group, a isothiazolyl group, a benzothiazolyl group, a oxazolyl group, a benzooxazolyl group, a isooxazolyl group, a oxadiazolyl group, a triazolyl group, a triazinyl group, a tetrazolyl group, a group represented by $N(Q_{101})(Q_{102})$, or a group represented by $Si(Q_{103})(Q_{104})(Q_{105})$.

The unsubstituted $C_1$-$C_{30}$ alkyl group used herein refers to a linear or branched saturated hydrocarbon group in which one hydrogen atom is deficient, and examples thereof include methyl, ethyl, propyl, isobutyl, sec-butyl, pentyl, iso-amyl, and hexyl. A substituent of the substituted $C_1$-$C_{30}$ alkyl group may be any one of the substituents presented above where the term "substituted A" is described in detail.

The unsubstituted $C_2$-$C_{30}$ alkenyl group used herein refers to a terminal group having at least one carbon-carbon double blond at the center or at a terminal end of the unsubstituted an unsubstituted $C_2$-$C_{30}$ alkyl group. Examples of the unsubstituted $C_2$-$C_{30}$ alkenyl group are ethenyl, propenyl, butenyl, pentenyl, hexenyl, heptenyl, octenyl, propadienyl, isoprenyl, and allyl. A substituent of the substituted $C_2$-$C_{30}$ alkenyl group may be any one of the substituents presented above where the term "substituted A" is described in detail.

The unsubstituted $C_2$-$C_{30}$ alkynyl group used herein refers to a terminal group having at least one carbon-carbon triple bond at the center or at a terminal end of the unsubstituted an unsubstituted $C_2$-$C_{60}$ alkyl group. Examples of the unsubstituted $C_2$-$C_{30}$ alkynyl group are acetylenyl, etc. A substituent of the substituted $C_2$-$C_{30}$ alkynyl group may be any one of the substituents presented above where the term "substituted A" is described in detail.

The unsubstituted $C_1$-$C_{30}$ alkoxy group used herein has a formula represented by —OY where Y is the unsubstituted $C_1$-$C_{60}$ alkyl group as defined above. Examples of the unsubstituted $C_1$-$C_{30}$ alkoxy group are methoxy, ethoxy, isopropyloxy, butoxy, pentoxy, etc. A substituent of the substituted $C_1$-$C_{30}$ alkoxy group may be any one of the substituents presented above where the term "substituted A" is described in detail.

The unsubstituted $C_3$-$C_{30}$ cycloalkyl group used herein refers to a cyclic saturated hydrocarbon group. Examples of the unsubstituted $C_3$-$C_{30}$ cycloalkyl group are cyclopropyl, cyclobutyl, cyclopentyl, cyclohexyl, cyclooctyl, etc. A substituent of the substituted $C_1$-$C_{30}$ cycloalkyl group may be any one of the substituents presented above where the term "substituted A" is described in detail.

The unsubstituted $C_3$-$C_{30}$ cycloalkenyl group used herein refers to a cyclic unsaturated hydrocarbon group having one or more carbon double bonds that is not an aromatic ring. Examples of the unsubstituted $C_3$-$C_{30}$ cycloalkenyl group are cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, 1,5-cyclooctadienyl, etc. A substituent of the substituted $C_3$-$C_{30}$ cycloalkenyl group may be any one of the substituents presented above where the term "substituted A" is described in detail.

The unsubstituted $C_6$-$C_{30}$ aryl group used herein refers to a monovalent group having a carbocyclic aromatic system in which the number of carbon atoms is 6 to 30, and may be a monocyclic group or a polycyclic group. If the unsubstituted $C_6$-$C_{30}$ aryl group is a polycyclic group, two or more rings contained in the unsubstituted $C_6$-$C_{30}$ aryl group may be fused. Examples of the unsubstituted $C_6$-$C_{30}$ aryl group are phenyl, pentalenyl, indenyl, naphtyl, azulenyl, heptalenyl, indacenyl, acenaphthyl, fluorenyl, spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, hexacenyl, etc. A substituent of the substituted $C_6$-$C_{30}$ aryl group may be any one of the substituents presented above where the term "substituted A" is described in detail.

The unsubstituted $C_6$-$C_{30}$ aryloxy group used herein refers to a monovalent group to which a carbon atom of the $C_6$-$C_{30}$ aryl group is attached to an oxygen linker (—O—). A substituent of the substituted $C_6$-$C_{30}$ aryloxy group may be any one of the substituents presented above where the term "substituted A" is described in detail.

The unsubstituted $C_6$-$C_{30}$ arylthio group used herein refers to a monovalent group to which a carbon atom of the $C_6$-$C_{30}$ aryl group is attached to a sulfur linker (—S—). Examples of the unsubstituted $C_6$-$C_{30}$ arylthio group are phenylthio, naphthylthio, indanylthio, and indenylthio. A substituent of the substituted $C_6$-$C_{30}$ arylthio group may be any one of the substituents presented above where the term "substituted A" is described in detail.

The unsubstituted $C_3$-$C_{30}$ heteroaryl group used herein refers to a monovalent aryl group including one or more cycles each including one or more hetero atoms selected from N, O, P, and S, and may be a monocyclic or polycyclic group. If the unsubstituted $C_3$-$C_{30}$ heteroaryl group is a polycyclic group, two or more cycles included therein may be fused with each other. Examples of the unsubstituted $C_3$-$C_{30}$ heteroaryl group are pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazol, oxadiazolyl, triazinyl, and benzooxazolyl. A substituent of the substituted $C_3$-$C_{30}$ heteroaryl group may be any one of the substituents presented above where the term "substituted A" is described in detail.

The unsubstituted $C_1$-$C_{30}$ alkylene group used herein refers to a linear or branched divalent group in which two hydrogen atoms are deficient in alkans. Examples of the unsubstituted $C_1$-$C_{30}$ alkylene group may be understood by referring to the examples of the unsubstituted $C_1$-$C_{30}$ alkyl group as described above. A substituent of the substituted $C_1$-$C_{30}$ alkylene group may be any one of the substituents presented above where the term "substituted A" is described in detail.

The unsubstituted $C_6$-$C_{30}$ arylene group used herein refers to a divalent group having a C6 to C30 carbocyclic aromatic system, and may be a monocyclic or polycyclic group. Examples of the unsubstituted $C_6$-$C_{30}$ arylene group may be understood by referring to the examples of the unsubstituted $C_6$-$C_{30}$ aryl group. A substituent of the substituted $C_6$-$C_{30}$ arylene group may be any one of the substituents presented above where the term "substituted A" is described in detail.

A heterocyclic compound represented by Formula 1 or Formula 2 above may be synthesized by using a known organic material synthesis method. A synthesis method for the heterocyclic compound may be easily understood by one of ordinary skill in the art in view of examples which will be described later.

The heterocyclic compound represented by Formula 1 or Formula 2 may be used in an organic light-emitting device.

An organic light-emitting device, according to an embodiment, may include a first electrode, a second electrode facing the first electrode, and a first layer interposed between the first electrode and the second electrode, wherein the first layer includes the heterocyclic compound represented by Formula 1 or Formula 2. In this regard, the first layer may include one or more layers.

The organic light-emitting device may further include, in addition to the first layer, at least one layer selected from the group consisting of a hole injection layer, a hole transport layer, a functional layer having a hole injection function and a hole transport function, an electron blocking layer, an emission layer, a hole blocking layer, an electron transport layer, an electron injection layer, and a functional layer having a hole injection function and a hole transport function, between the first electrode and the second electrode.

For example, the organic light-emitting device may have a structure of first electrode/hole injection layer/hole transport layer/first layer including the heterocyclic compound (that is, functioning as an emission layer)/electron transport layer/electron injection layer/second electrode, but the structure of the organic light-emitting device is not limited thereto.

For example, the organic light-emitting device may have a structure of first electrode/hole injection layer/hole transport layer/first layer including the heterocyclic compound (that is, functioning as an emission layer)/first layer including the heterocyclic compound (that is, functioning as an electron transport layer)/electron injection layer/second electrode, but the structure of the organic light-emitting device is not limited thereto. That is, the first layer refers to a layer including the heterocyclic compound and may be a plurality of layers which are separated from each other.

Between the first electrode and the second electrode may be, for example, the first layer and at least one additional layer. The at least one additional layer is not the first layer. The at least one additional layer may be selected from a hole injection layer, a hole transport layer, a functional layer having a hole injection function and a hole transport function, an electron blocking layer, an emission layer, a hole blocking layer, an electron transport layer, an electron injection layer, and a functional layer having a hole injection function and a hole transport function. In this regard, at least one of the layers may be formed by deposition or wet process.

The term "wet process" refers to a process in which a mixture including a material and a solvent is provided onto a substrate and then, dried and/or heat treated to remove at least a portion of the solvent, thereby forming a film including the material on the substrate.

For example, the first layer may be formed by using a conventional vacuum deposition method. Alternatively, a mixture including the heterocyclic compound and a solvent may be provided to a first layer forming region (for example, an upper portion of a hole transport layer) by spin coating, spraying, ink jet printing, dipping, casting, Gravure coating, bar coating, roll coating, wire bar coating, screen coating, flexo coating, offset coating, or laser transferring. The mixture on the first layer forming region may then be dried and/or heat treated to remove at least a portion of the solvent, thereby forming the first layer.

Alternatively, a first layer may be formed on a base film by the wet process as described above. The first layer may then be transferred to a first layer forming region (for example, an upper portion of a hole transport layer) by using a laser.

The first layer may be an electron injection layer, an electron transport layer, or a functional layer having an electron injection function and an electron injection function.

Meanwhile, the first layer may also be an emission layer. When the first layer is an emission layer, the first layer may include only the heterocyclic compound, or may further include, in addition to the heterocyclic compound, other compounds.

For example, the first layer may be an emission layer, and the heterocyclic compound included in the first layer may act as a fluorescent host or a phosphorescent host. Herein, the first layer may further include a fluorescent dopant or a phosphorescent dopant. For example, the first layer may be an emission layer that includes the heterocyclic compound acting as a fluorescent host and a fluorescent dopant, or an emission layer that includes the heterocyclic compound acting as a phosphorescent host and a phosphorescent dopant.

Alternatively, the first layer may be an emission layer and the heterocyclic compound included in the first layer may act as a fluorescent dopant. In this case, the first layer may further include a fluorescent host or a phosphorescent host. In detail, the first layer may be an emission layer that includes the heterocyclic compound acting as a fluorescent dopant and either a phosphorescent host or fluorescent host.

Alternatively, the first layer may be an emission layer and may include a fluorescent dopant formed of the heterocyclic compound and either a fluorescent host or a phosphorescent host which is formed of a heterocyclic compound that is different from that used as the fluorescent dopant. In this regard, the emission layer may further include a phosphorescent dopant.

Alternatively, the first layer in the organic light-emitting device may be an emission layer or an electron transport layer. The first layer may further include, in addition to the heterocyclic compound, one or more compounds selected from an anthracene-based compound, an arylamine-based compound, and a styryl-based compound.

Alternatively, the first layer in the organic light-emitting device may be an electron transport layer, and an emission layer may be additionally interposed between the first electrode and the second electrode. The emission layer may include at least one region selected from a red emission region, a green emission region, a blue emission region, and a white emission region. The at least one region selected from a red emission region, a green emission region, a blue emission region, and a white emission region may include a phosphorescent compound. The red emission region, the green emission region, the blue emission region, and the white emission region may be patterned by using a known method so as to produce a full-color image or embody a white emission. The phosphorescent compound may be selected from a known phosphorescent host and a known phosphorescent dopant.

FIG. 1 is a schematic view of an organic light-emitting device 10, according to an embodiment. Hereinafter, a structure of an organic light-emitting device and a method of manufacturing an organic light-emitting device will be described in detail using the heterocyclic compound 10 of FIG. 1, according to an embodiment.

The organic light-emitting device 10 may include a substrate 11, a first electrode 12, a hole injection layer 13, a hole transport layer 14, an emission layer 15, an electron transport layer 16, an electron injection layer 17, and a second electrode 18 which are sequentially disposed in the stated order.

The substrate 11 may be any one of various substrates that are used in a known organic light-emitting device, and may be a glass or transparent plastic substrate with excellent mechanical strength, thermal stability, transparency, surface smoothness, ease of handling, and water repellence.

The first electrode 12 may be formed by depositing or sputtering a first electrode material on the substrate 11. When the first electrode 12 is an anode, the first electrode material may be selected from high work-function materials so as to allow holes to be easily injected. The first electrode 12 may be a reflective electrode or a transmissible electrode. Examples of the first electrode 12 may include an indium tin oxide (ITO), an indium zinc oxide (IZO), a tin oxide ($SnO_2$), a zinc oxide (ZnO), etc. which are transparent and highly conductive. If magnesium (Mg), aluminum (Al), aluminum-lithium (Al—Li), calcium (Ca), magnesium-indium (Mg—In), or magnesium-silver (Mg—Ag) is used as the first electrode material, the first electrode 12 may be formed as a reflective electrode. The first electrode 12 may include two different materials. For example, the first electrode 12 may have a two-layer structure including two different materials.

The hole injection layer 13 may be disposed on the first electrode 12.

The hole injection layer 13 may be formed on the first electrode 12 by using various methods including vacuum deposition, wetting, or laser transferring as described above.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When a wet process, such as spin coating is performed to form a hole injection layer, coating conditions may vary according to the material used to form the hole injection layer, and the structure and thermal properties of the hole injection layer. For example, the coating conditions may include a coating speed of about 2000 rpm to about 5000 rpm, and a thermal treatment temperature of about 80° C. to about 200° C., wherein the thermal treatment serves to remove the solvent after coating. However, the coating conditions are not limited thereto.

A known hole injection material may be used as a hole injection layer material. Nonlimiting examples of a known hole injection material may be a phthalocyanine compound, such as copperphthalocyanine, 4,4',4"-tris(3-methylphenylphenylamino)triphenylamine (m-MTDATA) (formula presented below), 4,4'4'-Tris(N,N-diphenylamino)triphenylamine (TDATA) (formula presented below), 4,4',4"-tris{N,-(2-naphthyl)-N-phenylamino}-triphenylamine (2T-NATA) (formula presented below), polyaniline/dodecylbenzenesulfonic acid (PANI/DBSA) (formula presented below), poly (3,4-ethylenedioxythiophene)/poly(4-styrenesulfonate) (PEDOT/PSS) (formula presented below), polyaniline/camphor sulfonic acid (PANI/CSA), and polyaniline/poly(4-styrenesulfonate (PANI/PSS).

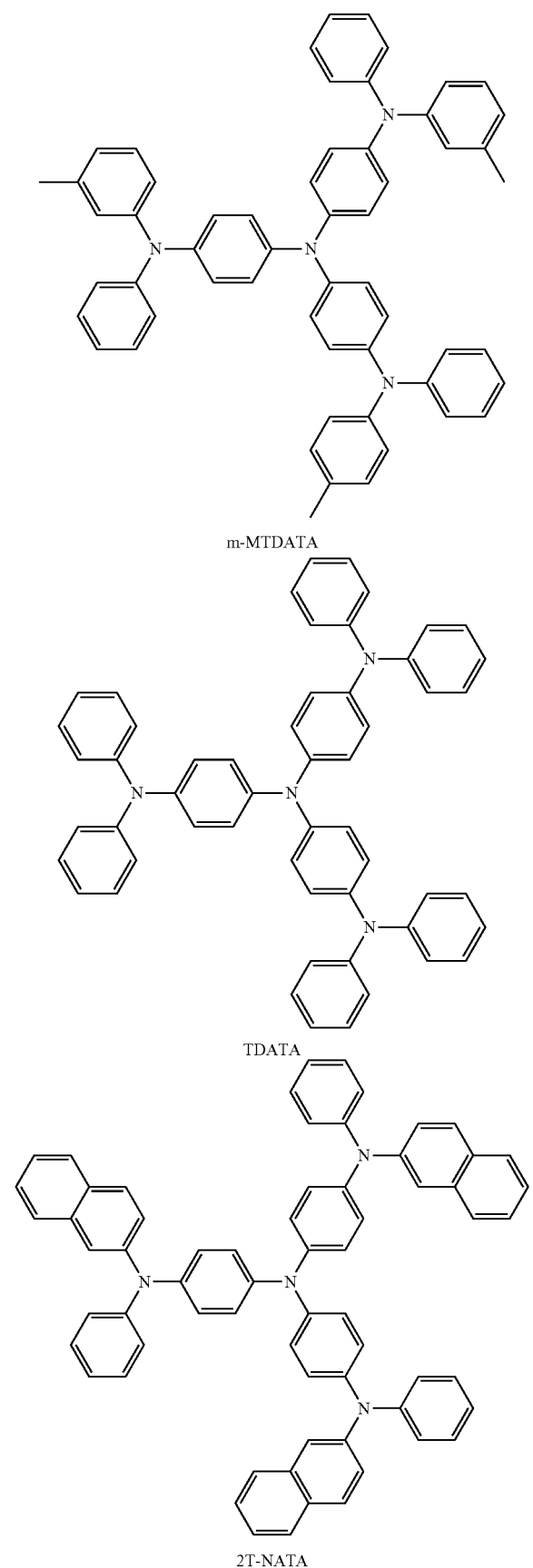

m-MTDATA

TDATA

2T-NATA

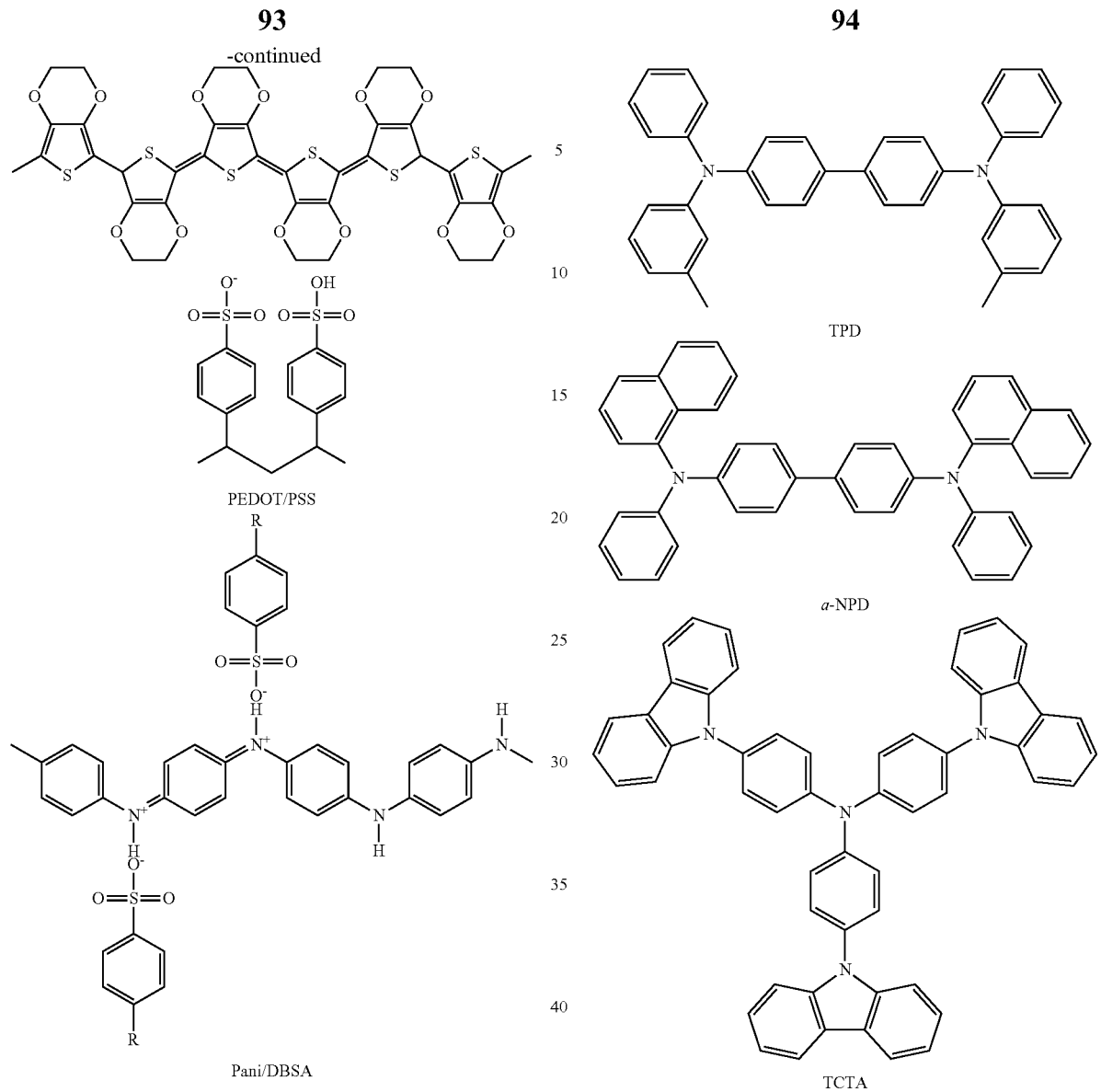

The hole injection layer may have a thickness of about 100 Å to about 10000 Å, for example, a thickness of about 100 Å to about 1000 Å. When the thickness of the hole injection layer is within these ranges, the hole injection layer may have good hole injection characteristics without an increase in driving voltage.

Then, the hole transport layer 14 may be formed on the hole injection layer 13 by vacuum deposition, wet process, or laser transferring. If the hole transport layer 14 is formed by vacuum deposition or spin coating, the deposition or coating conditions may be similar to those applied to form the hole injection layer 13. However, the deposition or coating conditions may vary according to the material that is used to form the hole transport layer 14.

As a hole transport layer material, a known hole transparent material may be used. Examples of a known hole transparent material may include a carbazole derivative, such as N-phenylcarbazole or polyvinylcarbazole; an amine derivative having an aromatic condensation ring, such as N,N'-bis(3-methylphenyl)-N,N'-diphenyl-[1,1-biphenyl]-4,4'-diamine (TPD), or 4,4'-bis[N-(1-naphthyl)-N-phenylamino]biphenyl (α-NPD); and a triphenylamine-based material, such as 4,4',4''-tris(N-carbazolyl)triphenylamine (TCTA).

The hole transport layer 14 may have a thickness of about 50 Å to about 1000 Å, for example, a thickness of about 100 Å to about 800 Å. When the thickness of the hole transport layer 14 is within the above range, the hole transport layer 14 may have excellent hole transport characteristics, without an increase in driving voltage.

An emission layer 15 may be formed on the hole transport layer 14 by vacuum deposition, wet process, or laser transferring. If the emission layer 15 is formed by vacuum deposition or spin coating, the deposition or coating conditions may be similar to those applied to form the hole injection layer 13. However, the deposition or coating conditions may vary according to the material that is used to form the emission layer 15.

The emission layer 15 may be a first layer including the heterocyclic compound represented by Formula 1 or Formula 2. The emission layer 15 may further include, in addition to the heterocyclic compound represented by Formula 1 or Formula 2, a known phosphorescent host, fluorescent host, phosphorescent dopant or fluorescent dopant. The heterocyclic compound may function as a phosphorescent host, a fluorescent host, a phosphorescent dopant, or a fluorescent dopant.

Nonlimiting examples of a known host are Alq₃, 4,4'-N,N'-dicabazole-biphenyl (CBP), poly(n-vinylcabazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), distyrylarylene (DSA), and E3.

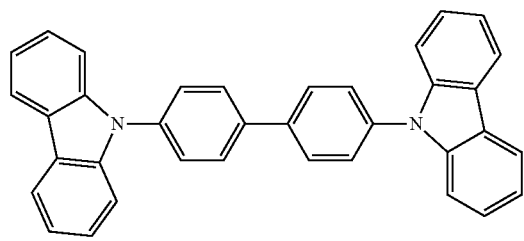

CBP

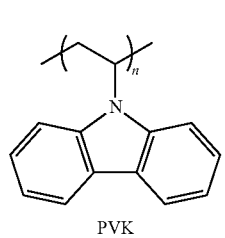

PVK

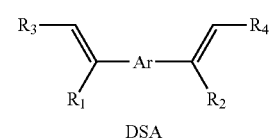

DSA

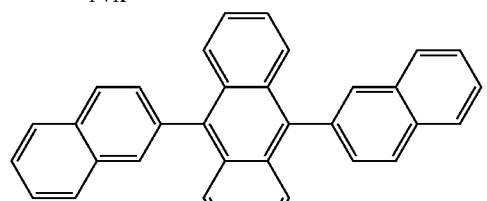

ADN

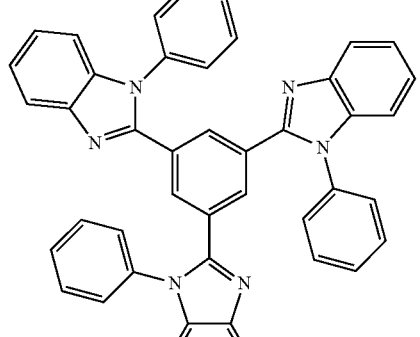

TPBI

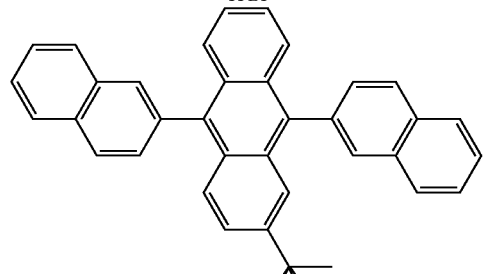

TBADN

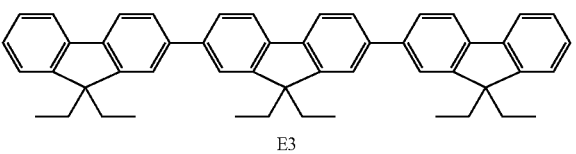

E3

Nonlimiting examples of a red dopant are PtOEP (formula presented below), Ir(piq)₃ (formula presented below), and Btp₂Ir (acac) (formula presented below).

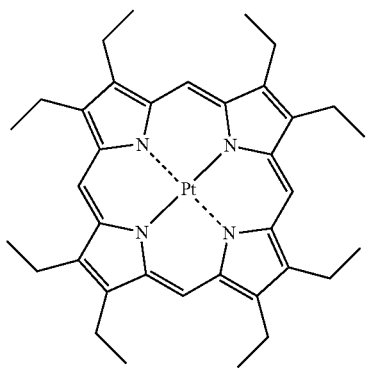

PtOEP

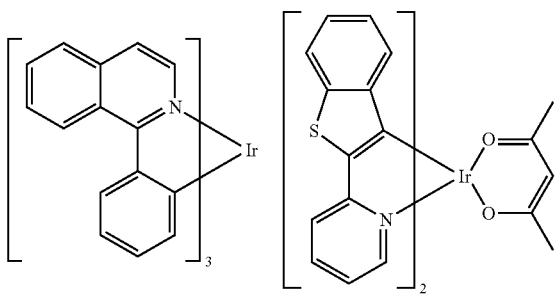

Ir(piq)₃          Btp₂Ir(acac)

Nonlimiting examples of a green dopant are, Ir(ppy)₃ (formula presented below) where ppy is an abbreviation of phenylpyridine, Ir(ppy)₂(acac) (formula presented below), and Ir(mpyp)₃ (formula presented below):

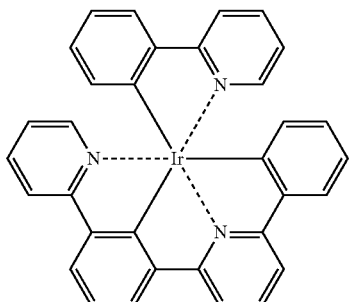

Ir(ppy)₃

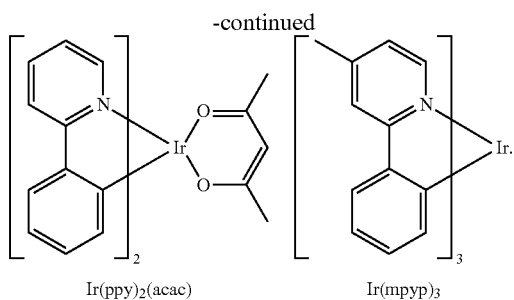

Ir(ppy)₂(acac)    Ir(mpyp)₃

Nonlimiting examples of a blue dopant are F₂Irpic (formula presented below), (F₂ppy)₂Ir(tmd) (formula is presented below), Ir(dfppz)₃ (formula presented below), DPVBi (formula presented below), 4,4'-bis(4-diphenylaminostaryl) biphenyl (DPAVBi), and 2,5,8,11-tetra-tert-butyl phenylene (TBPe).

A thickness of the emission layer 15 may be from about 100 Å to about 1000 Å, for example, about 200 Å to about 600 Å. If the thickness of the emission layer 15 is within the ranges described above, the emission layer 15 may have good light-emitting characteristics without an increase in driving voltage.

If the emission layer 15 includes a phosphorescent dopant, a hole blocking layer (HBL, not shown in FIG. 1) may be formed between the hole transport layer 16 and the emission layer 15 by vacuum deposition, a wet process, or laser transferring, so as to prevent diffusion of a triplet exciton or a hole to the hole transport layer 16. If a hole blocking layer is formed by vacuum deposition or spin coating, the deposition or coating conditions may be similar to those applied to form the hole injection layer 13. However, the deposition or coating conditions may vary according to the material that is used to form the hole blocking layer. As a hole blocking layer material, a known hole blocking material may be used.

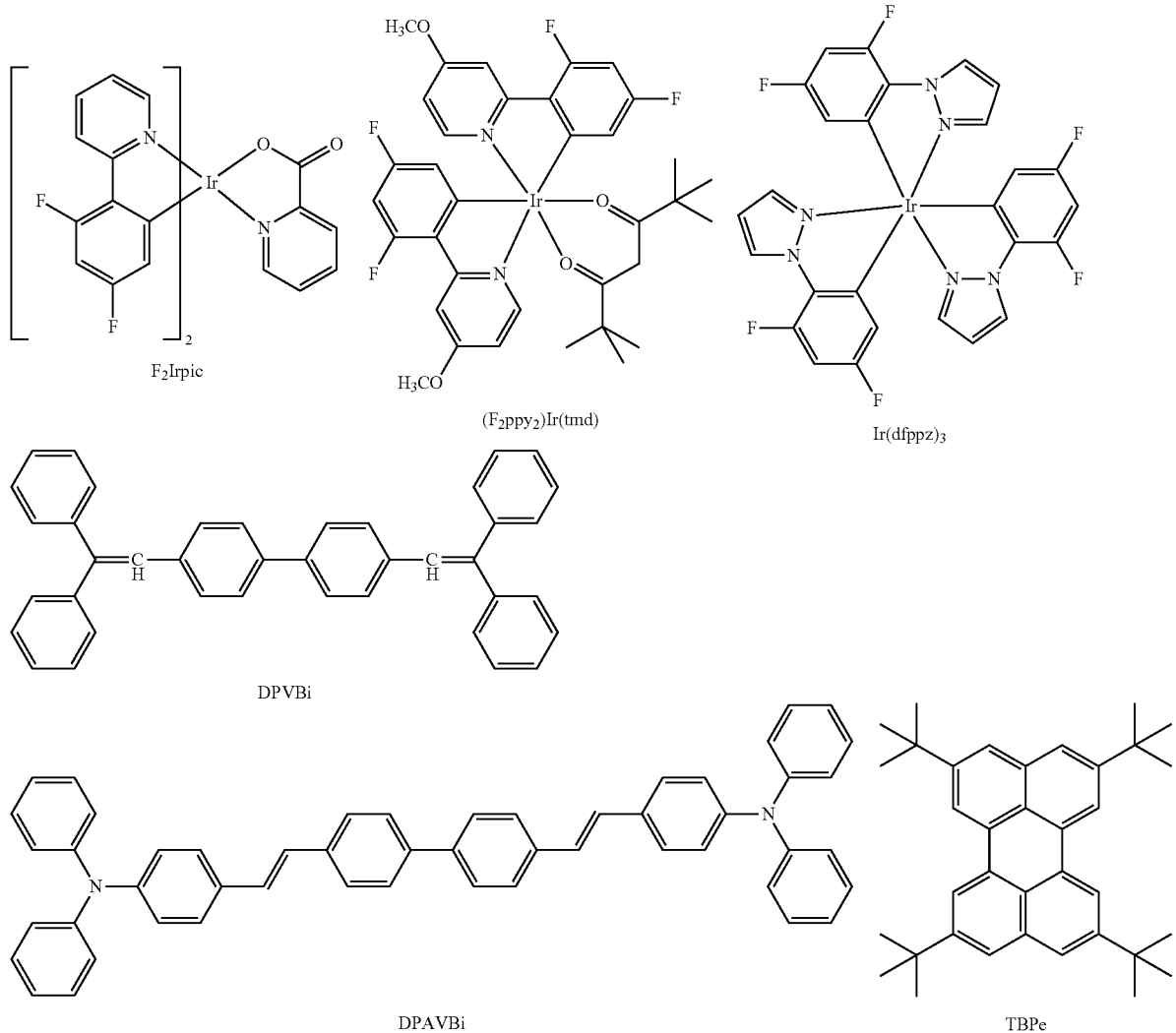

F₂Irpic    (F₂ppy₂)Ir(tmd)    Ir(dfppz)₃

DPVBi

DPAVBi    TBPe

If the emission layer 15 includes a host and a dopant, an amount of the dopant may be, in general, from about 0.01 to about 15 parts by weight, based on 100 parts by weight of the host, but is not limited thereto.

Examples of a known hole block material may include an oxydiazole derivative or phenanthroline derivative.

A thickness of the hole blocking layer may be about 50 Å to about 1000 Å, for example, about 100 Å to about 300 Å. If the thickness of the hole blocking layer is within these ranges, the hole blocking layer may have excellent hole blocking characteristics, without an increase in driving voltage.

Next, the electron transport layer 16 may be formed by using various methods, including vacuum deposition, a wet process, and laser transferring. If the electron transport layer 16 is formed by vacuum deposition or spin coating, the deposition or coating conditions may be similar to those applied to form the hole injection layer 13. However, the deposition or coating conditions may vary according to the material that is used to form the electron transport layer 16. As an electron transport material, the heterocyclic compound as described above, or any known electron transport material may be used. An example of the known electron transport material is a quinoline derivative. Nonlimiting examples of a quinoline derivative may include tris(8-quionlate)aluminum ($Alq_3$), TAZ (formula presented below), BAlq (formula presented below), and beryllium bis(benzoquinolin-10-olate) ($Bebq_2$).

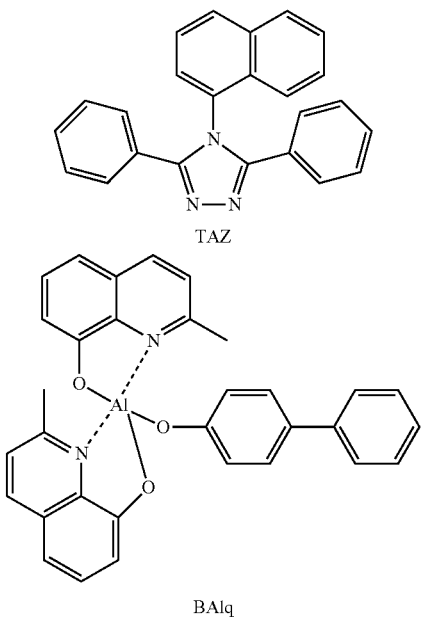

TAZ

BAlq

The electron transport layer 16 may have a thickness of about 100 Å to about 1,000 Å, for example, about 150 Å to about 500 Å. If the thickness of the electron transport layer 16 is within these ranges, the electron transport layer 16 may have satisfactory electron transport characteristics without an increase in driving voltage.

Also, a material that promotes each injection of electrons from an anode may be deposited on the electron transport layer 16 to form the electron injection layer 17. The material for forming the electron injection layer 17 may be any one of various electron injection layer forming materials, such as LiF, NaCl, CsF, $Li_2O$, or BaO. The deposition conditions may be similar to those applied to form the hole injection layer 13. However, the deposition conditions may vary according to the material that is used to form the electron injection layer 17.

The electron injection layer 17 may have a thickness of about 1 Å to 100 Å, for example, about 3 Å to about 90 Å. When the thickness of the electron injection layer 17 is within these ranges, the electron injection layer 17 may have satisfactory electron injection characteristics without an increase in driving voltage.

The second electrode 18, which may be a reflective electrode, may be disposed on the electron injection layer 17. The second electrode 18 may be a cathode, which is an electron injection electrode. In this case, as a second electrode forming metal, a low work-function metal, alloy, electrically conductive compound, or a mixture thereof may be used. For example, lithium (Li), magnesium(Mg), aluminum (Al), aluminum-lithium (Al—Li), calcium (Ca), magnesium-indium (Mg—In), or magnesium-silver (Mg—Ag) may be formed as a film to form a reflective electrode. Also, in order to manufacture a front emission-type device, a transmissible electrode formed of ITO or IZO may be used.

The organic light-emitting device may be included in a flat display device, including a transistor. Accordingly, the embodiments also provide a flat display device including a transistor having a source, a drain, a gate and an active layer and the organic light-emitting device as described above, wherein any one of the source and the drain is electrically connected to the first electrode of the organic light-emitting device. The active layer of the transistor may be an amorphous silicon layer, a crystalline silicon layer, an organic semiconductor layer, or an oxide semiconductor layer.

Hereinafter, examples of an organic light-emitting device according to an embodiment will be described in detail. However, the present invention is not limited to the examples.

EXAMPLE

Synthesis Example 1

Synthesis of Compound 5

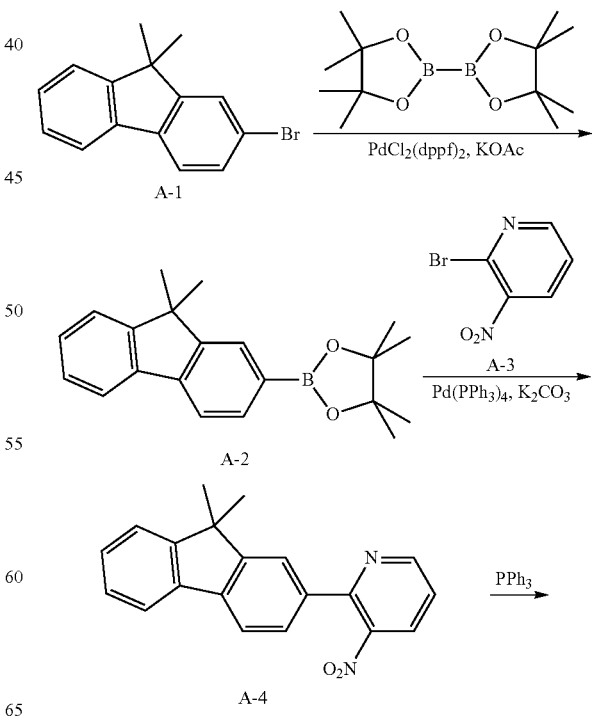

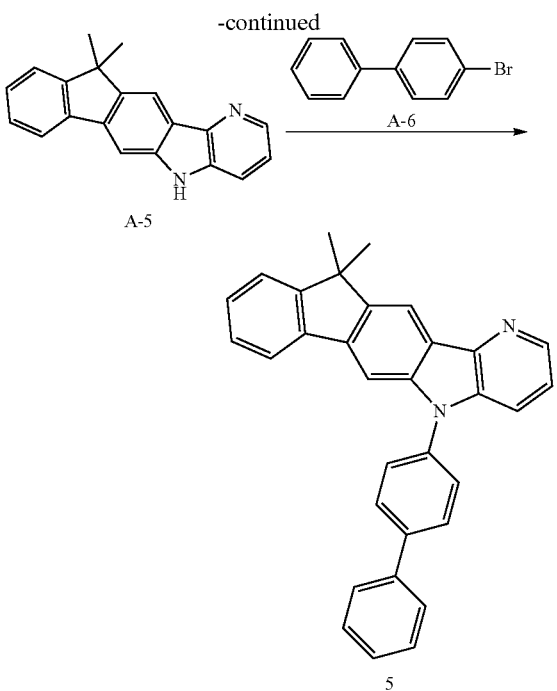

Synthesis of Intermediate A-2

2.73 g (10.0 mmol) of 2-bromo-9,9-dimethyl-9H-fluorene (A-1), 2.54 g (10.0 mmol) of bis(pinacholato)diborane, 0.36 g (0.5 mmol) of [1,1'-bis(diphenylphosphino)pherocene] dichloro palladium(II) (PdCl$_2$(dppf)$_2$), and 2.94 g (30.0 mmol) of KOAc were dissolved in 40 mL of DMSO and then, stirred at a temperature of 80° C. for 6 hours. The reaction solution was cooled to room temperature, followed by extraction with 50 mL of water and 50 mL of diethylether three times. An organic layer was collected and then dried using magnesium sulfate. The dried material was filtered to produce a filtered material. A solvent was removed from the filtered material by evaporation and a residue was obtained. The residue was separation-purified by silica gel column chromatography, thereby producing 1.95 g (Yield 82%) of Intermediate A-2(4,4,5,5-tetramethyl-2-(9,9-dimethyl-9H-fluorene-7-yl)-1,3,2-dioxabororane). The generated compound was confirmed by LC-MS and NMR.

$C_{21}H_{25}BO_2$: M+1 321.2

$^1$H NMR (CDCl$_3$, 400 MHz) δ (ppm) 7.83 (d, 1H), 7.37-7.67 (m, 6H), 1.75 (s, 6H), 1.32 (s, 12H)

Synthesis of Intermediate A-4

6.40 g (20.0 mmol) of Boron compound A-2, 4.06 g (20.0 mmol) of 2-bromo-3-nitropyridine (A-3), 1.15 g (1.0 mmol) of Pd(PPh$_3$)$_4$, and 8.29 g (60.0 mmol) of K$_2$CO$_3$ were dissolved in 60 ml of a mixed solution, including THF and H$_2$O, at a ratio of 2:1, and then stirred at a temperature of 70° C. for 5 hours. The reaction solution was cooled to room temperature, followed by extraction with 40 mL of water and 50 mL of ethylether three times. An organic layer was collected and dried using magnesium sulfate. The dried material was then filtered to produce a filtered material. A solvent was removed from the filtered material by evaporation and a residue was obtained. The residue was separation-purified by silica gel column chromatography, thereby producing Intermediate 2-(9,9-dimethyl-9H-fluorene-7-yl)-3-nitropyridine (A-4) 4.93 g (Yield 78%). The generated compound was confirmed by LC-MS and NMR.

$C_{20}H_{16}N_2O_2$: M+1 317.4

$^1$H NMR (CDCl$_3$, 400 MHz) δ (ppm) 8.64 (d, 1H), 8.12 (d, 1H), 7.25-8.05 (m, 8H), 1.67 (s, 6H)

Synthesis of Intermediate A-5

3.16 g (10.0 mmol) of Intermediate A-4 and 5.77 g (22 mmol) of triphenylphosphine (PPh$_3$) were dissolved in 30 mL of 1,2-dichlorobenzene and then, stirred at a temperature of 170° C. for 12 hours. The reaction solution was cooled to room temperature and a solvent was removed therefrom under vacuum conditions. Extraction with 50 mL of water and 50 mL of dichloromethane was then performed three times. An organic layer was collected and dried using magnesium sulfate. The dried material was filtered to produce a filtered material. A solvent was removed from the filtered material by evaporation and a residue was obtained. The residue was separation-purified by silica gel column chromatography, thereby producing 1.65 g (Yield 58%) of Intermediate A-5. The generated compound was confirmed by LC-MS and NMR. C20H16N2:M+ 284.4

$^1$H NMR (CDCl3, 400 MHz) δ (ppm) 10.5 (s, 1H), 8.25 (d, 1H), 7.32-8.10 (m, 8H), 1.61 (s, 6H)

Synthesis of Compound 5

2.84 g (10.0 mmol) of Intermediate A-5, 3.50 g (15.0 mmol) of 4-brome-4-biphenyl (A-6), 0.19 g (1.0 mmol) of CuI, 0.05 g (0.2 mmol) of 18-crown-6, and 4.15 g (30.0 mmol) of K$_2$CO$_3$ were dissolved in 30 mL of 1,3-dimethyl-3,4,5,6-tetrahydro-2(1H)-pyrimidinone (DMPU), and then stirred at a temperature of 170° C. for 12 hours. The reaction solution was cooled to room temperature, followed by extraction with 50 mL of water and 50 mL of dichloromethane three times. An organic layer was collected and then dried using magnesium sulfate. The dried material was filtered to produce a filtered material. A solvent was removed from the filtered material by evaporation and a residue was obtained. The residue was separation-purified by silica gel column chromatography, thereby producing Compound 5 (3.22 g, Yield 74%). The generated compound was confirmed by LC-MS and NMR.

$C_{32}H_{24}N_2$: M+ 436.5

$^1$H NMR (CDCl$_3$, 400 MHz) δ (ppm) 8.64 (d, 1H), 8.15 (d, 1H), 7.65-8.02 (m, 6H), 7.10-7.54 (m, 10H), 1.61 (s, 6H)

Synthesis Example 2

Synthesis of Compound 7

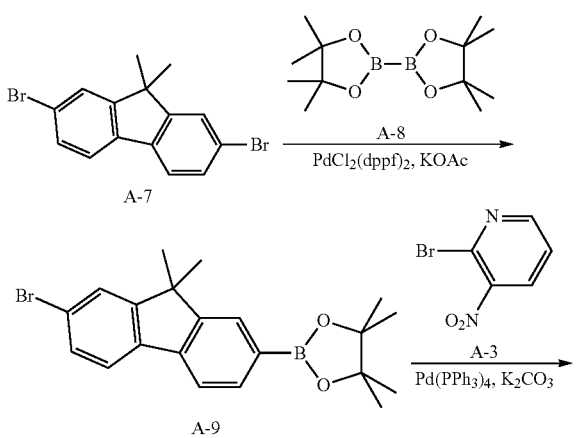

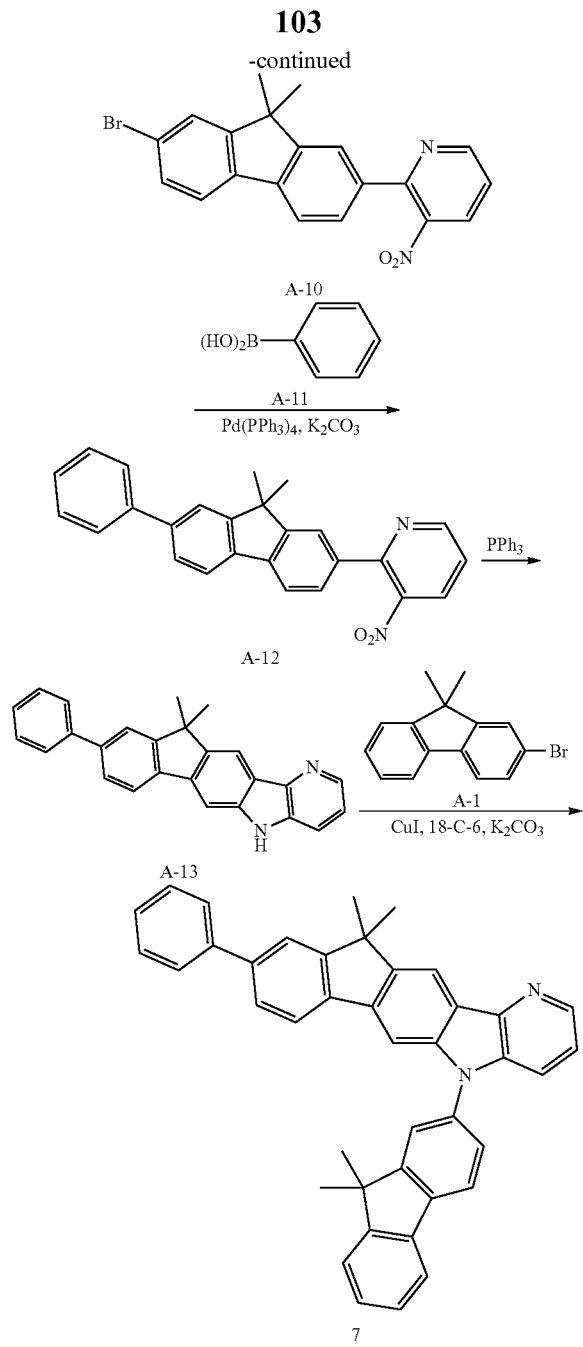

Synthesis of Intermediate A-9

7.04 g (20.0 mmol) of 2,7-dibromo-9,9-dimethyl-9H-fluorene (A-7), 2.54 g (10.0 mmol) of bis(pinacholato)diborane, 0.36 g (0.5 mmol) of PdCl$_2$(dppf)$_2$, and 2.94 g (30.0 mmol) of KOAc were dissolved in 60 mL of DMSO, and then stirred at a temperature of 80° C. for 6 hours. The reaction solution was cooled to room temperature, followed by extraction with 50 mL of water and 50 mL of diethylether three times. An organic layer was collected and dried using magnesium sulfate. The dried material was filtered to produce a filtered material. A solvent was removed from the filtered material by evaporation and a residue was obtained. The residue was separation-purified by silica gel column chromatography, thereby producing 2.69 g (Yield 85%) of Intermediate 2-(2-bromo-9,9-dimethyl-9H-fluorene-7-yl)-4,4,5,5-tetramethyl-1,3,2-dioxaborane (A-9). The generated compound was confirmed by LC-MS and NMR.

$C_{21}H_{24}BBrO_2$: M+1 400.1

$^1$H NMR (CDCl$_3$, 400 MHz) δ (ppm) 7.63 (d, 1H), 7.17-7.67 (m, 5H), 1.70 (s, 6H), 1.22 (s, 12H)

Synthesis of Intermediate A-10

8.00 g (20.0 mmol) of boron compound A-9, 4.06 g (20.0 mmol) of 2-bromo-3-nitropyridine (A-3), 1.15 g (1.0 mmol) of Pd(PPh$_3$)$_4$, and 8.29 g (60.0 mmol) of K$_2$CO$_3$ were dissolved in 60 ml of a mixed solution including THF and H$_2$O at a ratio of 2:1, and then, stirred at a temperature of 70° C. for 5 hours. The reaction solution was cooled to room temperature, followed by extraction with 40 mL of water and 50 mL of ethylether three times. An organic layer was collected and dried using magnesium sulfate. The dried material was filtered to produce a filtered material. A solvent was removed from the filtered material by evaporation and a residue was obtained. The residue was separation-purified by silica gel column chromatography, thereby producing 4.26 g (Yield 54%) of Intermediate 2-(2-bromo-9,9-dimethyl-9H-fluorene-7-yl)-3-nitropyridine (A-10). The generated compound was confirmed by LC-MS and NMR.

$C_{20}H_{15}BrN_2O_2$: M+1 396.2

$^1$H NMR (CDCl$_3$, 400 MHz) δ (ppm) 8.94 (d, 1H), 8.42 (d, 1H), 7.95-8.23 (m, 3H), 7.25-7.65 (m, 4H), 1.67 (s, 6H)

Synthesis of Intermediate A-12

7.95 g (20.0 mmol) of boron compound A-10, 2.44 g (20.0 mmol) of phenylboronic acid (A-11), 1.15 g (1.0 mmol) of Pd(PPh$_3$)$_4$, and 8.29 g (60.0 mmol) of K$_2$CO$_3$ was dissolved in 60 ml of a mixed solution including THF and H$_2$O at a ratio of 2:1, and then stirred at a temperature of 70° C. for 5 hours. The reaction solution was cooled to room temperature, followed by extraction with 40 mL of water and 50 mL of ethylether three times. An organic layer was collected and dried using magnesium sulfate. The dried material was filtered to produce a filtered material. A solvent was removed from the filtered material by evaporation and a residue was obtained. The residue was separation-purified by silica gel column chromatography, thereby producing 5.80 g (Yield 74%) of Intermediate 2-(9,9-dimethyl-2-phenyl-9H-fluorene-7-yl)-3-nitropyridine (A-12). The generated compound was confirmed by LC-MS and NMR.

$C_{26}H_{20}N_2O_2$: M+1 393.4

$^1$H NMR (CDCl$_3$, 400 MHz) δ (ppm) 8.90 (d, 1H), 8.48 (d, 1H), 7.91-8.23 (m, 3H), 7.25-7.75 (m, 9H), 1.66 (s, 6H)

Synthesis of Intermediate A-13

3.92 g (10.0 mmol) of Intermediate A-12 and 5.77 g (22 mmol) of triphenylphosphine (PPh$_3$) were dissolved in 30 mL of 1,2-dichlorobenzene, and then, stirred at a temperature of 170° C. for 12 hours. The reaction solution was cooled to room temperature, and a solvent was removed therefrom under vacuum conditions, followed by extraction with 50 mL of water and 50 mL of dichloromethane three times. An organic layer was collected and dried using magnesium sulfate. The dried material was filtered to produce a filtered material. A solvent was removed from the filtered material by evaporation and a residue was obtained. The residue was separation-purified by silica gel column chromatography, thereby producing 2.23 g (Yield 62%) of Intermediate A-13. The generated compound was confirmed by LC-MS and NMR.

$C_{26}H_{20}N_2$: M+ 360.5

$^1$H NMR (CDCl$_3$, 400 MHz) δ (ppm) 10.1 (s, 1H), 8.55 (d, 1H), 7.81-8.12 (m, 3H), 7.32-7.67 (m, 8H), 1.61 (s, 6H)

Synthesis of Compound 7

3.60 g (10.0 mmol) of Intermediate A-12 , 4.09 g (15.0 mmol) of 2-bromo-9,9-dimethyl-9H-fluorene (A-1), 0.19 g (1.0 mmol) of CuI, 0.05 g (0.2 mmol) of 18-crown-6, and 4.15 g (30.0 mmol) of K$_2$CO$_3$ were dissolved in 30 mL of DMPU, and then, stirred at a temperature of 170° C. for 12 hours. The reaction solution was cooled to room temperature, followed by extraction with 50 mL of water and 50 mL of dichloromethane three times. An organic layer was collected and dried using magnesium sulfate. The dried material was filtered to produce a filtered material. A solvent was removed from the filtered material by evaporation and a residue was obtained. The residue was separation-purified by silica gel column chromatography, thereby producing Compound 7 (3.75 g, Yield 68%). The generated compound was confirmed by LC-MS and NMR.

$C_{41}H_{32}N_2$: M+ 552.7

$^1$H NMR (CDCl$_3$, 400 MHz) δ (ppm) 8.64 (d, 1H), 8.15 (d, 1H), 7.78-8.02 (m, 2H), 7.04-7.64 (m, 16H), 1.69 (s, 6H), 1.54 (s, 6H)

Synthesis Example 3

Synthesis of Compound 11

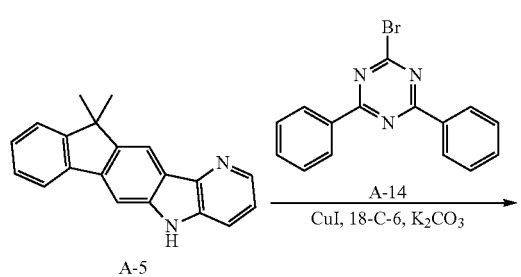

Synthesis of Compound 11

Intermediate A-5 was synthesized in the same manner as Compound 5. Compound 11 (3.65 g, 71%) was synthesized in the same manner as Compound 5, except that 3.50 g (15.0 mmol) of Intermediate 2-bromo-4,6-diphenyl-1,3,5-triazine (A-14) was used instead of 3.50 g (15.0 mmol) of Intermediate 4-brome-4-biphenyl (A-6). The generated compound was confirmed by LC-MS and NMR.

$C_{35}H_{25}N_5$: M+ 515.6

$^1$H NMR (CDCl$_3$, 400 MHz) δ (ppm) 8.54 (d, 1H), 8.05 (d, 1H), 7.55-7.72 (m, 2H), 7.10-7.44 (m, 15H), 1.64 (s, 6H)

Synthesis Example 4

Synthesis of Compound 17

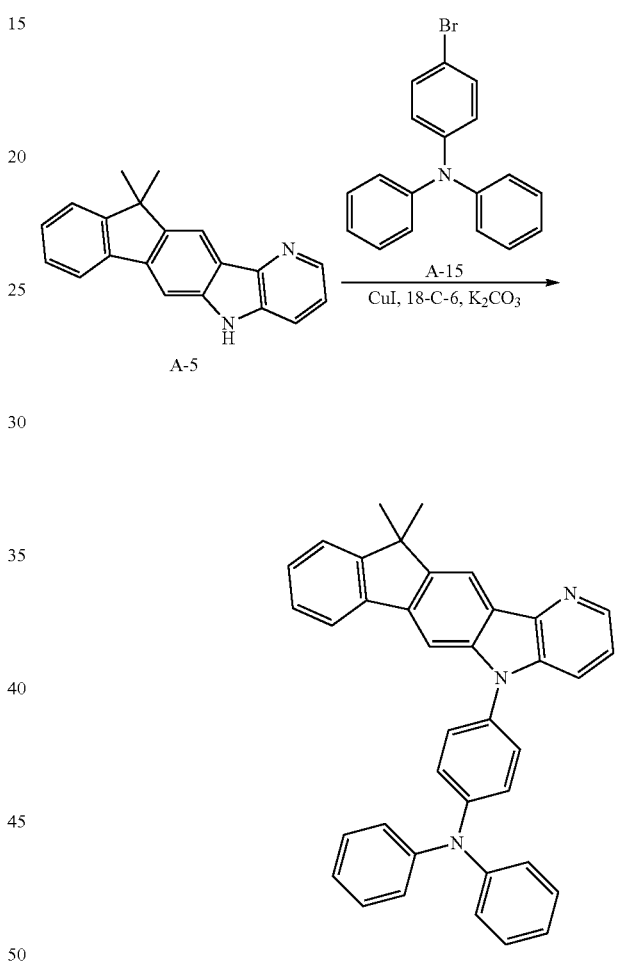

Synthesis of Compound 17

Intermediate A-5 was synthesized in the same manner as Compound 5. Compound 17 (3.68 g, 68%) was synthesized in the same manner as Compound 5, except that 4.86 g (15.0 mmole) of Intermediate tris(4-bromophenyl)amine (A-15) was used instead of 3.50 g (15.0 mmol) of Intermediate 4-brome-4-biphenyl (A-6). The generated compound was confirmed by LC-MS and NMR.

$C_{38}H_{29}N_3$: M+ 527.7

$^1$H NMR (CDCl3, 400 MHz) δ (ppm) 8.64 (d, 1H), 8.11 (d, 1H), 7.51-7.77 (m, 2H), 7.10-7.34 (m, 5H), 6.70-7.00 (m, 14H), 1.69 (s, 6H)

Synthesis Example 5

Synthesis of Compound 30

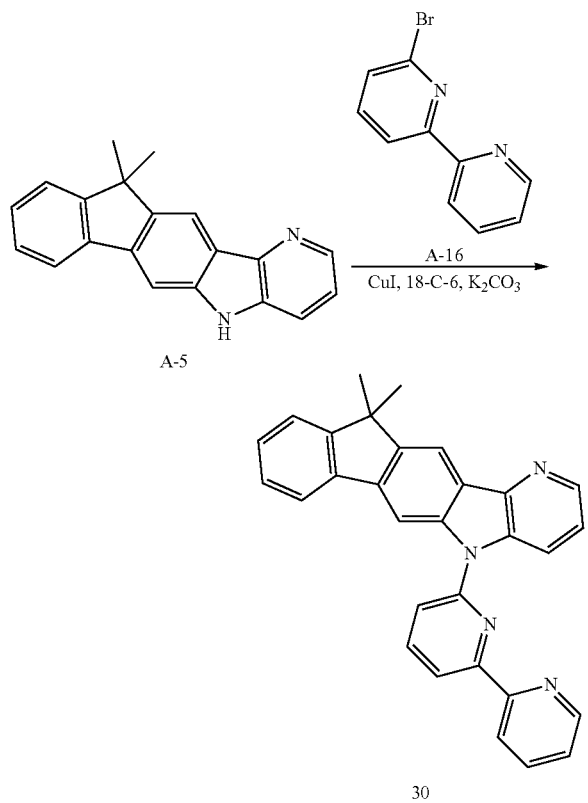

Synthesis of Compound 30

Intermediate A-5 was synthesized in the same manner as Compound 5. Compound 30 (3.37 g, 77%) was synthesized in the same manner as Compound 5, except that 3.52 g (15.0 mmol) of Intermediate 2-(6-bromopyridine-2-yl)pyridine (A-16) was used instead of 3.50 g (15.0 mmol) of Intermediate 4-brome-4-biphenyl (A-6). The generated compound was confirmed by LC-MS and NMR.

$C_{30}H_{22}N_4$: M+ 438.5

$^1$H NMR (CDCl$_3$, 400 MHz) δ (ppm) 8.54-8.65 (m, 4H), 7.98-8.11 (d, 1H), 7.51-7.78 (m, 7H), 7.10-7.34 (m, 4H), 1.59 (s, 6H)

Example 1

As an anode, 15 Ω/cm² (1200 Å) ITO glass substrate, which was manufactured by Corning Company, was cut to a size of 50 mm×50 mm×0.7 mm and sonicated with isopropyl alcohol and pure water each for 5 minutes, and an ultraviolet (UV) ray was irradiated thereto for 30 minutes, followed by exposure to ozone. The resultant ITO glass substrate was placed in a vacuum deposition device. 2-TNATA was vacuum deposited on the ITO to form a hole injection layer having a thickness of 600 Å. NPB was vacuum deposited on the hole injection layer to form a hole transport layer having a thickness of 300 Å. Compound 5 as a host and DPVBi as a dopant were co-deposited at a weight ratio of 98:2 on the hole transport layer to form an emission layer having a thickness of 300 Å. Alq$_3$ was vacuum deposited on the emission layer to form an electron transport layer having a thickness of 300 Å. LiF was vacuum deposited on the electron transport layer to form an electron injection layer having a thickness of 10 Å. Then, Al was vacuum deposited on the electron injection layer to form a cathode having a thickness of 3000 Å, thereby completing manufacture of an organic light-emitting device.

Example 2

An organic light-emitting device was manufactured in the same manner as described in Example 1, except that Compound 7 was used as a host instead of Compound 5 when an emission layer was formed.

Example 3

An organic light-emitting device was manufactured in the same manner as in Example 1, except that Compound 11 was used as a host instead of Compound 5 when an emission layer was formed.

Example 4

An organic light-emitting device was manufactured in the same manner as described in Example 1, except that Compound 17 was used as a host instead of Compound 5 when an emission layer was formed.

Example 5

An organic light-emitting device was manufactured in the same manner as described in Example 1, except that ADN was used as a host for forming an emission layer, instead of Compound 5, and Compound 11 was used as a material for forming an electron transport layer instead of Alq$_3$.

Example 6

An organic light-emitting device was manufactured in the same manner as described in Example 5, except that Compound 30 was used instead of Compound 11 when an electron transport layer was formed.

Example 7

An organic light-emitting device was manufactured in the same manner as described in Example 1, except that Compound 11 was used as a material for forming an electron transport layer instead of Alq$_3$.

Example 8

An organic light-emitting device was manufactured in the same manner as described in Example 1, except that, Compound 30 was used as a material for forming an electron transport layer instead of Alq$_3$.

Comparative Example 1

An organic light-emitting device was manufactured in the same manner as in Example 1, except that ADN was used as a host instead of Compound 5 when an emission layer was formed emission layer.

Evaluation Example

Driving voltage, current density, brightness, efficiency, half lifetime of the organic light-emitting devices manufactured according to Examples 1 to 8 and Comparative Example 1 were measured by using a PR650 Spectroscan Source Measurement Unit (product of PhotoResearch Company). Results thereof are shown in Table 1 below:

TABLE 1

| | Emission layer host | Emission layer dopant | Electron transport layer | Driving Voltage | Current Density | Brightness (cd/m$^2$) | Efficiency | Emission color | Half lifetime |
|---|---|---|---|---|---|---|---|---|---|
| Example1 | Compound 5 | DPVBi | Alq$_3$ | 6.65 | 50 | 2,445 | 4.79 | Blue | 188 |
| Example2 | Compound 7 | DPVBi | Alq$_3$ | 6.63 | 50 | 2,545 | 4.81 | Blue | 202 |
| Example3 | Compound 11 | DPVBi | Alq$_3$ | 6.78 | 50 | 2,380 | 4.73 | Blue | 211 |
| Example4 | Compound 17 | DPVBi | Alq$_3$ | 6.78 | 50 | 2,323 | 4.68 | Blue | 189 |
| Example5 | ADN | DPVBi | Compound | 5.71 | 50 | 2,644 | 5.29 | Blue | 196 |
| Example6 | ADN | DPVBi | Compound | 5.76 | 50 | 2,538 | 5.17 | Blue | 187 |
| Example7 | Compound 5 | DPVBi | Compound | 5.67 | 50 | 3,120 | 6.41 | Blue | 238 |
| Example8 | Compound 5 | DPVBi | Compound | 5.72 | 50 | 3,139 | 6.37 | Blue | 247 |
| Comparative | ADN | DPVBi | Alq$_3$ | 7.85 | 50 | 1,560 | 3.12 | Blue | 113 |

[1]reference current density of half-lifetime: 100 mA/cm$^2$

Referring to Table 1, it was confirmed that the organic light-emitting devices manufactured according to Examples 1 to 7 exhibit better performance than the organic light-emitting device manufactured according to Comparative Example 1.

A driving voltage of the organic light-emitting device manufactured according to Examples 1 to 4, in which Compounds 5, 7, 11, and 17 were respectively used as a host of an emission layer, was 1 V or more smaller than that of the organic light-emitting device manufactured according to Comparative Example 1. Also, brightness, efficiency, and half lifetime of the organic light-emitting devices manufactured according to Examples 1 to 4 were increased compared to the organic light-emitting device according to Comparative Example 1.

A driving voltage of the organic light-emitting devices manufactured according to Examples 5 and 6 in which Compounds 11 and 30 were respectively used as a material for forming an electron transport layer was 2 V or more smaller than that of the organic light-emitting device manufactured according to Comparative Example 1. Also brightness, efficiency, and half lifetime of the organic light-emitting devices manufactured according to Examples 5 and 6 were increased compared to the organic light-emitting device manufactured according to Comparative Example 1.

A driving voltage of the organic light-emitting devices manufactured according to Examples 7 and 8 in which Compound 5 was commonly used as a host of an emission layer and Compounds 11 and 30 were respectively used as a material for forming an electron transport layer was 2 V or more smaller than that of the organic light-emitting device manufactured according to Comparative Example 1. Brightness and efficiency of the organic light-emitting devices according to Examples 7 and 8 were increased by 100%. Half-lifetime of the organic light-emitting devices manufactured according to Examples 7 and 8 were increased by 100% or more compared to the organic light-emitting device manufactured according to Comparative Example 1.

An organic light-emitting device including a heterocyclic compound represented by Formula 1 or Formula 2 above exhibits excellent performance, for example, a low driving voltage, high brightness, high efficiency, and long lifetime. Accordingly, a flat display device including the organic light-emitting device has high quality.

The embodiments provide a novel heterocyclic compound for use in an organic light-emitting device that is driven at a low voltage and has high brightness, high efficiency, and long lifetime, an organic light-emitting device including an organic layer including the heterocyclic compound, and a flat display device including the organic light-emitting device.

While the present invention has been particularly shown and described with reference to exemplary embodiments thereof, it will be understood by those of ordinary skill in the art that various changes in form and details may be made herein without departing from the spirit and scope of the present invention as defined by the following claims.

What is claimed is:

1. A heterocyclic compound represented by Formula 1 or Formula 2 below:

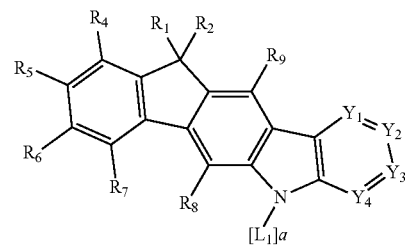

<Formula 1>

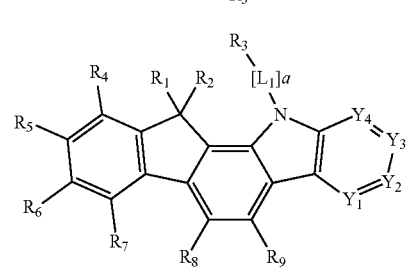

<Formula 2> wherein, $Y_1$ and $Y_4$ are each independently N or $C(R_{10})$, $Y_2$ and $Y_3$ are independently N, CH, or $C(CH_3)$, and one or more of $Y_1$ and $Y_4$ are N, $R_1$ to $R_4$ and $R_7$ to $R_{10}$ are each independently a hydrogen atom, a deuterium atom, a halogen atom, a hydroxyl group, a cyano group, a nitro group, a carboxylic group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ heteroaryl group, or a group represented by $N(Q_1)(Q_2)$ where $Q_1$ and $Q_2$ are each independently a hydrogen atom, a deuterium atom, a halogen atom, a hydroxyl group, a cyano group, an amino group, a nitro group, a carboxylic group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ heteroaryl group, $R_5$ to $R_6$ are each independently a hydrogen atom, a deuterium atom, a halogen atom, a cyano group, or a substituted or unsubstituted methyl group, $L_1$ is a substituted or unsubstituted $C_6$-$C_{30}$ arylene group or a substituted or unsubstituted $C_3$-$C_{30}$ heteroarylene group, and a is an integer from 1 to 3.

2. The heterocyclic compound of claim 1, wherein $Y_1$ is N, $Y_2$ and $Y_3$ are CH or $C(CH_3)$ and Y4 is $C(R_{10})$.

3. The heterocyclic compound of claim 1, wherein $R_1$ to $R_4$ and $R_7$ to $R_{10}$ are each independently a hydrogen atom, a deuterium atom, a halogen atom, a hydroxyl group, a cyano group, a nitro group, a carboxylic group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted methoxy group, a substituted or unsubstituted ethoxy group, a substituted or unsubstituted phenyl group, a substituted or unsubstituted biphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted phenanthridinyl group, a substituted or unsubstituted phenanthrolinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyridoindolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted carbazolyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted benzooxazolyl group, a substituted or unsubstituted isooxazolyl group, a substituted or unsubstituted oxadiazolyl group, a substituted or unsubstituted triazolyl group, a substituted or unsubstituted triazinyl group, a substituted or unsubstituted tetrazolyl group, or a group represented by $N(Q_1)(Q_2)$ where $Q_1$ and $Q_2$ are each independently a hydrogen atom, a deuterium atom, a halogen atom, a hydroxyl group, a cyano group, an amino group, a nitro group, a carboxylic group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyridinyl group.

4. The heterocyclic compound of claim 1, wherein $R_1$ to $R_4$ and $R_7$ to $R_{10}$ are each independently a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted imidazolyl group, a substituted or unsubstituted benzoimidazolyl group, a substituted or unsubstituted pyridinyl group, a substituted or unsubstituted quinolinyl group, a substituted or unsubstituted pyrimidinyl group, a substituted or unsubstituted imidazopyrimidinyl group, a substituted or unsubstituted indolyl group, a substituted or unsubstituted pyridoindolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxadiazolyl group, a substituted or unsubstituted triazinyl group, or a group represented by $N(Q_1)(Q_2)$ where $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group.

5. The heterocyclic compound of claim 1, wherein $R_3$ is a hydrogen atom, a deuterium atom, a halogen atom, a substituted or unsubstituted methyl group; a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted fluorenyl group, a substituted or unsubstituted phenanthrenyl group, a substituted or unsubstituted imidazolyl group, a substituted or unsubstituted benzoimidazolyl group, a substituted or unsubstituted pyridinyl group, a substituted or unsubstituted pyrimidinyl group, a substituted or unsubstituted quinolinyl group, a substituted or unsubstituted imidazopyrimidinyl group, a substituted or unsubstituted indolyl group, a substituted or unsubstituted pyridoindolyl group, a substituted or unsubstituted carbazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted oxadiazolyl group, a substituted or unsubstituted triazinyl group, or a group represented by $N(Q_1)(Q_2)$ where $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group, and $R_1$, $R_2$, $R_4$, and $R_7$ to $R_{10}$ are each independently a hydrogen atom, a deuterium atom, a halogen atom, a cyano group, a substituted or unsubstituted methyl group, or a substituted or unsubstituted phenyl group.

6. The heterocyclic compound of claim 1, wherein $R_3$ is a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, or any one of groups represented by Formulae 2A to 2S below, and $R_1$, $R_2$, $R_4$, and $R_7$ to $R_{10}$ are each independently a hydrogen atom, a deuterium atom, a halogen atom, a cyano group, a substituted or unsubstituted methyl group, or a substituted or unsubstituted phenyl group:

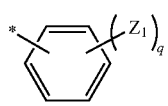

<Formula 2A>

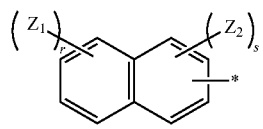

<Formula 2B>

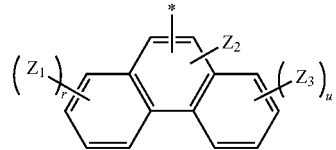

<Formula 2C>

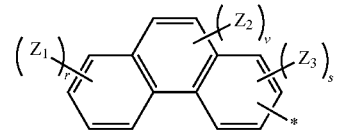

<Formula 2D>

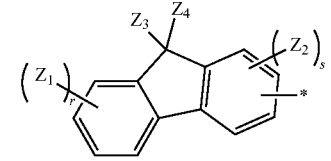

<Formula 2E>

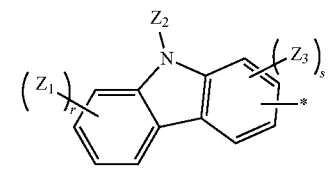

<Formula 2F>

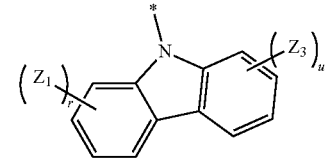

<Formula 2G>

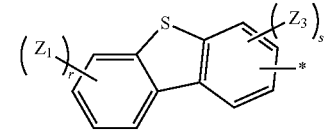

<Formula 2H>

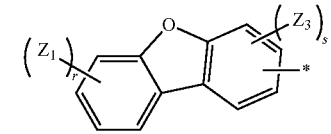

<Formula 2I>

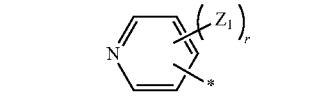

<Formula 2J>

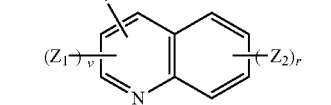

<Formula 2K>

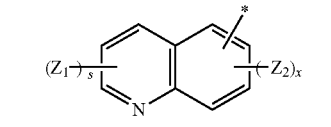

<Formula 2L>

-continued

<Formula 2M>

<Formula 2N>

<Formula 2O>

<Formula 2P>

<Formula 2Q>

<Formula 2R>

<Formula 2S> wherein,
Z₁, Z₂, Z₃, Z₄ and Z₅ are each independently a hydrogen atom, a deuterium atom, a halogen atom, a hydroxyl group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted biphenyl group, a substituted or unsubstituted pyridinyl group, a substituted or unsubstituted naphthyl group, or a substituted or unsubstituted anthryl group, a plurality of $Z_1$, $Z_2$, $Z_3$, $Z_4$ and $Z_5$ are identical to or different from each other, q is an integer from 1 to 5,
r and u are each independently an integer from 1 to 4,
s and x are each independently an integer from 1 to 3,
v is an integer from 1 to 2,
and * represents a binding site.

7. The heterocyclic compound of claim 1, wherein $R_3$ is a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, or any one of groups represented by Formulae 3A to 3P below, and $R_1$, $R_2$, $R_4$, and $R_7$ to $R_{10}$ are each independently a hydrogen atom, a deuterium atom, a halogen atom, a cyano group, a substituted or unsubstituted methyl group, or a substituted or unsubstituted phenyl group:

<Formula 3A>

<Formula 3B>

<Formula 3C>

<Formula 3D>

<Formula 3E>

<Formula 3F>

<Formula 3G>

<Formula 3H>

<Formula 3I>

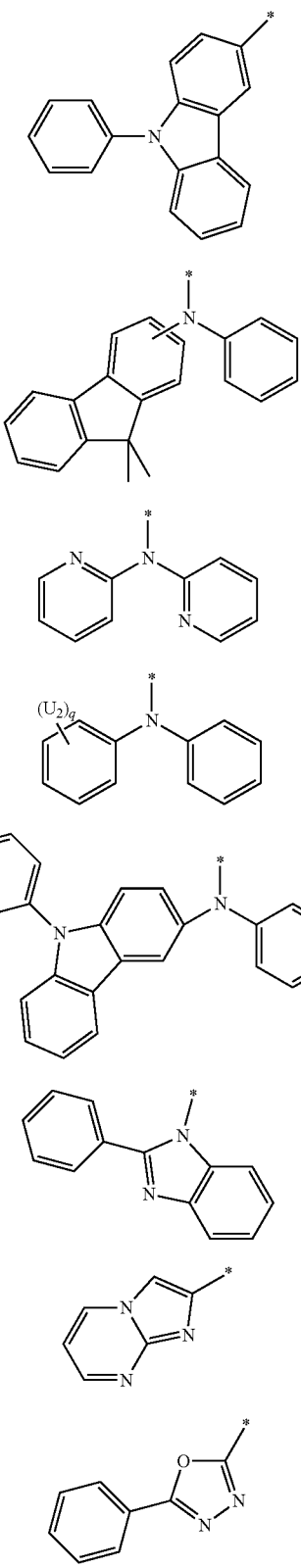

<Formula 3J>

<Formula 3K>

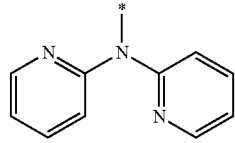

<Formula 3L>

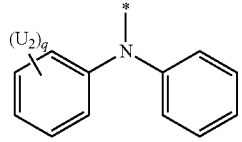

<Formula 3M>

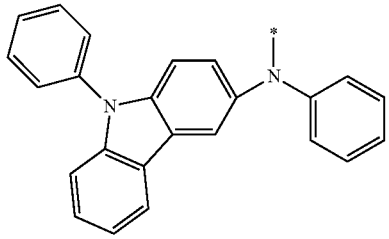

<Formula 3N>

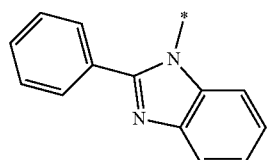

<Formula 3O>

<Formula 3P> wherein,
$U_1$ is a hydrogen atom, a deuterium atom, a halogen atom, or a methoxy group and $U_2$ is a hydrogen atom or a halogen atom, wherein a plurality of $U_1$ and $U_2$ are identical to or different from each other,
q is an integer of 1 to 5,
and * indicates a binding site.

8. The heterocyclic compound of claim 1, wherein $L_1$ is a substituted or unsubstituted phenylene group, a substituted or unsubstituted naphthylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrycenylene group, a substituted or unsubstituted pherylenylene group, a substituted or unsubstituted fluorenylene group, a substituted or unsubstituted spiro-fluorenylene group, a substituted or unsubstituted carbazolylene group, a substituted or unsubstituted pyridinylene group, a substituted or unsubstituted benzoimidazolene group, a substituted or unsubstituted imidazopyrimidinylene group, or a substituted or unsubstituted oxadiazolylene group.

9. The heterocyclic compound of claim 1, wherein $L_1$ is any one of groups represented by Formulae 4A to 4F below:

<Formula 4A>

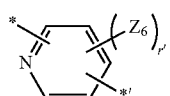

<Formula 4B>

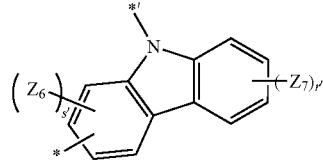

<Formula 4C>

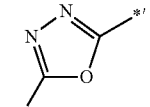

<Formula 4D>

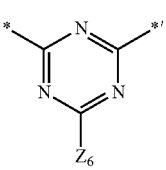

<Formula 4E>

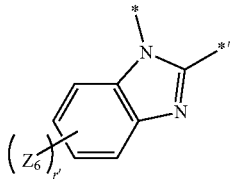

<Formula 4F> wherein,
$Z_6$ is a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted methoxy group, or a substituted or unsubstituted phenyl group, a plurality of $Z_6$ are identical to or different from each other, r' is an integer from 1 to 4, s' is an integer from 1 to 3, and * and *' each indicate a binding site.

10. The heterocyclic compound of claim 1, wherein a is 0 or 1.

11. The heterocyclic compound of claim 1, wherein the heterocyclic compound represented by Formula 1 or Formula 2 above is any one of compounds represented by Compound 1 to 6, 8 to 11, 13 to 17, 19 to 25, 27 to 64, 66 to 76, 78 to 109, and 110 to 112 below:

1

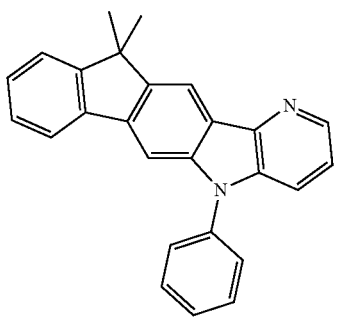

2

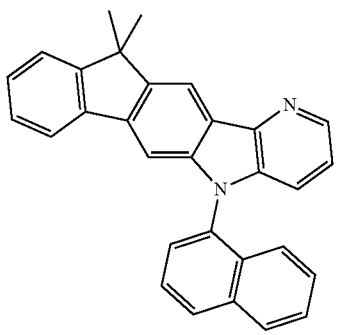

3

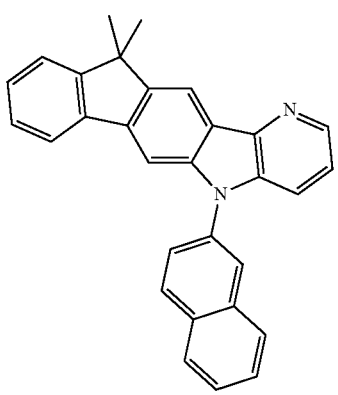

4

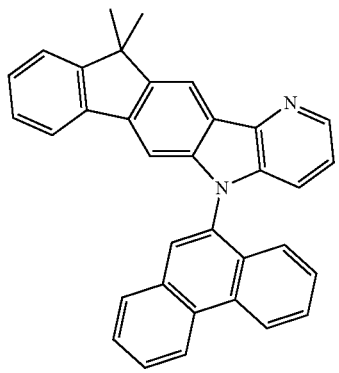

5

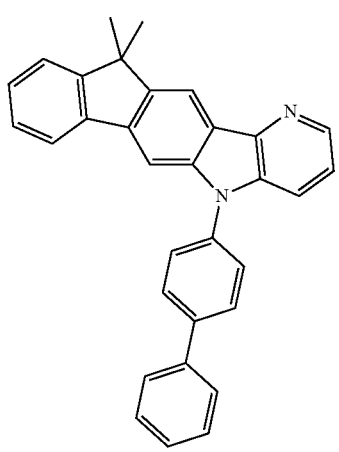

6

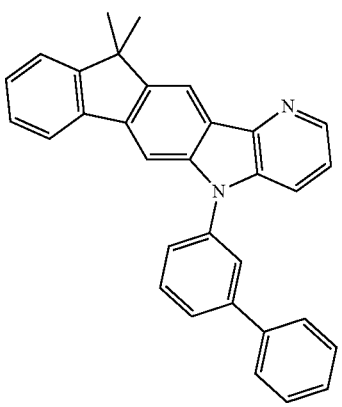

8

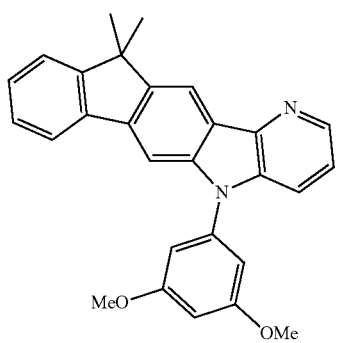

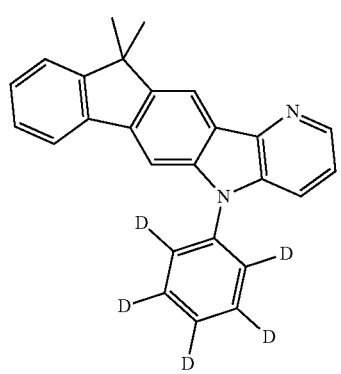
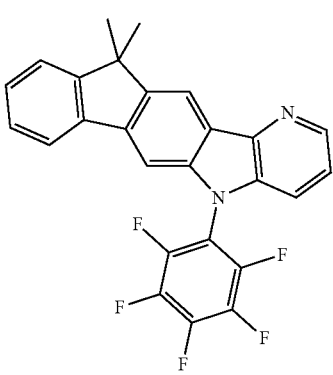
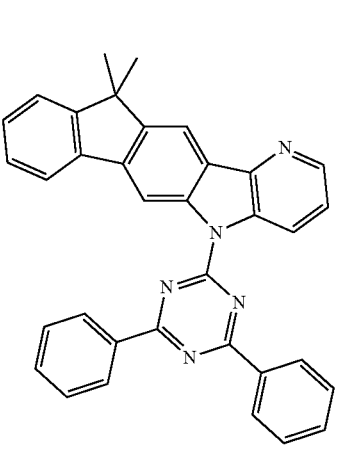
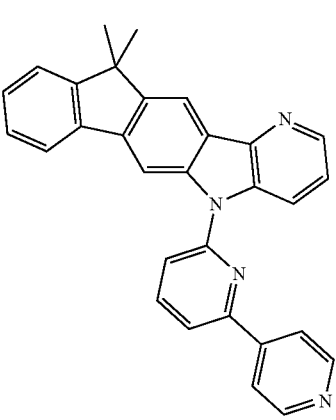
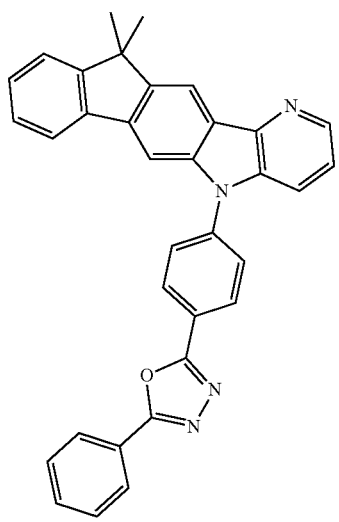
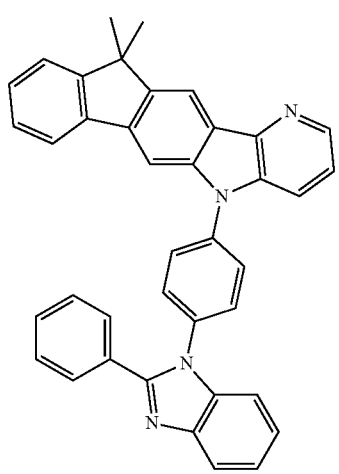
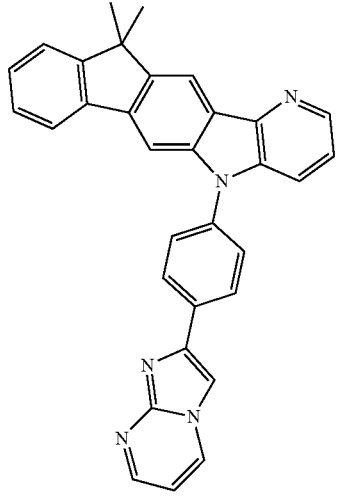

17
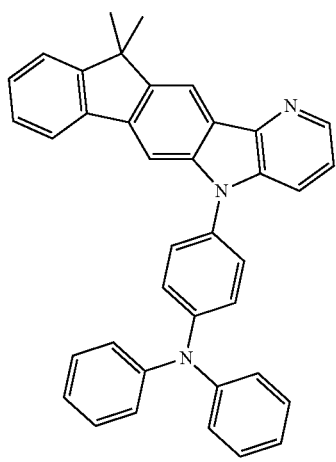
19
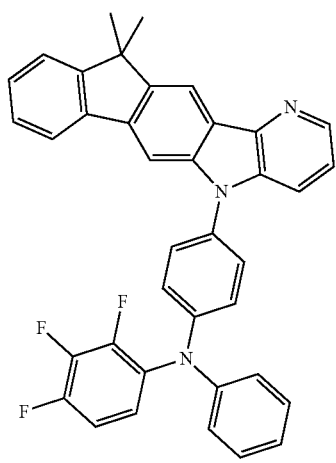
20
21
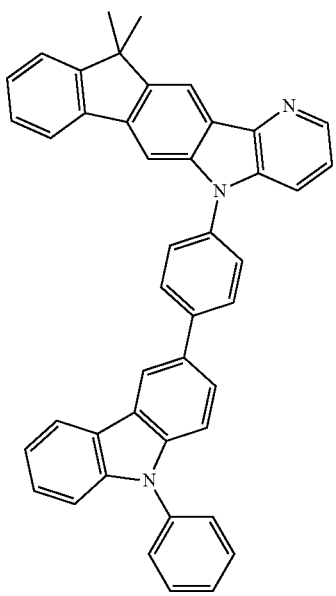
22
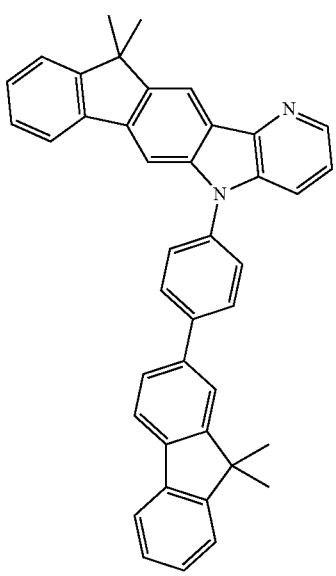

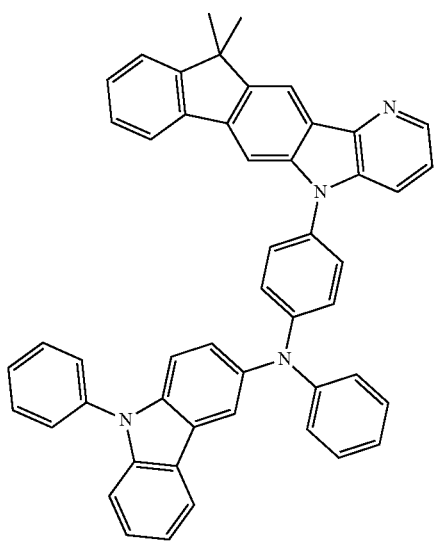
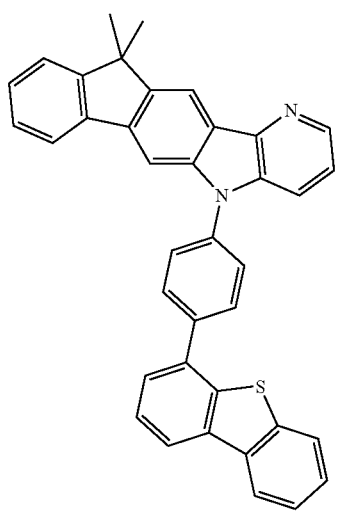
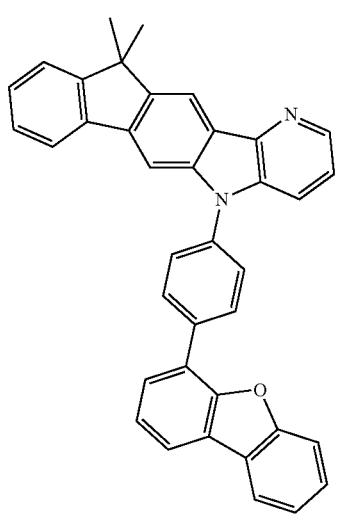
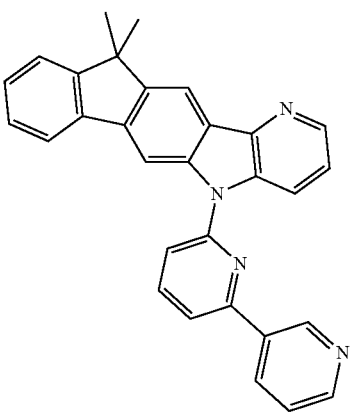

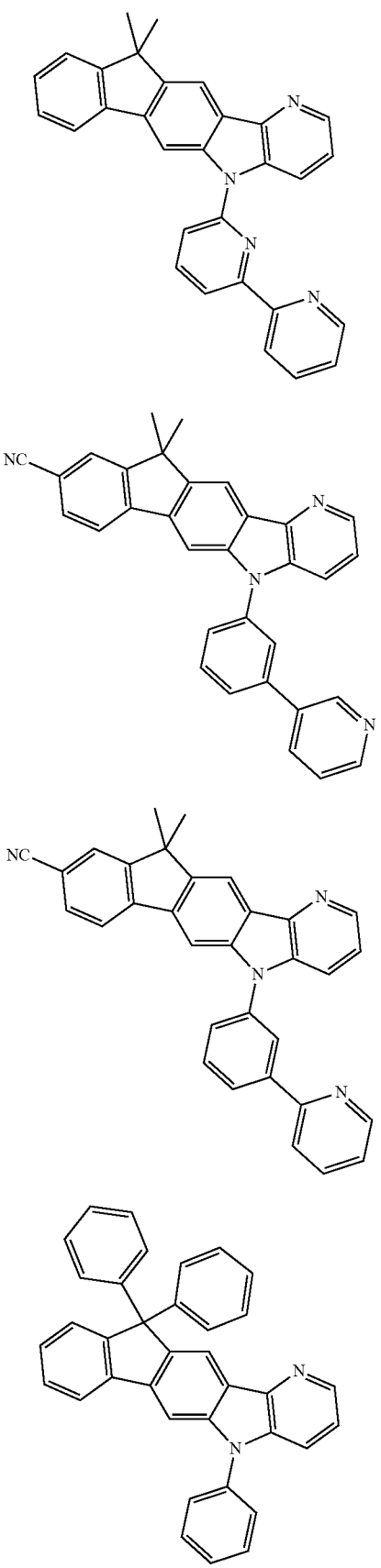

37
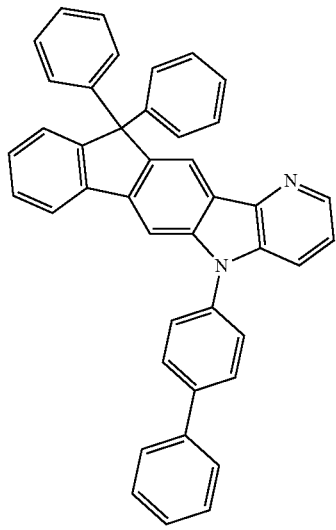
38
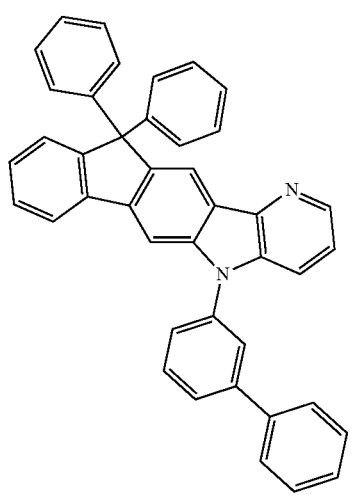
39
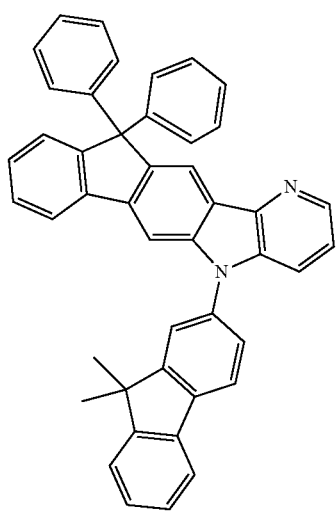
40
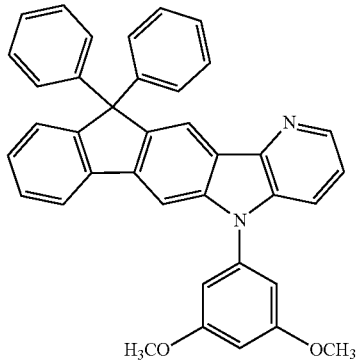
40
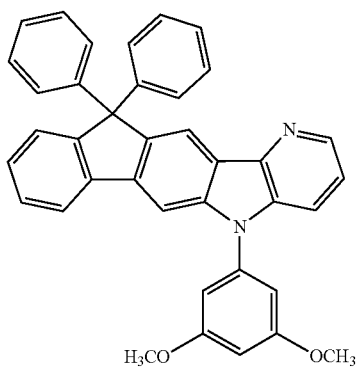
41
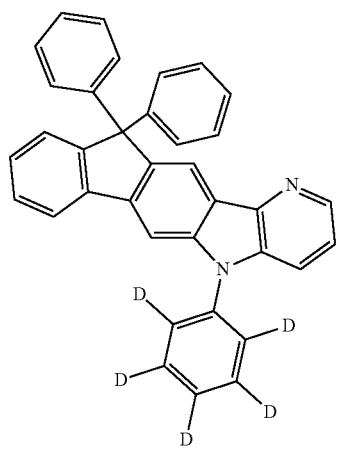
42
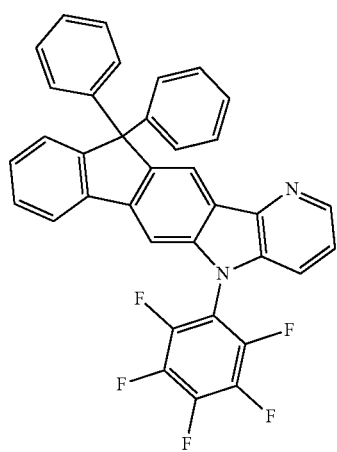

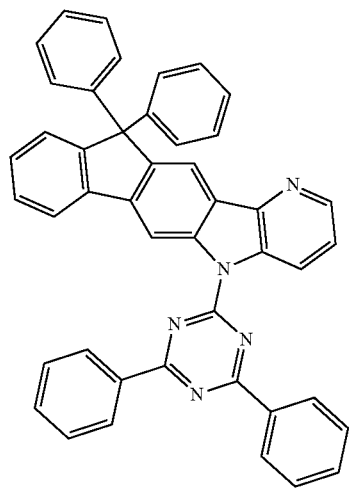
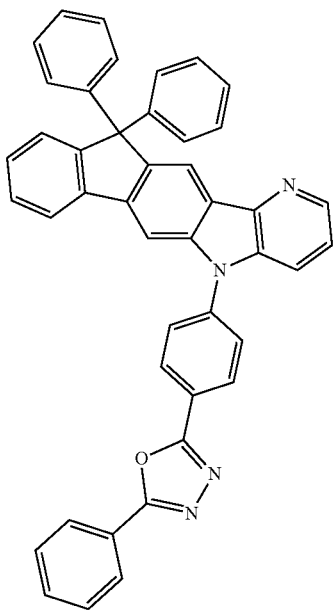
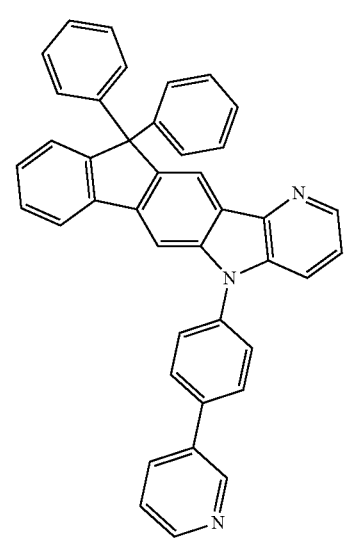
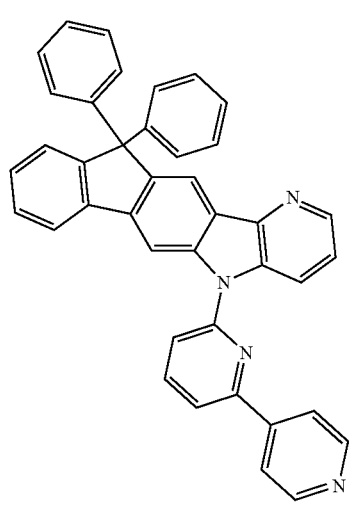
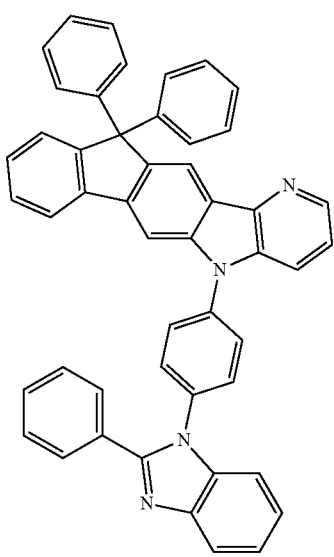

48
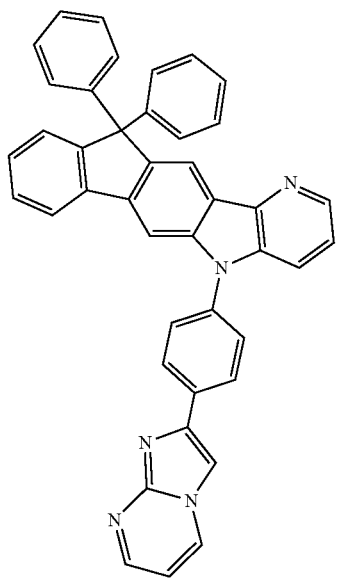
49
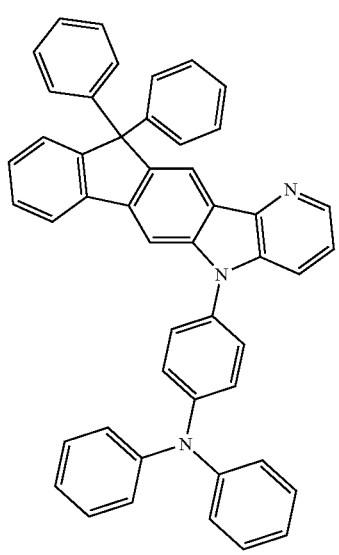
50
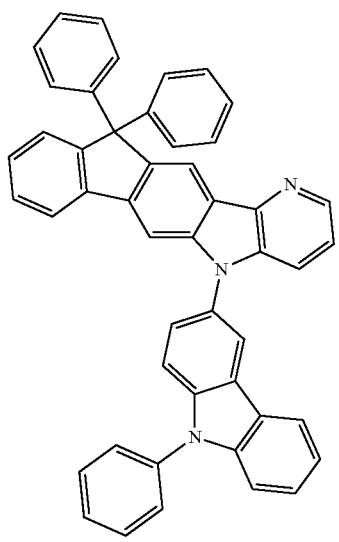
51
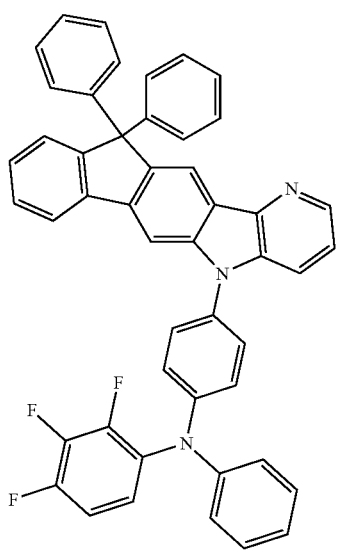
52
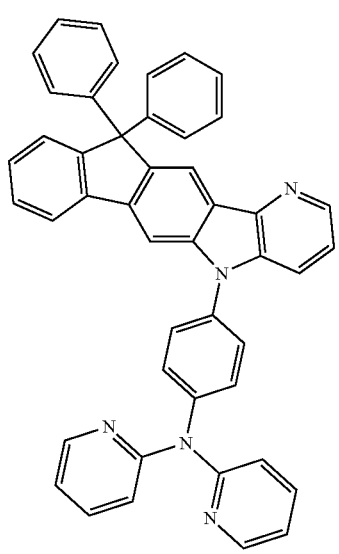

53
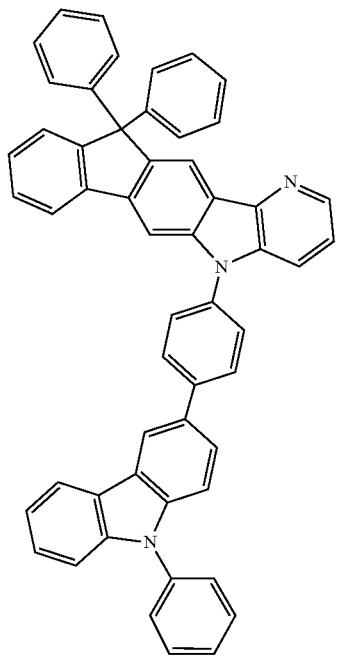
135
54
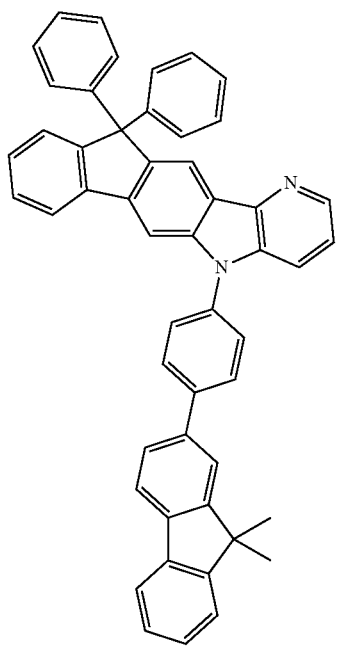
55
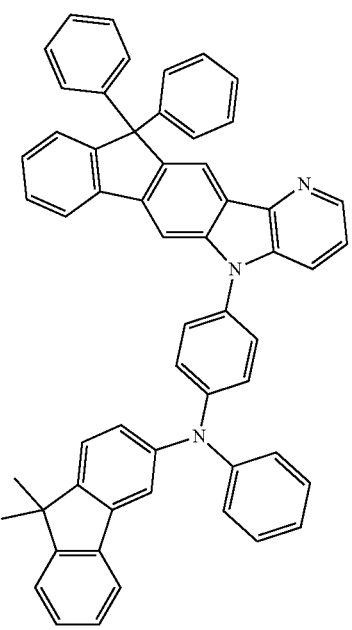
136
56
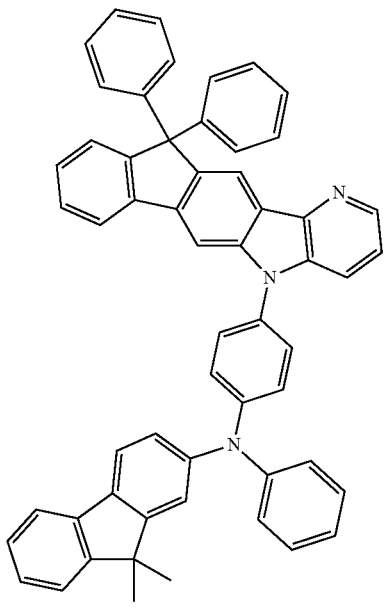

-continued
57
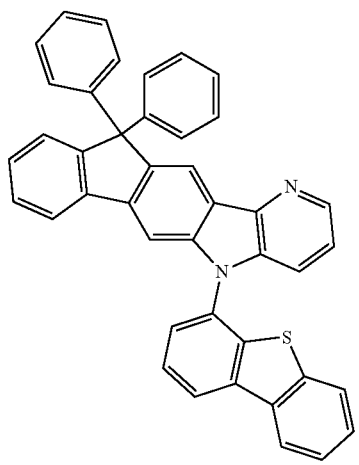
58
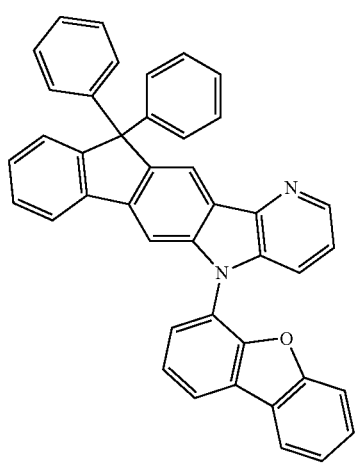
59
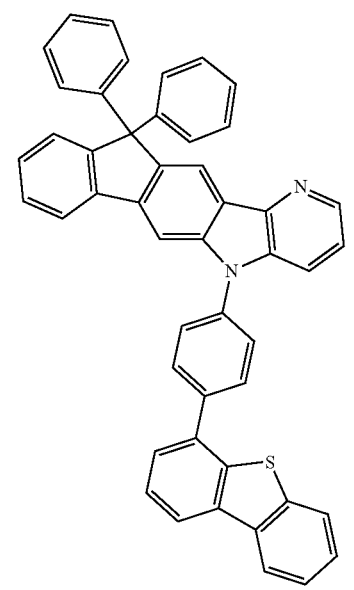
-continued
60
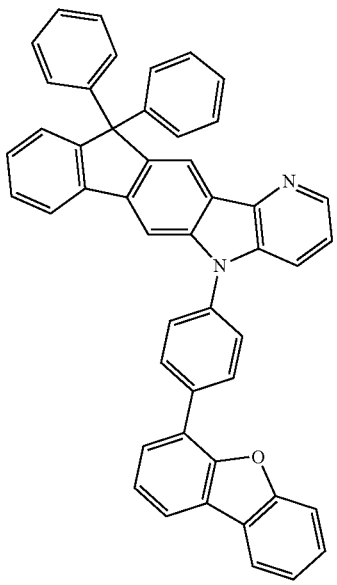
61
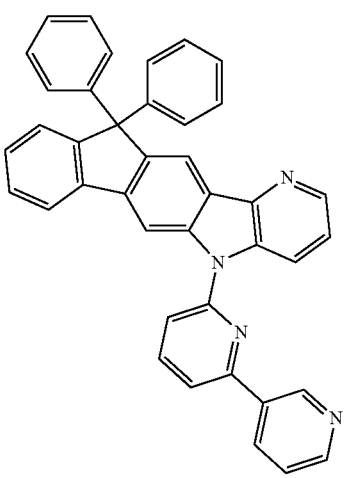
62
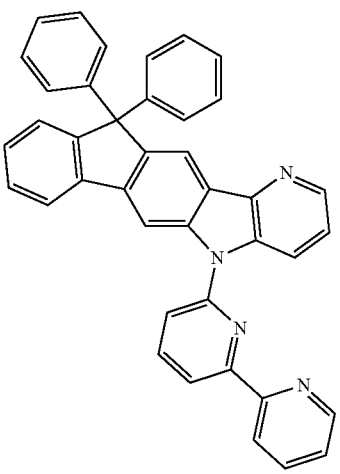

63
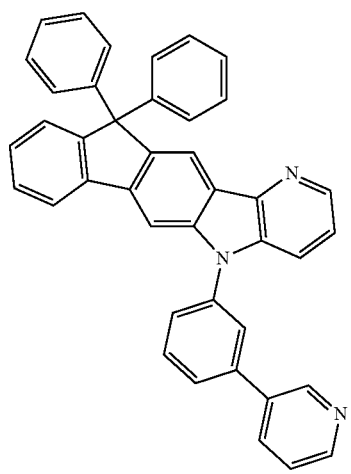
64
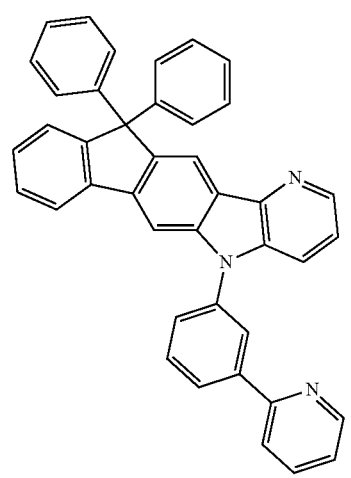
66
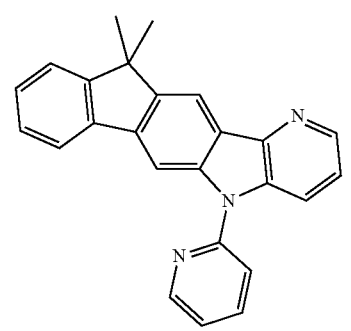
67
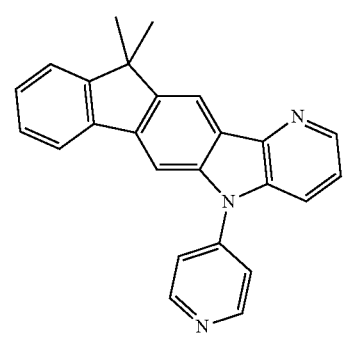
68
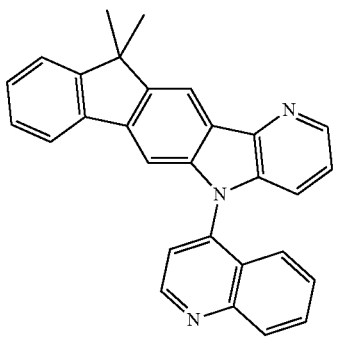
69
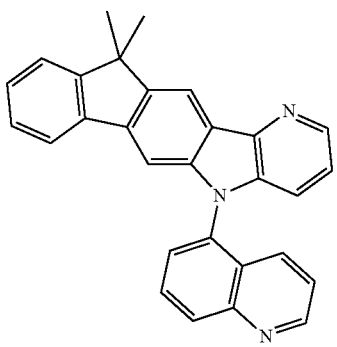
70
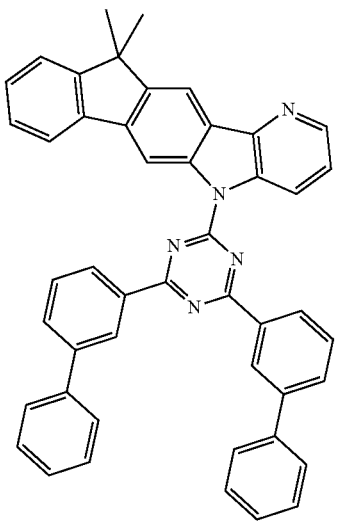
71
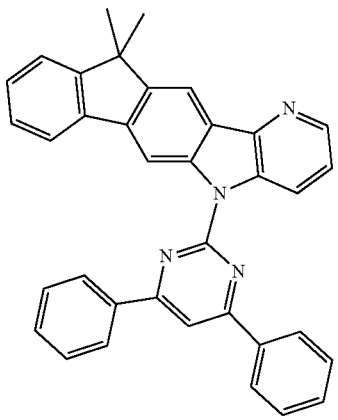

72
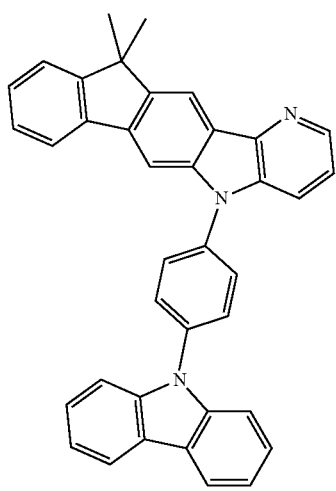
73
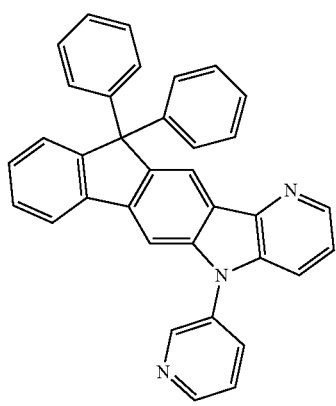
74
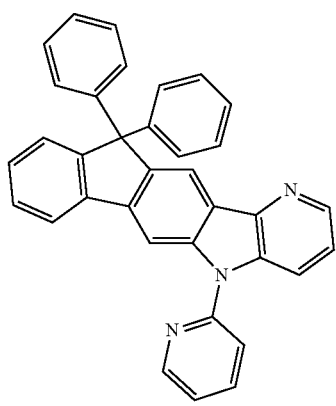
75
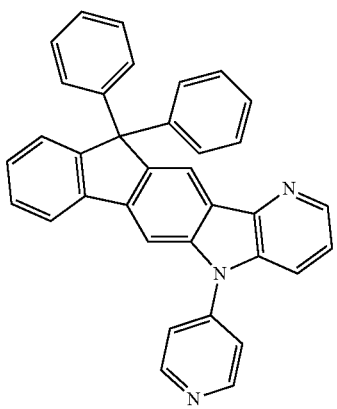
76
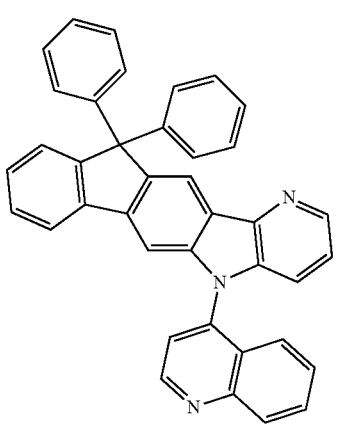
78
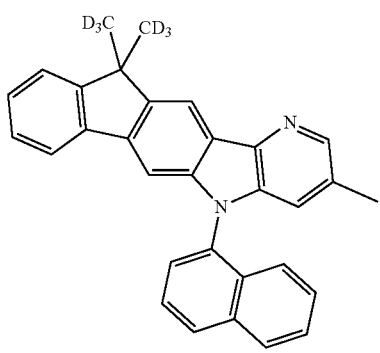
79
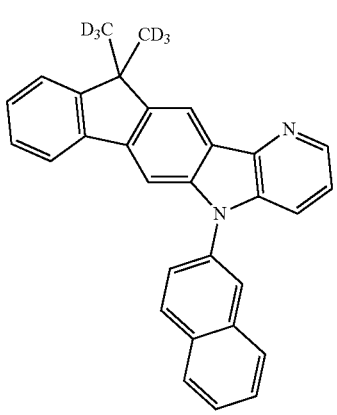

143
-continued
80
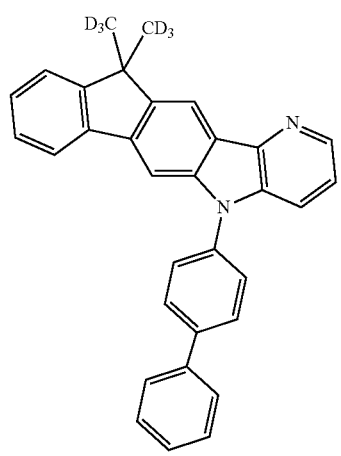
81
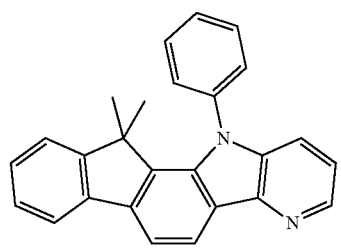
82
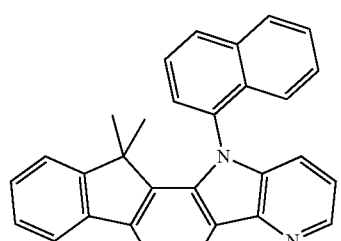
83
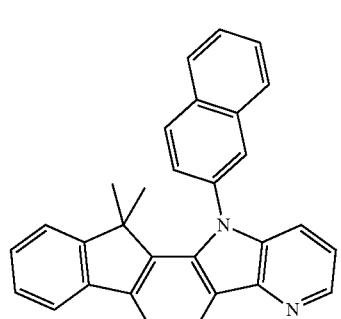
84
144
-continued
85
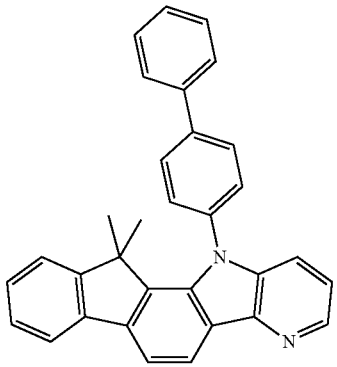
86
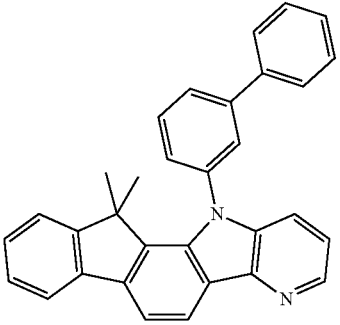
87
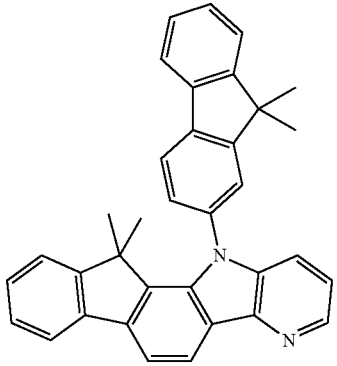
88
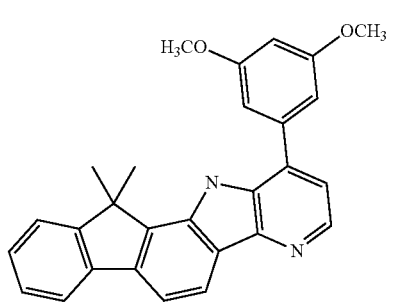

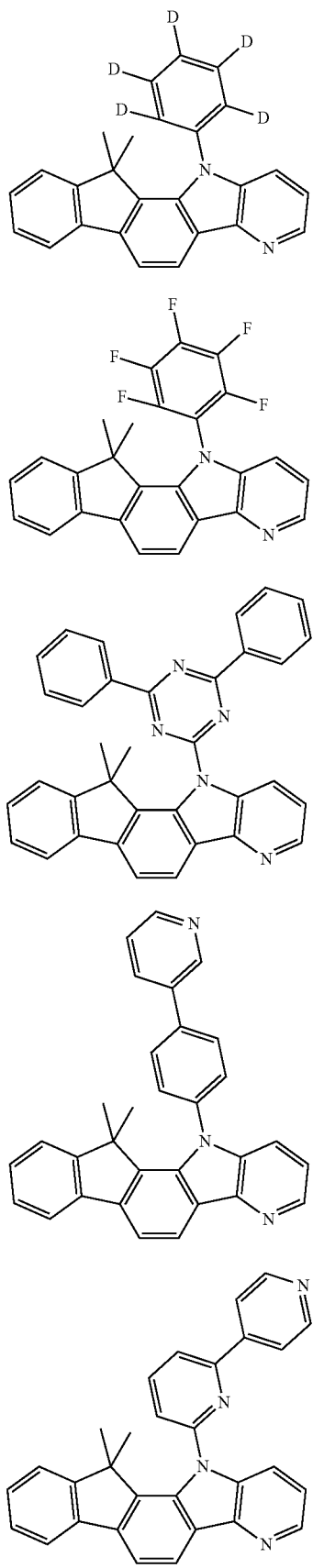
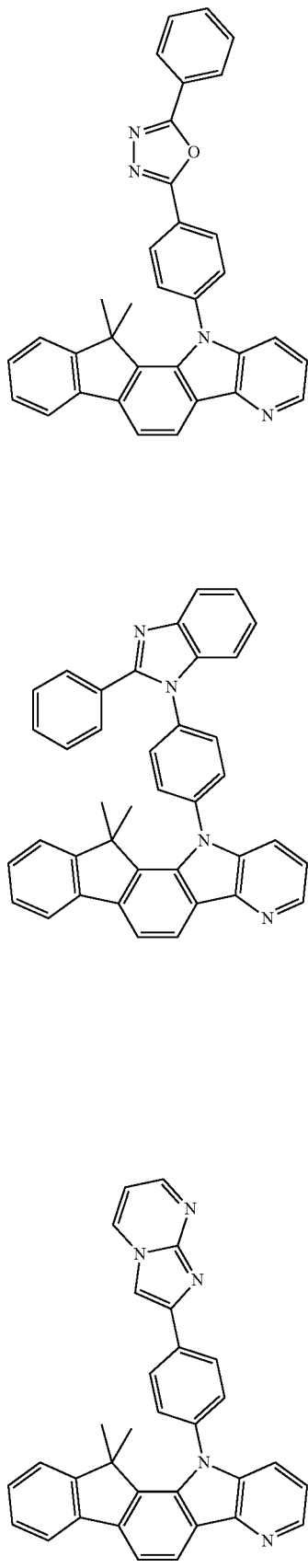

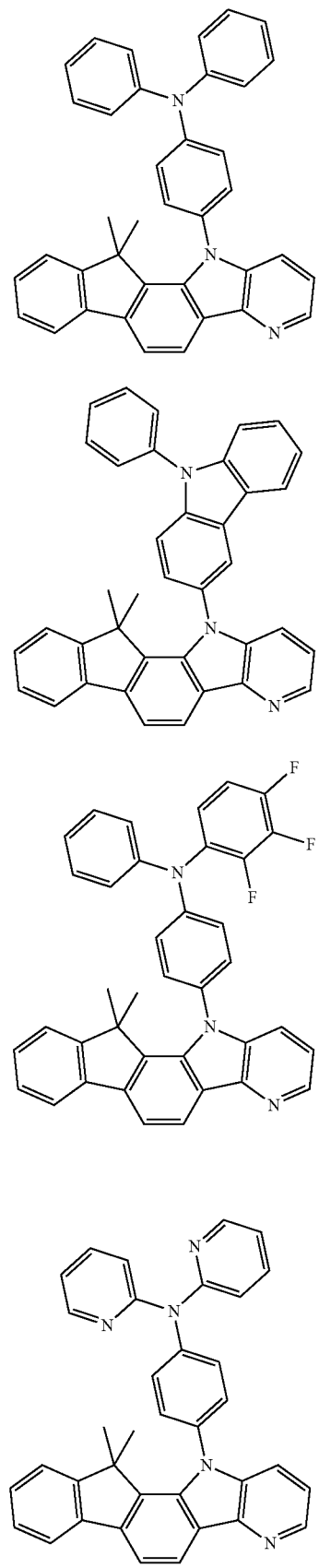
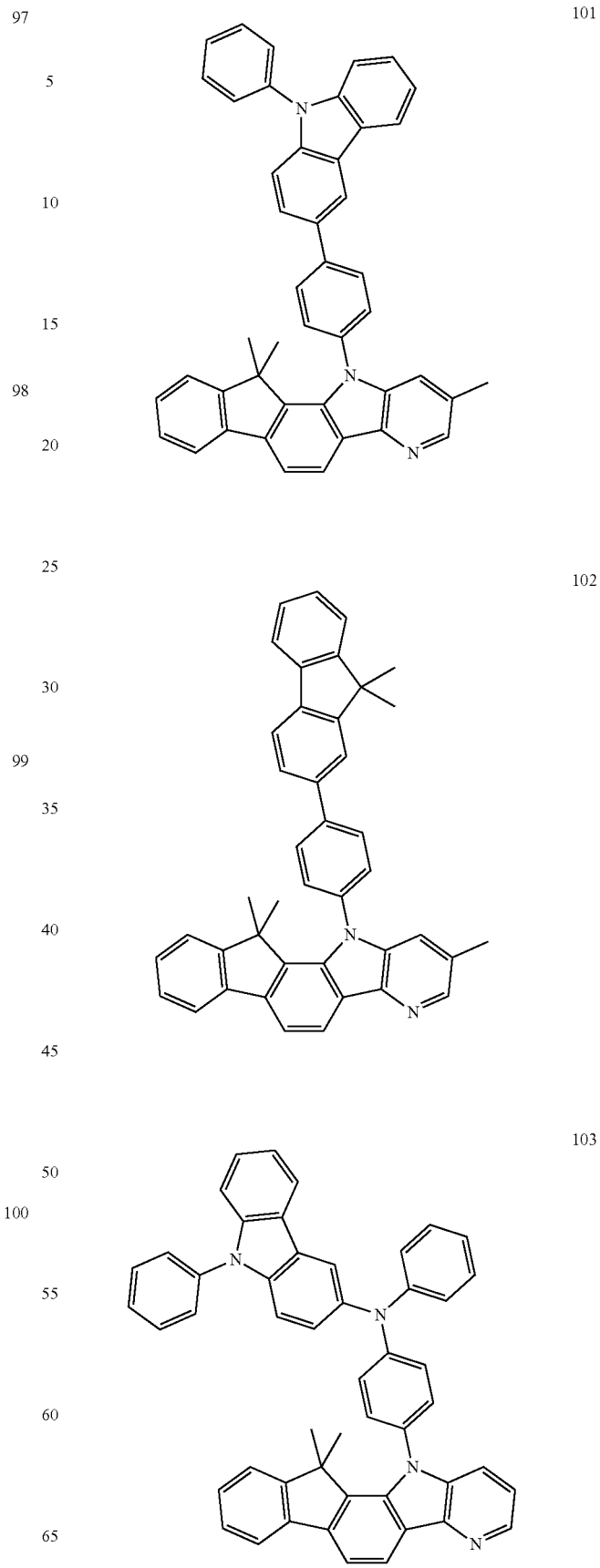

149
-continued
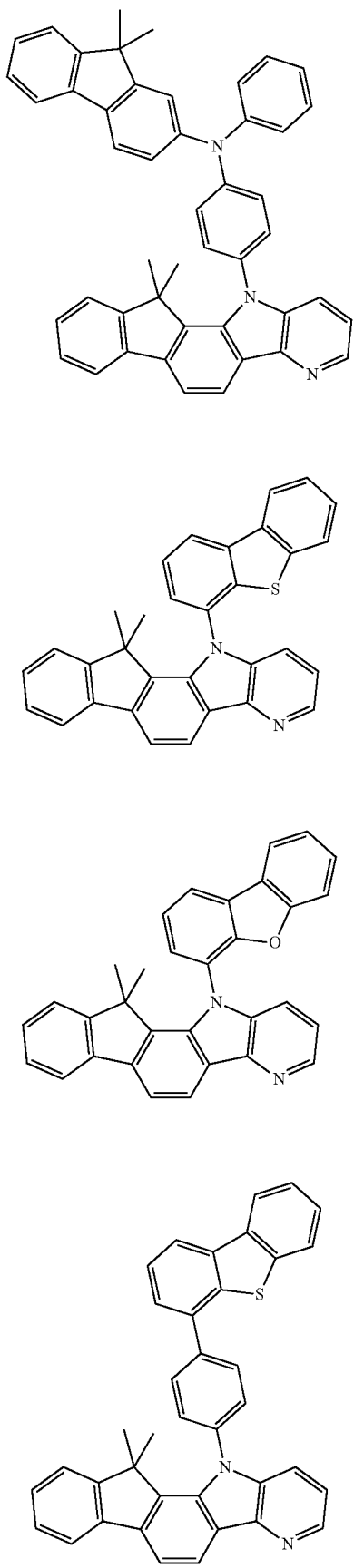
104
105
106
107
150
-continued
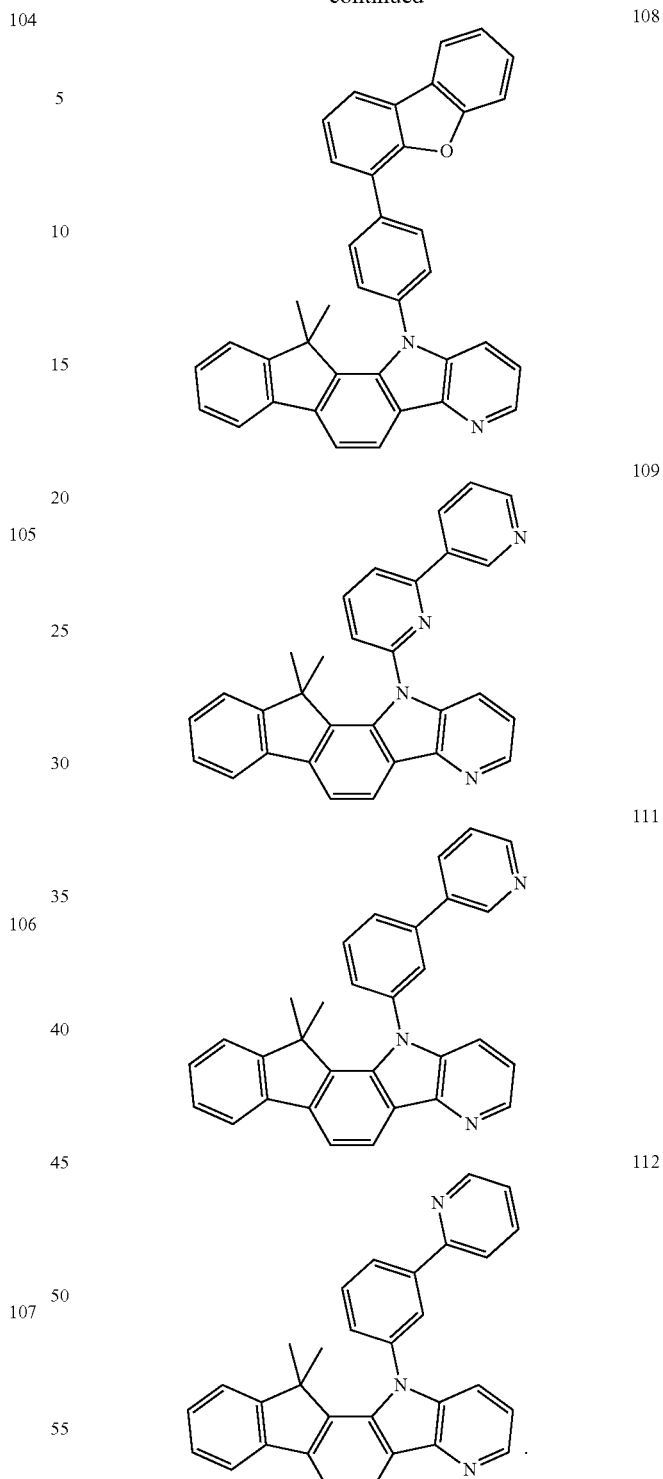
108
109
111
112
12. An organic light-emitting device, comprising:
a first electrode;
a second electrode facing the first electrode; and
at least one first layer interposed between the first electrode and the second electrode,
wherein the first layer comprises one or more heterocyclic compounds of claim 1.

13. The organic light-emitting device of claim 12, further comprising, one or more additional layers, including, a hole injection layer, a hole transport layer, a functional layer having a hole injection function and a hole transport function, an electron blocking layer, an emission layer, a hole blocking layer, an electron transport layer, an electron injection layer, a functional layer having an electron injection function and an electron transport function, or a combination of two or more thereof between the first electrode and the second electrode.

14. The organic light-emitting device of claim 13, wherein at least one layer selected from the first layer and the one or more additional layers is formed by using a wet process.

15. The organic light-emitting device of claim 12, wherein the first layer is an emission layer, an electron injection layer, an electron transport layer, or a functional layer having a hole injection function and a hole transport function.

16. The organic light-emitting device of claim 12, wherein the first layer is an emission layer, one of the one or more heterocyclic compounds is used as a fluorescent host or a phosphorescent host, and the first layer further includes a fluorescent dopant or a phosphorescent dopant.

17. The organic light-emitting device of claim 16, wherein the phosphorescent dopant includes an organometallic complex including Ir, Pt, Os, Re, Ti, Zr, Hf, or a combination of two or more thereof.

18. The organic light-emitting device of claim 12, wherein the first layer is an emission layer, one of the one or more heterocyclic compounds is used as a fluorescent dopant, and the first layer further comprises a fluorescent host or a phosphorescent host.

19. The organic light-emitting device of claim 18, wherein the fluorescent host or the phosphorescent host includes another one of the one or more heterocyclic compounds, wherein the another one of the one or more heterocyclic compounds is different from the fluorescent dopant heterocyclic compound.

20. The organic light-emitting device of claim 12, wherein the first layer is an emission layer, an electron transport layer, or a functional layer having a hole injection function and a hole transport function, and the first layer further includes at least one selected from an anthracene-based compound, an arylamine-based compound, and a styryl-based compound.

21. The organic light-emitting device of claim 13, wherein at least one selected from the hole injection layer, the hole transport layer, and the functional layer having a hole injection function and a hole transport function further includes a charge generating material.

22. The organic light-emitting device of claim 13, wherein when the first layer is an electron transport layer or the one or more additional layers is an electron transport layer, the electron transport layer includes an electron transport organic material and a metal-containing material.

23. The organic light-emitting device of claim 12, wherein the first layer is an electron transport layer, and an emission layer is additionally interposed between the first electrode and the second electrode, the emission layer includes at least one region selected from a red emission region, a green emission region, a blue emission region, and a white emission region, and at least one region of the red emission region, the green emission region, the blue emission region, and the white emission region includes a phosphorescent compound.

24. A flat display device comprising: a transistor that includes a source, a drain, a gate, and an active layer; and the organic light-emitting device of claim 12, wherein any one of the source and the drain is electrically connected to the organic light-emitting device.

25. The heterocyclic compound of claim 1, wherein:
the heterocyclic compound is represented by Formula 1, $Y_1$ is N, $Y_2$-$Y_4$ are CH, $R_1$ and $R_2$ are $CH_3$, $R_4$-$R_9$ are H, and a is 1.

26. The heterocyclic compound of claim 1, wherein the heterocyclic compound is represented by Compound 5, below:

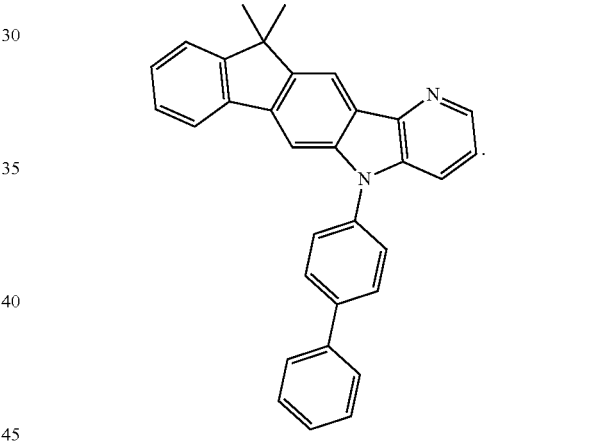

* * * * *